(12) United States Patent
Wettstein et al.

(10) Patent No.: US 7,202,329 B2
(45) Date of Patent: Apr. 10, 2007

(54) TSG101-GAGP6 INTERACTION AND USE THEREOF

(75) Inventors: Daniel Albert Wettstein, Salt Lake City, UT (US); Scott Morham, Salt Lake City, UT (US); Kenton Zavitz, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/972,035

(22) Filed: Oct. 4, 2001

(65) Prior Publication Data

US 2002/0173622 A1 Nov. 21, 2002

Related U.S. Application Data

(60) Provisional application No. 60/276,259, filed on Mar. 14, 2001.

(51) Int. Cl.
*C07K 14/00* (2006.01)
(52) U.S. Cl. .................. 530/300; 530/350; 435/69.1; 435/320.1; 536/23.4; 536/23.72
(58) Field of Classification Search ............... 530/300, 530/350; 536/23.32, 23.72, 23.4; 435/69.1, 435/320.1
See application file for complete search history.

(56) References Cited

U.S. PATENT DOCUMENTS

| 5,807,995 | A | 9/1998 | Cohen et al. |
| 5,891,668 | A | 4/1999 | Li et al. |
| 5,892,016 | A | 4/1999 | La Brie et al. |
| 6,248,523 | B1 | 6/2001 | Cohen et al. |
| 6,274,312 | B1 | 8/2001 | Gish et al. |
| 2003/0049607 | A1 | 3/2003 | Greener et al. |

FOREIGN PATENT DOCUMENTS

WO  WO 02/094314  11/2002

OTHER PUBLICATIONS

Strack PNAS Nov. 2000 vol. 97, No. 24 pp. 13063-13068.*
Patniak PNAS Nov. 2000 vol. 97, No. 24 pp. 1369-13074.*
Ott et alJ. Virol. 1998 72: 2962-2968.*
Heinrichs et al., 1997 PNAS 94: 115-120.*
Desai et al., Proc Natl Acad Sci U S A. Nov. 1986;83(21):8380-4.*
Parent, Leslie J., et al., "Positionally Independent and Exchangeable Late Budding Functions of the Rous Sarcoma Virus and Human Immunodeficiency Virus Gag Proteins", *Journal of Virology*, Sep. 1995; 69(9):5455-5460.
NCBI Entrez Protein Database Accession No.: AAB38034, Dec. 5, 1996.
Zhang, Yi-Ming, et al., "Drug Resistance during Indinavir Therapy Is Caused by Mutations in the Protease Gene and in Its Gag Substrate Cleavage Sites", *Journal of Virology*, Sep. 1997; 71 (9) :6662-6670.
Puffer, Bridget A., et al., "Equine Infectious Anemia Virus Utilizes a YXXL Motif within the Late Assembly Domain of the Gag p9 Protein", *Journal of Virology*, Sep. 1997; 71 (9): 6541-6546.
NCBI Entrez Protein Database Accession No. AAB83138, Nov. 6, 1997.
NCBI Entrez Protein Database Accession No. AAB83216, Nov. 6, 1997.
NCBI Entrez Protein Database Accession No. AAB83821, Nov. 6, 1997.
Yasuda, Jiro, et al., "A Proline-Rich Motif (PPPY) in the Gag Polyprotein of Mason-Pfizer Monkey Virus Plays a Maturation-Independent Role in Virion Release", *Journal of Virology*, May 1998; 72(5):4095-4103.
NCBI Entrez Protein Database Accession No. P35962, Jul. 15, 1998.
Crump, Colin M., et al., "Inhibition of the Interaction between Tyrosine-based Motifs and the Medium Chain Subunit of the AP-2 Adaptor Complex by Specific Tyrphostins", *The Journal of Biological Chemistry*, Oct. 23, 1998; 273(43):28073-28077.
Puffer, Bridget A., et al., "Equine Infectious Anemia Virus Gag Polyprotein Late Domain Specifically Recruits Cellular AP-2 Adapter Protein Complexes during Virion Assembly", *Journal of Virology*, Dec. 1998; 72(12):10218-10221.
Sorkina, Tatiana, et al., "Clathrin, adaptors and eps15 in endosomes containing activated epidermal growth factor receptors", *Journal of Cell Science*, 1999; 112:317-327.
Yuan, Bing, et al., "Mutations altering the Moloney murine leukemia virus p12 Gag protein affect virion production and early events of the virus life cycle", *The EMBO Journal*, 1999; 18(17):4700-4710.
NCBI Entrez Protein Database Accession No. AAD03232, Jan. 6, 1999.
NCBI Entrez Protein Database Accession No. AAD03240, Jan. 6, 1999.
U.S. Appl. No. 09/971,549, filed Oct. 4, 2001, Zavitz et al.
Garnier, Laurence, et al., "Identification of Retroviral Late Domains as Determinants of Particle Size", *Journal of Virology*, Mar. 1999; 73(3):2309-2320.
Harty, Ronald N., et al., "A Proline-Rich Motif within the Matrix Protein of Vesicular Stomatitis Virus and Rabies Virus Interacts with WW Domains of Cellular Proteins: Implications for Viral Budding", *Journal of Virology*, Apr. 1999; 73(4):2921-2929.
Craven, Rebecca C. et al., "Late Domain Function Identified in the Vesicular Stomatitis Virus M Protein by Use of Rhabdovirus-Retrovirus Chimeras", *Journal of Virology*, Apr. 1999; 73(4):3359-3365.

(Continued)

*Primary Examiner*—Myron G. Hill
(74) *Attorney, Agent, or Firm*—Herbert I Ley, III; Jay Z. Zhang; Myriad IP Department

(57) ABSTRACT

Isolated protein complexes are provided comprising Tsg101 and HIV GAGp6. The protein complexes are useful in screening assays for selecting compounds effective in modulating the Tsg101-HIV GAGp6 interaction within the protein complexes.

64 Claims, 4 Drawing Sheets

OTHER PUBLICATIONS

Harvey, Kieran F., et al., "Nedd4-like proteins: an emerging family of ubiquitin-protein ligases implicated in diverse cellular functions", *Trends in Cell Biology*, May 1999; 9:166-169.

Deschambeault, Julie, et al., "Polarized Human Immunodeficiency Virus Budding in Lymphocytes Involves a Tyrosine-Based Signal and Favors Cell-to-Cell Viral Transmission", *Journal of Virology*, Jun. 1999; 73(6):5010-5017.

NCBI Entrez Protein Database Accession No. AAF35354, Feb. 23, 2000.

Alexander, Louis, et al., "Unusual Polymorphisms in Human Immunodeficiency Virus Type 1 Associated with Nonprogressive Infection", *Journal of Virology*, May 2000; 74(9):4361-4376.

Butkiewicz, Nancy, et al., "Virus-Specific Cofactor Requirement and Chimeric Hepatitis C Virus/GB Virus B Nonstructural Protein 3" *Journal of Virology*, May 2000; 74(9):4291-4301.

Accola, Molly A., et al., "Efficient Particle Production by Minimal Gag Constructs Which Retain the Carboxy-Terminal Domain of Human Immunodeficiency Virus Type 1 Capsid-p2 and a Late Assembly Domain", *Journal of Virology*, Jun. 2000; 74(12):5395-5402.

Yuan, Bing, et al., "Infectivity of Moloney Murine Leukemia Virus Defective in Late Assembly Events Is Restored by Late Assembly Domains of Other Retroviruses", *Journal of Virology*, Aug. 2000; 74(16):7250-7260.

NCBI Entrez Protein Database Accession No. CAB92786, Sep. 20, 2000.

Jayakar, Himangi R., et al., "Mutations in the PPPY Motif of Vesicular Stomatitis Virus Matrix Protein Reduce Virus Budding by Inhibiting a Late Step in Virion Release", *Journal of Virology*, Nov. 2000; 74(21):9818-9827.

Strack, Bettina, et al., "A role for ubiquitin ligase recruitment in retrovirus release", *PNAS*, Nov. 21, 2000; 97(24):13063-13068.

Schubert, Ulrich, et al., "Proteasome Inhibition interferes with Gag polyprotein processing, release, and maturation of HIV-1 and HIV-2", *PNAS*, Nov. 21, 2000; 97(24):13057-13062.

Patnaik, Akash, et al., "Ubiquitin is part of the retrovirus budding machinery", *PNAS*, Nov. 21, 2000; 97(24):13069-13074.

Vogt, Volker M., "Ubiquitin in retrovirus assembly: Actor or bystander?", *PNAS*, Nov. 21, 2000; 97(24):12945-12947.

Harty, Ronald N., et al., "A PpxY motif within the VP40 protein of Ebola virus interacts physically and functionally with a ubiquitin ligase: Implications for filovirus budding", *PNAS*, Dec. 5, 2000; 97(25):13871-13876.

NCBI Entrez Protein Database Accession No. AAD17020, Jun. 1, 2001.

Verplank, Lynn, et al., "Tsg101, a homologue of ubiquitin-conjugating (E2) enzymes, binds the L domain in HIV type 1 Pr55Gag", *PNAS*, Jul. 3, 2001; 98(14):7724-7729.

Garrus, Jennifer E., et al., "Tsg101 and the Vacuolar Protein Sorting Pathway Are Essential for HIV-1 Budding", *Cell*, Oct. 5, 2001; 107:55-65.

Whittle, Peter J., et al., "Protein Structure-Based Drug Design", *Annu. Rev. Biophys. Biomol. Struct.*, 1994; 23:349-375.

Mhashilkar, Abner M., et al., "Inhibition of HIV-1 Tat-mediated LTR transactivation and HIV-1 infection by anti-Tat single chain intrabodies", *The EMBO Journal*, 1995; 14(7):1542-1551.

Huang, Mingjun, et al., "p6$^{Gag}$ Is Required for Particle Production from Full-Length Human Immunodeficiency Virus Type 1 Molecular Clones Expressing Protease", *Journal of Virology*, Nov. 1995; 69(11):6810-6818.

Rossi, John J., "Therapeutic applications of catalytic antisense RNAs (ribozymes)", *CIBA Foundation Symposium*, 1997; 209:195-204.

Levin, Reuven, et al., "Inhibition of Early and Late Events of the HIV-1 Replication Cycle by Cytoplasmic Fab Intrabodies against the Matrix Protein, p17", *Molecular Medicine*, Feb. 1997; 3(2):96-110.

Savarino, Andrea, et al., "The Biochemistry of Gene Therapy for AIDS", *Clin. Chem. Lab. Med.*, 1998; 36(4):205-210.

Verkhivker, Gennady M., "Towards understanding the mechanisms of molecular recognition by computer simulations of ligand-protein interactions", *Journal of Molecular Recognition*, 1999; 12:371-389.

Luban, Jeremy, "HIV-1 and Ebola virus: The gateway driver nabbed", *Nature Medicine*, Dec. 2001; 7(12):1278:1280.

Martin-Serrano, Juan, et al., "HIV-1 and Ebola virus encode small peptide motifs that recruit TSG101 to sites of particle assembly to facilitate egress", *Nature Medicine*, Dec. 2001; 7(12):1313-1319.

Demirov, Dimiter G., et al., "Overexpression of the N-Terminal domain of TSG101 inhibits HIV-1 budding by blocking late domain function", *PNAS*, Jan. 22, 2002; 99(2):955-960.

Supplementary European Search Report dated Feb. 11, 2005 (2 pages).

Sun et al., "Tumor Susceptibility Gene 101 Protein Represses Androgen Receptor Transactivation and Interacts with p300", *Cancer*, Aug. 15, 1999, 86(4):689-696.

VerPlank et al., Tsg101, a homologue of ubiquitin-conjugating (E2) enzymes, binds the L domain in HIV type 1 Pr55$^{Gag}$, *PNAS*, Jul. 3, 2001, 98(14):7724-7729.

* cited by examiner

TSG101-GAGP6 INTERACTION AND USE THEREOF

RELATED APPLICATIONS

This application claims priority to U.S. Provisional Patent Application Ser. No. 60/276,259 filed on Mar. 14, 2001, which is incorporated herein by reference.

FIELD OF THE INVENTION

The present invention generally relates to protein-protein interactions, particularly to protein-protein interaction between Tsg101 and HIV GAGp6 and methods of use thereof.

BACKGROUND OF THE INVENTION

The prolific output from numerous genomic sequencing efforts, including the Human Genome Project, is creating an ever-expanding foundation for large-scale study of protein function. Indeed, this emerging field of proteomics can appropriately be viewed as a bridge that connects DNA sequence information to the physiology and pathology of intact organisms. As such, proteomics—the large-scale study of protein function—will likely be starting point for the development of many future pharmaceuticals. The efficiency of drug development will therefore depend on the diversity and robustness of the methods used to elucidate protein function, i.e., the proteomic tools, that are available.

Several approaches are generally known in the art for studying protein function. One method is to analyze the DNA sequence of a particular gene and the amino acid sequence coded by the gene in the context of sequences of genes with known functions. Generally, similar functions can be predicted based on sequence homologies. This "homology method" has been widely used, and powerful computer programs have been designed to facilitate homology analysis. See, e.g., Altschul et al., *Nucleic Acids Res.*, 25:3389–3402 (1997). However, this method is useful only when the function of a homologous protein is known.

Another useful approach is to interfere with the expression of a particular gene in a cell or organism and examine the consequent phenotypic effects. For example, Fire et al., *Nature*, 391:806–811 (1998) disclose an "RNA interference" assay in which double-stranded RNA transcripts of a particular gene are injected into cells or organisms to determine the phenotypes caused by the exogenous RNA. Alternatively, transgenic technologies can be utilized to delete or "knock out" a particular gene in an organism and the effect of the gene knockout is determined. See e.g., Winzeler et al., *Science*, 285:901–906 (1999); Zambrowicz et al., *Nature*, 392:608–611 (1998). The phenotypic effects resulting from the disruption of expression of a particular gene can shed some light on the functions of the gene. However, the techniques involved are complex and the time required for a phenotype to appear can be long, especially in animals. In addition, in many cases disruption of a particular gene may not cause any detectable phenotypic effect.

Gene functions can also be uncovered by genetic linkage analysis. For example, genes responsible for certain diseases may be identified by positional cloning. Alternatively, gene function may be inferred by comparing genetic variations among individuals in a population and correlating particular phenotypes with the genetic variations. Such linkage analyses are powerful tools, particularly when genetic variations exist in a traceable population from which samples are readily obtainable. However, readily identifiable genetic diseases are rare and samples from a large population with genetic variations are not easily accessible. In addition, it is also possible that a gene identified in a linkage analysis does not contribute to the associated disease or symptom but rather is simply linked to unknown genetic variations that cause the phenotypic defects.

With the advance of bioinformatics and publication of the full genome sequence of many organisms, computational methods have also been developed to assign protein functions by comparative genome analysis. For example, Pellegrini et al., *Proc. Natl. Acad. Sci. USA* 96:4285–4288 (1999) discloses a method that constructs a "phylogenetic profile," which summarizes the presence or absence of a particular protein across a number of organisms as determined by analyzing the genome sequences of the organisms. A protein's function is predicted to be linked to another protein's function if the two proteins share the same phylogenetic profile. Another method, the Rosetta Stone method, is based on the theory that separate proteins in one organism are often expressed as separate domains of a fusion protein in another organism. Because the separate domains in the fusion protein are predictably associated with the same function, it can be reasonably predicted that the separate proteins are associated with same functions. Therefore, by discovering separate proteins corresponding to a fusion protein, i.e., the "Rosetta Stone sequence," functional linkage between proteins can be established. See Marcotte et al., *Science*, 285:751–753 (1999); Enright et al., *Nature*, 402:86–90 (1999). Another computational method is the "gene neighbor method." See Dandekar et al., *Trends Biochem. Sci.*, 23:324–328 (1998); Overbeek et al., *Proc. Natl. Acad. Sci. USA* 96:2896–2901 (1999). This method is based on the likelihood that if two genes are found to be neighbors in several different genomes, the proteins encoded by the genes share a common function.

While the methods described above are useful in analyzing protein functions, they are constrained by various practical limitations such as unavailability of suitable samples, inefficient assay procedures, and limited reliability. The computational methods are useful in linking proteins by function. However, they are only applicable to certain proteins, and the linkage maps established therewith are sketchy. That is, the maps lack specific information that describes how proteins function in relation to each other within the functional network. Indeed, none of the methods places the identified protein functions in the context of protein-protein interactions.

In contrast with the traditional view of protein function, which focuses on the action of a single protein molecule, a modern expanded view of protein function defines a protein as an element in an interaction network. See Eisenberg et al., *Nature*, 405:823–826 (2000). That is, a full understanding of the functions of a protein will require knowledge of not only the characteristics of the protein itself, but also its interactions or connections with other proteins in the same interacting network. In essence, protein-protein interactions form the basis of almost all biological processes, and each biological process is composed of a network of interacting proteins. For example, cellular structures such as cytoskeletons, nuclear pores, centrosomes, and kinetochores are formed by complex interactions among a multitude of proteins. Many enzymatic reactions are associated with large protein complexes formed by interactions among enzymes, protein substrates, and protein modulators. In addition, protein-protein interactions are also part of the mechanisms for signal transduction and other basic cellular functions such as DNA replication, transcription, and translation. For example, the complex transcription initiation process generally requires protein-protein interactions among numerous transcription factors, RNA polymerase, and other proteins. See e.g., Tjian and Maniatis, *Cell,* 77:5–8 (1994).

Because most proteins function through their interactions with other proteins, if a test protein interacts with a known protein, one can reasonably predict that the test protein is associated with the functions of the known protein, e.g., in the same cellular structure or same cellular process as the known protein. Thus, interaction partners can provide an immediate and reliable understanding towards the functions of the interacting proteins. By identifying interacting proteins, a better understanding of disease pathways and the cellular processes that result in diseases may be achieved, and important regulators and potential drug targets in disease pathways can be identified.

There has been much interest in protein-protein interactions in the field of proteomics. A number of biochemical approaches have been used to identify interacting proteins. These approaches generally employ the affinities between interacting proteins to isolate proteins in a bound state. Examples of such methods include coimmunoprecipitation and copurification, optionally combined with cross-linking to stabilize the binding. Identities of the isolated protein interacting partners can be characterized by, e.g., mass spectrometry. See e.g., Rout et al., *J. Cell. Biol.,* 148: 635–651 (2000); Houry et al., *Nature,* 402:147–154 (1999); Winter et al., *Curr. Biol.,* 7:517–529 (1997). A popular approach useful in large-scale screening is the phage display method, in which filamentous bacteriophage particles are made by recombinant DNA technologies to express a peptide or protein of interest fused to a capsid or coat protein of the bacteriophage. A whole library of peptides or proteins of interest can be expressed and a bait protein can be used to screening the library to identify peptides or proteins capable of binding to the bait protein. See e.g., U.S. Pat. Nos. 5,223,409; 5,403,484; 5,571,698; and 5,837,500. Notably, the phage display method only identifies those proteins capable of interacting in an in vitro environment, while the coimmunoprecipitation and copurification methods are not amenable to high throughput screening.

The yeast two-hybrid system is a genetic method that overcomes certain shortcomings of the above approaches. The yeast two-hybrid system has proven to be a powerful method for the discovery of specific protein interactions in vivo. See generally, Bartel and Fields, eds., *The Yeast Two-Hybrid System,* Oxford University Press, New York, N.Y., 1997. The yeast two-hybrid technique is based on the fact that the DNA-binding domain and the transcriptional activation domain of a transcriptional activator contained in different fusion proteins can still activate gene transcription when they are brought into proximity to each other. In a yeast two-hybrid system, two fusion proteins are expressed in yeast cells. One has a DNA-binding domain of a transcriptional activator fused to a test protein. The other, on the other hand, includes a transcriptional activating domain of the transcriptional activator fused to another test protein. If the two test proteins interact with each other in vivo, the two domains of the transcriptional activator are brought together reconstituting the transcriptional activator and activating a reporter gene controlled by the transcriptional activator. See, e.g., U.S. Pat. No. 5,283,173.

Because of its simplicity, efficiency and reliability, the yeast two-hybrid system has gained tremendous popularity in many areas of research. In addition, yeast cells are eukaryotic cells. The interactions between mammalian proteins detected in the yeast two-hybrid system typically are bona fide interactions that occur in mammalian cells under physiological conditions. As a matter of fact, numerous mammalian protein-protein interactions have been identified using the yeast two-hybrid system. The identified proteins have contributed significantly to the understanding of many signal transduction pathways and other biological processes. For example, the yeast two-hybrid system has been successfully employed in identifying a large number of novel mammalian cell cycle regulators that are important in complex cell cycle regulations. Using known proteins that are important in cell cycle regulation as baits, other proteins involved in cell cycle control were identified by virtue of their ability to interact with the baits. See generally, Hannon et al., in *The Yeast Two-Hybrid System,* Bartel and Fields, eds., pages 183–196, Oxford University Press, New York, N.Y., 1997. Examples of mammalian cell cycle regulators identified by the yeast two-hybrid system include CDK4/CDK6 inhibitors (e.g., p16, p15, p18 and p19), Rb family members (e.g., p130), Rb phosphatase (e.g., PP1-a2), Rb-binding transcription factors (e.g., E2F-4 and E2F-5), General CDK inhibitors (e.g., p21 and p27), CAK cyclin (e.g., cyclin H), and CDK Thr161 phosphatase (e.g., KAP and CDI1). See id at page 192. "[T]he two-hybrid approach promises to be a useful tool in our ongoing quest for new pieces of the cell cycle puzzle." See id at page 193.

The yeast two-hybrid system can be employed to identify proteins that interact with a specific known protein involved in a disease pathway, and thus provide valuable understandings of the disease mechanism. The identified proteins and the protein-protein interactions they participate are potential drug targets for use in selecting new drugs for treating the disease.

SUMMARY OF THE INVENTION

It has been discovered in the yeast two-hybrid system that human tumor susceptibility gene 101 ("Tsg101") interacts with HIV GAGp6. The specific interaction between such proteins suggests that Tsg101 and HIV GAGp6 are involved in HIV propagation in human cells, particularly HIV budding from the infected host cells. In addition, the interaction between Tsg101 and HIV GAGp6 can result in the formation of protein complexes both in vitro and in vivo that contain Tsg101 and HIV GAGp6. Particularly, the interaction between Tsg101 and HIV GAGp6 is essential for HIV budding from host cells. Thus, the protein complexes as well as Tsg101 can be used in screening assays to select compounds capable of modulating the functions and activities of Tsg101 and the protein complexes containing Tsg101 and HIV GAGp6. The identified compounds can be useful in inhibiting lentivirus propagation, particularly HIV propagation, and in treating HIV infection and AIDS.

Accordingly, in accordance with a first aspect of the present invention, isolated protein complexes are provided comprising Tsg101 and HIV GAGp6. In addition, homologues, derivatives, and fragments of Tsg101 and of HIV GAGp6 may also be used in forming protein complexes. In a specific embodiment, fragments of Tsg101 and HIV GAGp6 corresponding to the protein domains responsible for the interaction between Tsg101 and HIV GAGp6 are used in forming a protein complex of the present invention. In yet another embodiment, a protein complex is provided from a hybrid protein, which comprises Tsg101 or a homologue, derivative, or fragment thereof covalently linked, directly or through a linker, to HIV GAGp6 or a homologue, derivative, or fragment thereof.

The protein complexes can be prepared by isolation or purification from tissues and cells or produced by recombinant expression of their protein members. The protein complexes can be incorporated into a protein microchip or microarray, which are useful in large-scale high throughput screening assays involving the protein complexes.

In accordance with a second aspect of the invention, antibodies are provided which are immunoreactive with a protein complex of the present invention. In one embodiment, an antibody is selectively immunoreactive with a protein complex of the present invention. In another embodiment, a bifunctional antibody is provided which has two different antigen binding sites, each being specific to a different interacting protein member in a protein complex of the present invention. The antibodies of the present invention can take various forms including polyclonal antibodies, monoclonal antibodies, chimeric antibodies, antibody fragments such as Fv fragments, single-chain Fv fragments (scFv), Fab' fragments, and F(ab')$_2$ fragments. Preferably, the antibodies are partially or fully humanized antibodies. The antibodies of the present invention can be readily prepared using procedures generally known in the art. For example, recombinant libraries such as phage display libraries and ribosome display libraries may be used to screen for antibodies with desirable specificities. In addition, various mutagenesis techniques such as site-directed mutagenesis and PCR diversification may be used in combination with the screening assays.

The present invention also provides screening methods for selecting modulators of a protein complex formed between Tsg101 or a homologue, derivative or fragment thereof and HIV GAGp6 or a homologue, derivative or fragment thereof. Screening methods are also provided for selecting modulators of Tsg101. The compounds identified in the screening methods of the present invention can be used in studying the interaction between Tsg101 and HIV GAGp6 and understanding the mechanism of HIV viral propagation. The selected compounds may also be useful in preventing or ameliorating diseases or disorders such as HIV infection and AIDS.

Thus, test compounds may be screened in an in vitro binding assay to select compounds capable of binding a protein complex of the present invention or Tsg101. In addition, in vitro dissociation assays may also be employed to select compounds capable of dissociating the protein complexes identified in accordance with the present invention. An in vitro screening assay may also be used to select compounds that trigger or initiate the formation of, or stabilize, a protein complex of the present invention. In preferred embodiments, in vivo assays such as yeast two-hybrid assays and various derivatives thereof, preferably reverse two-hybrid assays, are utilized in selecting compounds that interfere with or disrupt protein-protein interactions between Tsg101 or a homologue, derivative or fragment thereof and HIV GAGp6 or a homologue, derivative or fragment thereof. In addition, systems such as yeast two-hybrid assays are also useful in selecting compounds capable of triggering or initiating, enhancing or stabilizing protein-protein interactions between Tsg101 or a homologue, derivative or fragment thereof and HIV GAGp6 or a homologue, derivative or fragment thereof.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

1. Definitions

Figure 1:
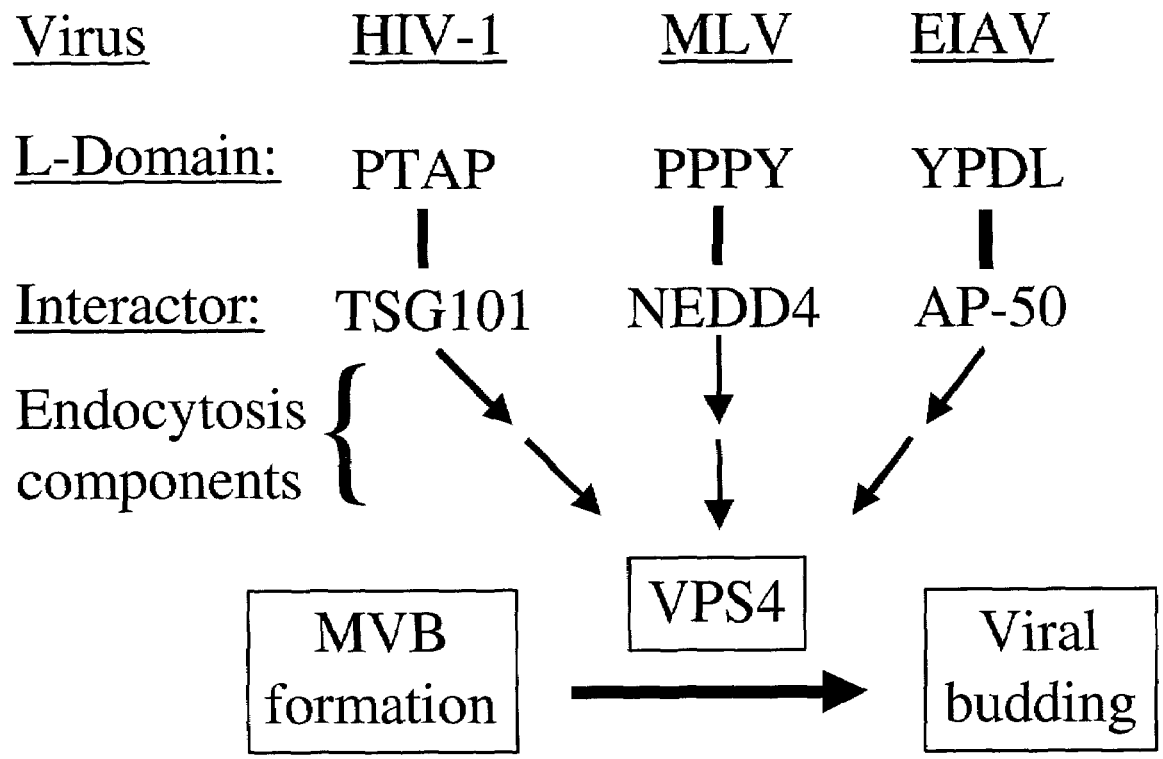
FIG. 1 is a diagram summarizing the pathways for the budding by viruses using different late domain motifs.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by genes may also be included in a polypeptide.

The term "protein fragment" as used herein means a polypeptide that represents a portion of a protein. When a protein fragment exhibits interactions with another protein or protein fragment, the two entities are said to interact through interaction domains that are contained within the entities.

As used herein, the term "interacting" or "interaction" means that two protein domains, fragments or complete proteins exhibit sufficient physical affinity to each other so as to bring the two "interacting" protein domains or proteins physically close to each other. An extreme case of interaction is the formation of a chemical bond that results in continual and stable proximity of the two domains. Interactions that are based solely on physical affinities, although usually more dynamic than chemically bonded interactions, can be equally effective in co-localizing two proteins. Examples of physical affinities and chemical bonds include but are not limited to, forces caused by electrical charge differences, hydrophobicity, hydrogen bonds, van der Waals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between antigen and antibody, ligand and receptor, enzyme and substrate, and the like.

An "interaction" between two protein domains, fragments or complete proteins can be determined by a number of methods. For example, an interaction can be determined by functional assays such as the two-hybrid systems. Protein-protein interactions can also be determined by various biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, *Microbiol. Rev.*, 59:94–123 (1995).

As used herein, the term "domain" means a functional portion, segment or region of a protein, or polypeptide. "Interaction domain" refers specifically to a portion, segment or region of a protein, polypeptide or protein fragment that is responsible for the physical affinity of that protein, protein fragment or isolated domain for another protein, protein fragment or isolated domain.

As used herein, the term "protein complex" means a composite unit that is a combination of two or more proteins formed by interaction between the proteins. Typically but not necessarily, a "protein complex" is formed by the binding of two or more proteins together through specific non-covalent binding affinities. However, covalent bonds may also be present between the interacting partners. For instance, the two interacting partners can be covalently crosslinked so that the protein complex becomes more stable.

The term "isolated protein complex" means a protein complex present in a composition or environment that is different from that found in nature in its native or original cellular or body environment. Preferably, an "isolated protein complex" is separated from at least 50%, more preferably at least 75%, most preferably at least 90% of other naturally co-existing cellular or tissue components. Thus, an "isolated protein complex" may also be a naturally existing protein complex in an artificial preparation or a non-native host cell. An "isolated protein complex" may also be a "purified protein complex", that is, a substantially purified form in a substantially homogenous preparation substantially free of other cellular components, other polypeptides, viral materials, or culture medium, or when the protein components in the protein complex are chemically synthesized, chemical precursors or by-products associated with the chemical synthesis. A "purified protein complex" typically means a preparation containing preferably at least 75%, more preferably at least 85%, and most preferably at least 95% a particular protein complex. A "purified protein complex" may be obtained from natural or recombinant host cells or other body samples by standard purification techniques, or by chemical synthesis.

The terms "hybrid protein," "hybrid polypeptide," "hybrid peptide," "fusion protein," "fusion polypeptide," and "fusion peptide" are used herein interchangeably to mean a non-naturally occurring protein having a specified polypeptide molecule covalently linked to one or more polypeptide molecules which do not naturally link to the specified polypeptide. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

As used herein, the term "homologue," when used in connection with a first native protein or fragment thereof that is discovered, according to the present invention, to interact with a second native protein or fragment thereof, means a polypeptide that exhibits an amino acid sequence homology and/or structural resemblance to the first native interacting protein, or to one of the interacting domains of the first native protein such that it is capable of interacting with the second native protein. Typically, a protein homologue of a native protein may have an amino acid sequence that is at least 50%, preferably at least 75%, more preferably at least 80%, 85%, 86%, 87%, 88% or 89%, even more preferably at least 90%, 91%, 92%, 93% or 94%, and most preferably 95%, 96%, 97%, 98% or 99% identical to the native protein. Examples of homologues may be the ortholog proteins of other species including animals, plants, yeast, bacteria, and the like. Homologues may also be selected by, e.g., mutagenesis in a native protein. For example, homologues may be identified by site-specific mutagenesis in combination with assays for detecting protein-protein interactions, e.g., the yeast two-hybrid system described below, as will be apparent to skilled artisans apprised of the present invention.

For purposes of comparing two different nucleic acid or polypeptide sequences, one sequence (test sequence) may be described to be a specific "percent identical to" another sequence (reference sequence) in the present disclosure. In this respect, when the length of the test sequence is less than 90% of the length of the reference sequence, the percentage identity is determined by the algorithm of Myers and Miller, Bull. Math. Bid., 51:5–37 (1989) and Myers and Miller, *Comput. Appl. Biosci.*, 4(1): 11–7 (1988). Specifically, the identity is determined by the ALIGN program, which is available at IGH, Montpellier, FRANCE. A modified form of the ALIGN program may also be used. Typically the default parameters can be used. Preferably, a gap length penalty of 12 and a gap penalty of 4 can be used.

Where the length of the test sequence is at least 90% of the length of the reference sequence, the percentage identity is determined by the algorithm of Karlin and Altschul, *Proc. Natl. A cad. Sci. USA,* 90:5873–77 (1993), which is incorporated into the various BLAST programs. Specifically, the percentage identity is determined by the "BLAST 2 Sequences" tool, which is available at NCBI's website. See Tatusova and Madden, *FEMS Microbiol. Lett.,* 174(2):247–50 (1999). For pairwise DNA-DNA comparison, the BLASTN 2.1.2 program is used with default parameters (Match: 1; Mismatch: 2; Open gap: 5 penalties; extension gap: 2 penalties; gap x_dropoff: 50; expect: 10; and word size: 11, with filter). For pairwise protein-protein sequence comparison, the BLASTP 2.1.2 program is employed using default parameters (Matrix: BLOSUM62; gap open: 11; gap extension: 1; x_dropoff: 15; expect: 10.0; and wordsize: 3, with filter).

The term "derivative," when used in connection with a first native protein (or fragment thereof) that is discovered, according to the present invention, to interact with a second native protein (or fragment thereof), means a modified form of the first native protein prepared by modifying the side chain groups of the first native protein without changing the amino acid sequence of the first native protein. The modified form, i.e., the derivative should be capable of interacting with the second native protein. Examples of modified forms include glycosylated forms, phosphorylated forms, myristylated forms, ribosylated forms, ubiquitinated forms, and the like. Derivatives also include hybrid or fusion proteins containing a native protein or a fragment thereof. Derivatives can be prepared using any known techniques and tested for their interaction with the second native protein.

The term "antibody" as used herein encompasses both monoclonal and polyclonal antibodies that fall within any antibody classes, e.g., IgG, IgM, IgA, or derivatives thereof. The term "antibody" also includes antibody fragments including, but not limited to, Fab, F(ab')$_2$, and conjugates of such fragments, and single-chain antibodies comprising an antigen recognition epitope. In addition, the term "antibody" also means humanized antibodies, including partially or fully humanized antibodies. An antibody may be obtained from an animal, or from a hybridoma cell line producing a monoclonal antibody, or obtained from cells or libraries recombinantly expressing a gene encoding a particular antibody.

The term "selectively immunoreactive" as used herein means that an antibody is reactive thus binds to a specific protein or protein complex, but not other similar proteins or fragments or components thereof.

The term "compound" as used herein encompasses all types of organic or inorganic molecules, including but not limited to proteins, peptides, polysaccharides, lipids, nucleic acids, small organic molecules, inorganic compounds, and derivatives thereof.

Unless otherwise specified, the term "Tsg101" as used herein means human Tsg101 protein. Unless otherwise specified, the term "HIV GAGp6" as used herein means HIV GAGp6 protein.

2. Protein Complexes

Novel protein-protein interactions have been discovered and confirmed using yeast two-hybrid systems. In particular, it has been discovered that Tsg101 interacts with HIV GAGp6. Binding regions of Tsg101 and HIV GAGp6 discovered in yeast two-hybrid systems are summarized in Table 1. The GenBank accession numbers for the gene sequences and amino acid sequences of Tsg101 and HIV GAGp6 are noted in Table 1 below.

TABLE 1

Binding Regions of HIV Gag and Tsg101

| Bait | | | Prey | | |
|---|---|---|---|---|---|
| | AA Coordinates | | | AA Coordinates | |
| Bait Protein | Start | End | Prey Protein | Start | End |
| HIV Gag (GenBank Accession No. AF324493) | 449 | 500 | Tumor Suppressor Gene 101 (Tsg101) (GenBank Accession No. U82130) | 7 | 390 |

In addition, a number of cellular protein interactors for Tsg101 have also been identified using yeast two-hybrid systems. These interactions are summarized in Table 2 below.

TABLE 2

Cellular Proteins That Interact with Tsg101 Protein

| Bait Protein | | | Prey Protein | | | |
|---|---|---|---|---|---|---|
| | Bait AA Sequence | | | | Prey AA Sequence | |
| | Begin | End | Protein | GB Access No. | Begin | End |
| Tumor Supressor Tsg101 (GenBank Accession No.: U82130) | 240 | 391 | desmoplakin I | J05211 | 1501 | 1589 |
| | 240 | 391 | desmoplakin I | J05211 | 1438 | 1609 |
| | 1 | 157 | keratin 5 | D50666 | 9 | 171 |
| | 240 | 391 | keratin 5 | D50666 | 324 | 446 |
| | 240 | 391 | keratin 5 | D50666 | 282 | 448 |
| | 240 | 391 | keratin 5 | D50666 | 379 | 452 |
| | 240 | 391 | keratin 5 | D50666 | 335 | 473 |
| | 240 | 391 | keratin 5 | D50666 | 349 | 475 |
| | 240 | 391 | keratin 5 | D50666 | 384 | 475 |
| | 240 | 391 | keratin 5 | D50666 | 347 | 485 |
| | 140 | 270 | synexin | J04543 | 22 | 329 |
| | 240 | 391 | Golgi autoantigen | L06147 | 23 | 189 |
| | 240 | 391 | restin | M97501 | 770 | 898 |
| | 240 | 391 | restin | M97501 | 660 | 903 |
| | 240 | 391 | keratin 8 | X98614 | 293 | 394 |
| | 240 | 391 | keratin 8 | X98614 | 147 | 406 |
| | 240 | 391 | GTPase-activating protein 1 | D29640 | 1406 | 1547 |
| | 240 | 391 | GTPase-activating protein 1 | D29640 | 1404 | 1553 |
| | 240 | 391 | GTPase-activating protein 1 | D29640 | 1299 | 1555 |
| | 240 | 391 | GTPase-activating protein 1 | D29640 | 1439 | 1565 |
| | 240 | 391 | GTPase-activating protein 1 | D29640 | 1413 | 1567 |
| | 240 | 391 | GTPase-activating protein 1 | D29640 | 1439 | 1567 |
| | 240 | 391 | GTPase-activating protein 1 | D29640 | 1463 | 1568 |

TABLE 2-continued

Cellular Proteins That Interact with Tsg101 Protein

| Bait Protein | Bait AA Sequence | | Prey Protein | | Prey AA Sequence | |
|---|---|---|---|---|---|---|
| | Begin | End | Protein | GB Access No. | Begin | End |
| Tumor Supressor Tsg101 (GenBank Accession No.: U82130) | 240 | 391 | GTPase-activating protein 1 | D29640 | 1308 | 1606 |
| | 240 | 391 | GTPase-activating protein 1 | D29640 | 1392 | 1657 |
| | 240 | 391 | GTPase-activating protein 1 | D29640 | 1419 | 1657 |
| | 240 | 391 | endosome associated protein 1 | X78998 | 872 | 1039 |
| | 240 | 391 | 88-kDa Golgi protein | AB020662 | 128 | 237 |
| | 240 | 391 | 88-kDa Golgi protein | AB020662 | 186 | 273 |
| | 240 | 391 | 88-kDa Golgi protein | AB020662 | 148 | 287 |
| | 240 | 391 | 88-kDa Golgi protein | AB020662 | 98 | 402 |
| | 240 | 391 | 88-kDa Golgi protein | AB020662 | 118 | 487 |
| | 240 | 391 | centromere protein F | U19769 | 104 | 332 |
| | 240 | 391 | centromere protein F | U19769 | 190 | 420 |
| | 240 | 391 | keratin 6C | L42601 | 373 | 444 |
| | 240 | 391 | serum deprivation response | NM_004657 | 75 | 258 |
| | 240 | 391 | mitotic spindle coiled-coil related protein | NM_006461 | 668 | 895 |
| | 240 | 391 | mitotic spindle coiled-coil related protein | NM_006461 | 723 | 1012 |
| | 240 | 391 | mitotic spindle coiled-coil related protein | NM_006461 | 942 | 1021 |
| | 240 | 391 | mitotic spindle coiled-coil related protein | NM_006461 | 701 | 1082 |
| | 147 | 391 | golgi autoantigen | NM_005113 | 198 | 501 |
| | 231 | 391 | Golgi autoantigen (Golgin-84) | NM_005113 | 198 | 501 |
| | 12 | 326 | Golgi autoantigen (Golgin-84) | NM_005113 | 198 | 497 |
| | 12 | 326 | Golgi autoantigen (Golgin-84) | NM_005113 | 198 | 501 |
| | 231 | 391 | Golgin-67 | AF163441 | 68 | 228 |
| | 240 | 391 | Golgin-67 | AF163441 | 123 | 226 |
| | 240 | 391 | Golgin-67 | AF163441 | 135 | 226 |
| | 240 | 391 | Golgin-67 | AF163441 | 1 | 231 |
| | 140 | 270 | hypothetical protein FLJ10540 | NM_018131 | 1 | 74 |
| | 50 | 391 | hypothetical protein FLJ10540 | NM_018131 | 1 | 110 |
| | 140 | 270 | hypothetical protein FLJ10540 | NM_018131 | 1 | 115 |
| | 50 | 391 | hypothetical protein FLJ10540 | NM_018131 | 1 | 117 |
| | 140 | 270 | hypothetical protein FLJ10540 | NM_018131 | 1 | 120 |
| | 140 | 270 | hypothetical protein FLJ10540 | NM_018131 | 2 | 132 |
| | 140 | 270 | hypothetical protein FLJ10540 | NM_018131 | 1 | 140 |
| | 50 | 391 | hypothetical protein FLJ10540 | NM_018131 | 1 | 231 |
| | 50 | 391 | hypothetical protein FLJ10540 | NM_018131 | 115 | 231 |
| | 147 | 391 | VPS28 protein | NM_016208 | 10 | 221 |
| | 147 | 391 | VPS28 protein | NM_016208 | 27 | 221 |
| | 231 | 391 | VPS28 protein | NM_016208 | 9 | 211 |
| | 231 | 391 | VPS28 protein | NM_016208 | 10 | 221 |

TABLE 2-continued

Cellular Proteins That Interact with Tsg101 Protein

| Bait Protein | | | Prey Protein | | | |
|---|---|---|---|---|---|---|
| | Bait AA Sequence | | | GB Access | Prey AA Sequence | |
| | Begin | End | Protein | No. | Begin | End |
| | 265 | 391 | VPS28 protein | NM_016208 | 10 | 221 |
| | 317 | 391 | VPS28 protein | NM_016208 | 10 | 221 |
| | 240 | 391 | hook2 protein | NM_013312 | 290 | 555 |
| | 240 | 391 | hook2 protein | NM_013312 | 201 | 559 |
| | 240 | 391 | intersectin 1 | NM_003024 | 436 | 547 |
| | 240 | 391 | intersectin 1 | NM_003024 | 437 | 584 |
| | 240 | 391 | intersectin 1 | NM_003024 | 387 | 611 |
| | 240 | 391 | intersectin 1 | NM_003024 | 210 | 633 |
| | 240 | 391 | pallid | AF080470 | 21 | 172 |
| | 240 | 391 | catenin | U96136 | 684 | 1148 |
| Tumor Supressor Tsg101 (GenBank Accession No.: U82130) | 231 | 391 | kinectin | Z22551 | 851 | 1110 |
| | 231 | 391 | kinectin | Z22551 | 854 | 1110 |
| | 231 | 391 | kinectin | Z22551 | 851 | 1113 |
| | 1 | 274 | A kinase (PRKA) anchor protein 13 (AKAP13) | M90360 | 324 | 483 |
| | 1 | 274 | A kinase (PRKA) anchor protein 13 (AKAP13) | M90360 | 324 | 587 |
| | 1 | 274 | A kinase (PRKA) anchor protein 13 (AKAP13) | M90360 | 324 | 589 |
| | 231 | 391 | Tropomyosin TM30 p1 (TPM4) | X05276 | 79 | 142 |
| | 231 | 391 | Tropomyosin TM30 p1 (TPM4) | X05276 | 91 | 142 |
| | 231 | 391 | FK506-binding protein homolog KIAA0674 | AB014574 | 770 | 880 |
| | 12 | 326 | FK506-binding protein homolog KIAA0674 | AB014574 | 770 | 880 |
| | 265 | 391 | P87/89 motor protein | D21094 | 152 | 335 |
| | 317 | 391 | Amplified in osteosarcoma-9 (OS-9) | U41635 | 171 | 350 |
| | 317 | 391 | Amplified in osteosarcoma-9 (OS-9) | U41635 | 213 | 503 |
| | 231 | 391 | Rho-associated (ROCK1) | U43195 | 462 | 617 |
| | 231 | 391 | Cytoplasmic linker 2 (CYLN2) | NM_003388 | 607 | 947 |
| | 12 | 326 | Plectin (PLEC1(4574)) | U53204 | 1325 | 1504 |
| | 12 | 326 | Plectin (PLEC1(4574)) | U53204 | 1328 | 1504 |
| | 265 | 391 | Death associated protein 5 (DAP5) | X89713 | 16 | 157 |
| | 265 | 391 | Guanine nucleotide regulatory factor GEF-H1 (GEF-H1) | U72206 | 667 | 895 |
| | 12 | 326 | Accessory proteins BAP31/BAP29 (BAP31) | NM_005745 | 184 | 246 |
| | 231 | 391 | Zinc finger protein 231 (ZNF231) | AF052224 | 2308 | 2438 |
| | 231 | 391 | Chromosome-associated polypeptide HCAP (HCAP) | AF020043 | 208 | 300 |
| | 265 | 391 | Chromosome-associated polypeptide HCAP (HCAP) | AF020043 | 119 | 353 |
| | 265 | 391 | Protein kinase C and casein kinase substrate (PACSIN2) | AF128536 | 174 | 367 |

TABLE 2-continued

Cellular Proteins That Interact with Tsg101 Protein

| Bait Protein | | | Prey Protein | | |
|---|---|---|---|---|---|
| Bait AA Sequence | | | | Prey AA Sequence | |
| Begin | End | Protein | GB Access No. | Begin | End |
| 12 | 326 | PIBF1 | Y09631 | 392 | 758 |
| 1 | 274 | Actinin (ACTN4) | NM_004924 | 425 | 884 |
| 231 | 391 | Growth arrest-specific 7 (GAS7B) | NM_005890 | 69 | 249 |
| 231 | 391 | Growth arrest-specific 7 (GAS7B) | NM_005890 | 70 | 278 |
| 231 | 391 | Growth arrest-specific 7 (GAS7B) | NM_005890 | 66 | 301 |

2.1. Tsg101 is Involved in Endocytosis, Vesicle Trafficking and VPS Pathway

As shown in Table 2 above, the inventors of the present invention identified a large number of protein interactors of Tsg101, many of which are known to be involved in intracellular vesicle trafficking and vacuolar protein sorting.

2.1.1. Human Tsg101 Interacts with Human VPS28

In accordance with the present invention, C-terminal fragments of Tsg101 interacted with VPS28 in two different searches. One search of a hippocampal library utilized a Tsg101 bait fragment consisting of residues 147–391, while the other search of a breast and prostate cancer library utilized a shorter C-terminal fragment consisting of amino acid residues 240–391. Both Tsg101 fragments contain an alpha-helical region, and the longer fragment contained an overlapping coiled coil region as well. Both Tsg101 fragments also interacted with VPS28 via residues 27–221. In addition, VPS28 residues 10–221 were also isolated as a prey using the Tsg101 bait fragment amino acids. VPS28 is a class E protein involved in endocytosis. It consists of 221 amino acids and plays a role in the formation of multivesicular bodies and endosomal sorting. Rieder et al., *Mol. Biol. Cell*, 7(6):985–99 (1996). Mutations in VPS28 result in defects in endocytic traffic destined for the vacuole. Although Tsg101 and VPS28 are predominantly cytosolic, both proteins are recruited to endosomal vacuoles when a dominant-negative mutant VPS4 is expressed. Thus, both Tsg101 and VPS28 may be involved in endosomal sorting by functioning together in a multiprotein complex.

2.1.2. Tsg101 Interacts with a GTPase-Activating Protein (IQGAP1)

A C-terminal fragment of Tsg101 consisting of amino acid residues 240–391 was used in two different searches of a breast and prostate cancer library. This Tsg101 fragment, which contains most of an alpha-helical region, interacted with an IQ motif-containing GTPase-activating protein (IQ-GAP). IQGAP, a protein of 1657 amino acids, is expressed in many tissues including placenta, lung, and kidney. It contains several motifs including a Ras-related GTPase-activating (RasGAP) domain, a calponin homology domain, and four IQ motifs (named for the presence of tandem isoleucine and glutamine residues), which are known to modulate binding with subsequently cloned its cDNA. Recombinant IQGAP bound to activated Cdc42 and Rac and inhibited their GTPase activity while the C-terminal domain IQGAP was shown to inhibit the GTPase activity of Cdc42. Hart et al., *EMBO J.*, 15(12):2997–3005 (1996). IQGAP has also been shown to bind to actin, calmodulin, E-cadherin and beta-catenin. Li et al., *J. Biol. Chem.*, 274(53):37885–92 (1999); Fukata et al., *J. Biol. Chem.*, 274(37):26044–50 (1999). It may thus serve as a scaffolding protein and provide a link between calcium/calmodulin and Cdc42 signaling as well as with cell adhesion and the actin cytoskeleton. Ho et al., *J. Biol. Chem.*, 274(1):464–70 (1999). Interestingly, the small GTPases Cdc42 and rac, both of which associate with Tsg101, appear to be involved in endocytosis. See Malecz et al., *Curr. Biol.*, 10(21): 1383–6 (2000). With its multiple domains, its association with the actin cytoskeleton, and its RasGAP-like domain, IQGAP could be a good candidate for a regulator of endocytic trafficking.

2.1.3. Tsg101 Binds to Hook2 Protein

A C-terminal fragment of Tsg101 consisting of amino acid residues 240–390 was used in searches of a breast and prostate cancer library. This Tsg101 fragment, which contains most of an alpha-helical region, interacted with Hook2 (via amino acids 132–428). Hook was originally identified in Drosophila as a protein involved with endocytic trafficking. Kramer and Phistry, *J. Cell Biol.*, 133(6):1205–15 (1996). The gene encoding Hook2 (719 amino acids) was identified from sequence-homology searches of EST databases as having significant homology to the Drosophila hook gene. Kramer and Phistry, *Genetics*, 151(2):675–84 (1999). The Hook2 protein can be alternatively spliced, yielding a protein lacking amino acids 173–522. All Hook proteins contain two coiled coil regions in the central portion of the protein and a conserved 125 amino acid N-terminal domain of unknown function. Immunohistochemical studies showed that Hook localizes to endocytic vesicles and large vacuoles, implicating Hook in late endocytic trafficking. In hook mutants, cells lack mature MVBs and have an overabundance of late endosomes or lysosomes, indicating that Hook may stabilize mature MVBs and negatively regulate transport to late endosomes perhaps by inhibiting the fusion of MVBs to late endosomes. Sunio et al., *Mol. Biol. Cell.*, 10(4):847–59 (1999). The Tsg101 and Hook proteins appear to be prime candidates for regulating fusion at the MVB and endosome stages. The fact that they interact lends further support to this theory.

2.1.4. Tsg101 Interacts with Intersectin 1

A C-terminal fragment of Tsg101 consisting of amino acid residues 240–391 was used in two different searches of a breast and prostate cancer library. This Tsg101 fragment, which contains most of an alpha-helical region, interacted with a number of different fragments of Intersectin1 within the amino acids 201–633 region as indicated in Table I. Northern analysis showed that intersectin mRNA is widely expressed, but most highly in brain, heart, and skeletal muscle. Intersectin 1 is a protein consisting of 1721 amino acids that contains two N-terminal EH domains, a central coiled coil domain and five C-terminal SH3 domains. The regions interacting with Tsg101 correspond to more C-terminal EH domain and more N-terminal coiled coil domain. It has been found that Intersectin 1 binds in vivo to Eps15. Sengar et al, *EMBO J.*, 18(5):1159–71 (1999). The EH domain of Intersectin 1 binds to Epsin whereas its SH3 domains bind to dynamin. Eps15 is an essential component of the early endocytic pathway that is localized to the neck of clathrin-coated pits. Benmerah et al., *J. Cell Biol.*, 140(5): 1055–62 (1998). Dynamin is a GTPase which presumably functions to sever forming vesicles from the plasma membrane and is essential for receptor-mediated endocytosis. Epsin binds to clathrin and regulates receptor-mediated endocytosis. The interaction between Intersectin 1 and Eps15 appears to function as a scaffold which links dynamin, epsin, and other endocytic pathway components. The interaction between Tsg101 and Intersectin 1 suggests that Tsg101 may play a role in budding of membrane particles in various stages of endocytosis.

2.1.5. Tsg101 Interacts with GEF-H1

A search of a brain library with the tumor suppressor protein Tsg101 identified GEF-H1 as an interactor. GEF-H1 is an 894 amino acid protein identified by homology to guanine nucleotide exchange factors (GEFs) in a screen of a HeLa cell cDNA library. Ren et al., *J Biol Chem*, 273(52): 34954–60 (1998). GEF-H1 contains a Dbl-type GEF domain in tandem with a pleckstrin homology domain, a motif typically responsible for protein or lipid/membrane interaction. GEF-H1 binds Rac and Rho (known regulators of the cytoskeleton) and stimulates guanine nucleotide exchange of these GTPases, but GEF-H1 is inactive towards Cdc42, Ras, or other small GTPases. GEF-H1 also contains a C-terminal coiled-coil domain; immunofluorescence experiments reveal that this domain is responsible for colocalization of GEF-H1 with microtubules. Overexpression of GEF-H1 in COS-7 cells induces membrane ruffles. Together, these findings suggest that GEF-H1 may have a direct role in activating Rac and/or Rho and may localize these GTPases to microtubules, thereby coordinating cytoskeletal reorganization.

2.1.6. Tsg101 Interacts with the Protein Kinase ROCK1

A search of a macrophage library with the tumor suppressor protein Tsg101identified the Rho-associated coiled coil-containing kinase ROCK1 as an interactor. ROCK1, also known as ROK or p160, is a 1354 amino acid Ser/Thr-kinase that is activated by the small GTPase Rho, a known cytoskeletal regulator. Fujisawa et al., *J Biol Chem* 20;271(38): 23022–8 (1996); Leung et al., *Mol. Cell Biol.*, 16(10): 5313–27 (1996). Activation of ROCKI by Rho results in phosphorylation of LIM kinase, which in turn phosphorylates cofilin and inhibits its actin-depolymerizing activity. Maekawa et al., *Science* 285(5429):895–8 (1999). ROCK1 activity also results in phosphorylation of myosin light chain (MLC) and ERM (ezrin/radixin/moesin) proteins, which in turn mediate cytoskeletal responses. Tran et al., *EMBO J*, 19(17):4565–76 (2000); Kosako et al., *Oncogene*, 19(52): 6059–64 (2000); Takaishi et al., *Genes Cells*, 5(11):929–936 (2000). The effect of ROCK1 on MLC phosphorylation appears to be both indirect (via inhibition of MLC phosphatase and/or activiation of MLC kinase) and direct. Tatsukawa et al., *J. Cell Biol.*, 150(4):797–806 (2000); Kosako et al., *Oncogene*, 19(52): 6059–64 (2000). Substantial evidence supports roles for ROCK1 in processes such as formation of stress fibers, axonal outgrowth, smooth muscle contraction, cell motility, tumor cell invasion, and cytokinesis. See references above; Watanabe et al., *Nat. Cell Biol.*, 1(2):E31–3 (1999); Bito et al., *Neuron*, 26(2):431–41 (2000). ROCK1 has also implicated in intracellular lysosome trafficking by controlling microtubule organization. Nishimura et al., *Cell Tissue Res.*, 301(3):341–51 (2000). In these studies, ROCK1 activity was shown to be both necessary and sufficient for the formation of apoptotic membrane blebs (a process dependent on MLC phosphorylation) and for relocalization of fragmented genomic DNA to these blebs. Interestingly, a ROCK1-specific inhibitor has been identified; this compound, designated Y-27632 [(+)-(R)-trans-4-(1-aminoethyl)-N-(4-pyridyl) cyclohexanecarboxamide], is commercially-available from Tocris and is highly selective for ROCK1. This compound has been used in many of the studies cited above to inhibit ROCK1-dependent processes in various cell lines. The ROCK1 protein contains an N-terminal protein kinase domain, a large central coiled-coil domain, a leucine zipper (which mediates interaction with RhoA), and a C-terminal pleckstrin homology domain (protein and/or membrane/lipid interaction motif). Two prey constructs encoding amino acids 462–617 of ROCK1 were isolated according to the present invention; this region corresponds to part of the central coiled-coil motif. Analysis of homologous ESTs indicates that ROCK1 is expressed in a wide variety of tissues.

The known functions of ROCK1 in controlling the cytoskeleton, vesicular trafficking, and membrane blebbing are intriguing in light of the proposed roles for Tsg101 in viral assembly. The interaction of Tsg101 with ROCK1 suggests ROCK1 may be targeted to sites of viral budding, where it may recruit and activate proteins involved in the final stages of this process.

2.1.7. Tsg101 interacts with PACSIN2

A search of a macrophage library with the tumor suppressor protein Tsg101identified PACSIN2 as an interactor. PACSIN2 (which stands for PKC and casein kinase substrate in neurons 2) is a 486 amino acid protein isolated by its similarity (primary sequence and domain organization) to PACSIN1, a protein that is upregulated during neuronal differentiation and is phosphorylated by both PKC and casein kinase II. Ritter et al., *FEBS Lett* 454(3):356–62 (1999). Immunofluorescence microscopy of transfected NIH3T3 fibroblasts reveals a broad, vesicle-like PACSIN2 distribution pattern, suggesting a role in vesicular trafficking and/or the regulation of the actin cytoskeleton. In support of this, PACSIN2 is closely related (~90% amino acid identity) to rat syndapin II proteins, which are involved in receptor-mediated endocytosis and actin cytoskeleton reorganization. Qualmann and Kelly, *J Cell Biol*, 148(5): 1047–62 (2000). PACSIN2 is a 486 amino acid protein that contains an N-terminal FCH domain, which is found in proteins such as CIP4, an intermediate protein between Cdc42 kinase and cytoskeletal proteins, and Cdc15, a protein kinase involved in regulating actin at mitosis. PACSIN2 also contains a C-terminal SH3 domain, suggesting interaction with certain signaling proteins. EST analysis suggests expression of PACSIN2 in a wide variety of tissues.

2.1.8. Tsg101 Interacts with the Integral Membrane Protein Golgin-84

A search of a spleen library with the tumor suppressor protein Tsg101 identified Golgin-84 as an interactor. Golgin-84 is a 731 amino acid protein that was originally identified in a yeast two-hybrid search using the peripheral Golgi phosphatidylinositol phosphatase OCRL1 as bait. Bascom et al., *J. Biol. Chem.*, 274(5):2953–62 (1999). Golgin-84 is an integral membrane protein with a single transmembrane domain located near its C-terminus. In addition, Golgin-84 contains a large central coiled-coil motif. In vitro, the protein inserts post-translationally into microsomal membranes with an N-cytoplasmic and C-lumen orientation. Crosslinking experiments indicate that Golgin-84 is able to form homodimers, presumably via the large coiled-coil motif. Interestingly, when fused to the RET tyrosine kinase domain, this coiled-coil motif of Golgin-84 activates RET and forms the RET-II oncogene. Structurally, Golgin-84 is similar to giantin, which is involved in tethering coatamer complex I vesicles to the Golgi, suggesting that Golgin-84 may perform a similar tethering function. Expression studies and analysis of homologous ESTs indicate ubiquitous expression of Golgin-84.

2.1.9. Tsg101 Interacts with the Integral Membrane Protein Golgin-67

A search of a spleen library with the tumor suppressor protein Tsg101 identified golgin-67 as an interactor. Golgin-67 was fortuitously identified in searches of a T-cell expression library with antibodies against the mitotic target of Src, Sam68. Jakymiw et al., *J. Biol. Chem.*, 275(6):4137–44 (2000). Golgin-67 was also identified as an autoimmune antigen in various systemic rheumatic diseases. Eystathioy et al., *J. Autoimmun.*, 14(2):179–87 (2000). The 460 amino acid golgin-67 protein is structurally similar to golgin-84; both contain C-terminal transmembrane domains and large central coiled-coil regions. Cytological analysis demonstrates that golgin-67 is localized to the Golgi complex, and the transmembrane domain is necessary for localization to the Golgi.

2.1.10. Tsg101 Interacts with Kinectin

A yeast two-hybrid search of a brain library with the tumor suppressor protein Tsg101 identified kinectin as an interactor. Kinectin is a large (1,356 amino acid) integral ER membrane protein that contains an N-terminal transmembrane domain and C-terminal coiled-coil and leucine zipper motifs. Futterer et al., *Mol. Biol. Cell*, 6(2):161–70 (1995); Yu et al., *Mol. Biol. Cell*, 6(2):171–83 (1995). Antibodies against kinectin reveal a perinuclear, ER-like protein distribution. In vitro, kinectin is able to bind kinesin, a microtubule-associated ATP-dependent motor protein involved in vesicular transport along microtubules, and kinectin has been proposed to function as a receptor for kinesin on the surface of certain organelles. The C-terminal region of kinectin is responsible for interaction with kinesin. Ong et al., *J. Biol. Chem.*, 275(42):32854–60 (2000). Interaction of these proteins enhances the microtubule-stimulated ATPase activity of kinesin, and overexpression of the kinesin-binding domain of kinectin inhibits kinesin-dependent organelle motility in vivo, supporting a role for kinectin in vesicular transport. Kinectin has been shown to be a proteolytic target of caspases during apoptosis (Machleidt et al., *FEBS Lett.*, 436(1):51–4 (1998)), suggesting a role in mediating programmed cell death. Kinectin is also a translocation partner of the RET tyrosine kinase in certain thyroid carcinomas, resulting in a constitutively active form of RET. Salassidis et al., *Cancer Res.*, 60(11):2786–9 (2000). This is potentially interesting, in light of the observation that fusions between RET and another protein thought to be involved in vesicular transport, Golgin-84, also result in activation of RET. Bascom et al., *J. Biol. Chem.*, 274(5):2953–62 (1999). Finally, kinectin has been shown in the literature to interact with the GTP-bound forms (but not the GDP-bound forms) of various small Rho-family GTPases involved in cytoskeletal regulation, including RhoA, Rac1, and Cdc42. Hotta et al., *Biochem Biophys Res Commun* 225(1):69–74 (1996). This observation provides further links between Tsg101 and proteins involved in regulating the cytoskeleton. Three prey clones corresponding to kinectin were isolated; these encode similar, but distinct, fragments of the protein that overlap the region of kinectin responsible for interaction with kinesin.

2.1.11. Tsg101 Interacts with CYLN2

A search of a brain library with the tumor suppressor protein Tsg101 identified the cytoplasmic linker protein CYLN2 (also known as CLIP-115, for cytoplasmic linker protein-115 kD) as an interactor. CYLN2 is a large (1,046 amino acid) protein that contains an N-terminal globular domain with two CAP-Gly (microtubule-binding) motifs, and a large central coiled-coil region. CAP-Gly domains are ~42 amino acid motifs found in proteins such as Restin (also known as CLIP-170), which links endocytic vesicles to microtubules, and dynactin, which stimulates dynein-mediated vesicle transport. The presence of these motifs suggests that CYLN2 functions to control vesicular transport in association with the cytoskeleton, and indeed this is the case. CYLN2 is able to bind microtubules and is enriched in dendritic lamellar body (DLB), an organelle that is actively localized to dendritic appendages in a microtubule-dependent fashion. Recent analyses demonstrate that the association of CYLN2 with microtubules is sensitive to phosphorylation and is dependent not only on its CAP-Gly domains but also on the surrounding basic, Ser-rich regions, and furthermore that CYLN2 colocalizes with Restin at the distal ends of microtubules in transfected COS-1 cells. Hoogenrad et al., *J. Cell Sci.*, 113 (Pt 12):2285–97 (2000). There is also evidence suggesting clinical relevance of CYLN2: the CYLN2 gene is localized to 7q11.23, a region commonly deleted in Williams syndrome, a multisystemic developmental disorder that includes infantile hypercalcemia, dysmorphic facies, and mental retardation. Hoogenrad et al., *Genomics*, 53(3):348–58 (1998). However, it has not yet been demonstrated whether deletion of CYLN2 is responsible for Williams syndrome. Although CYLN2 has been described by one group as a brain-specific protein, expression of homologous ESTs is observed in a wide variety of tissues. One clone encoding amino acids 607–947 of CYLN2 (corresponding to part of the central coiled-coil motif) was isolated according to the present invention.

In addition, we also identified an interaction between Tsg101 and Restin. The similarity of both the domain structures and functions of Restin and CYLN2 strengthens the notion that the interaction of Tsg101 with these proteins is physiologically relevant.

2.1.12. Tsg101 Interacts with the Tropomyosin TPM4

A search of a macrophage library with the tumor suppressor protein Tsg101 identified the tropomyosin TPM4 as an interactor. Tropomyosins are small, acidic, coiled-coil proteins that bind as dimers along the length of actin filaments and coordinate the formation of contractile bundles (as opposed to a network of actin filaments). Binding of tropomyosin stabilizes and stiffens the actin filament, inhibits the binding of filamin, and facilitates the binding of myosin to actin filaments, thereby facilitating the formation of a contractile actin bundle. TPM4 was isolated from human fibroblasts based on homology to horse tropomyosin, and was described as one of five proteins in human fibroblasts similar to tropomyosins. MacLeod et al., *J. Mol. Biol.*, 194(1):1–10 (1987). TPM4 is a non-muscle tropomyosin, but both muscle and non-muscle forms are produced by alternative splicing of the same four genes. The interaction of Tsg101 with TPM4 provides yet another link between Tsg101 and regulation of the cytoskeleton. Analysis of homologous ESTs suggests widespread expression of TPM4.

2.1.13. Tsg101 Interacts with KIAA0674

A search of a macrophage and spleen libraries with two different tumor suppressor protein Tsg101 baits identified the FK506-binding protein (FKBP) homolog KIAA0674 as an interactor. The available KIAA0674 sequence, which is incomplete, predicts a 1234 amino acid protein. KIAA0674 contains an FKBP-type peptidyl-prolyl cis-trans isomerase (PPIase) domain, which is likely involved in promoting protein folding by catalyzing the isomerization of proline imidic peptide bonds. FKBPs, which bind the immunosuppressive drug FK506, possess this domain and display PPIase activity. In addition, KIAA0674 contains an N-terminal WASp homology (WH) domain, found in the Wiskott-Aldrich syndrome protein (WASp) involved in the transmission of signals to the cytoskeleton. The WH motif is also found in Homer proteins (e.g. Homer-1B) which are involved in neurotransmitter release, and there is evidence that the WH domain is responsible for binding polyproline-containing peptides in glutamate receptors and cytoskeletal components. In addition, KIAA0674 contains a central coiled-coil region that displays weak similarity to myosin heavy chain, plectin, and golgin-like proteins. The presence of these domains suggests a function for KIAA0674 in controlling the conformation of cytoskeletal or other proteins, perhaps in response to extracellular signals. Analysis of homologous ESTs suggests expression of KIAA0674 in a wide variety of tissues. Six prey clones encoding amino acids 770–880 of KIAA0674 were isolated according to the present invention; this region corresponds to the central coiled-coil domain. The isolation of multiple KIAA0674 clones with independent Tsg101 baits strengthens the notion that this may be a biologically relevant interaction.

Interestingly, the HIV GAG protein has been shown to interact with the PPIase-domain protein folding catalysts cyclophilin A and cyclophilin B. Luban et al., *Cell*, 73(6): 1067–78 (1993). Cyclophilin A (CypA) is incorporated into HIV virions (Colgan et al., *J. Virol.*, 70(7):4299–310 (1996)), and there is evidence that CypA mediates attachment of the virus to the cell surface by binding to heparan. Saphire et al., *EMBO J.*, 18(23):6771–85 (1999). Consistent with this, HIV-1 exhibits decreased replication in T cells in which the CypA gene has been deleted by homologous recombination, and viruses produced by CypA-deficient cells are less infectious than virions from wild type cells. While it seems that CypA plays a role in an early step in viral infection, it is also possible that CypA, and other PPIase proteins including KIAA0674, also function during viral assembly and budding; the functions of these proteins as catalysts of protein folding certainly raises the possibility that they assist in the assembly of virus particles.

2.1.14. Tsg101 Interacts with Plectin 1

A search of a spleen library with the tumor suppressor protein Tsg101 identified Plectin 1 (plectin) as an interactor. Plectin is an intermediate filament binding protein that crosslinks intermediate filaments, links intermediate filaments to microtubules and microfilaments, and anchors intermediate filaments to both the plasma and nuclear membranes. Plectin is able to self-associate, forming networks that stabilize the cytoskeleton. Plectin is one of the largest known proteins (4574 amino acids, 518 kD). Liu et al., *Proc. Natl. Acad. Sci.*, 93(9):4278–83 (1996). Plectin contains an N-terminal globular domain with two calponin homology (CH) motifs (responsible for binding to actin), a central rod-like domain containing coiled-coil regions, and a repetitive C-terminal globular domain (plectin repeats). Mutations in plectin have been shown to cause muscular dystrophy with epidermolysis bullosa simplex (MD-EBS), a disorder characterized by epidermal blister formation associated with muscular dystrophy. Gache et al., *J. Clin. Invest.*, 97(10): 2289–98 (1996); Smith et al., *Nat. Genet.*, 13(4): 450–7 (1996); MacLean et al., *Genes Dev.*, 10(14):1724–35 (1996). Plectin has been shown to be a major early substrate for caspase-8 during CD95- and TNF receptor-mediated apoptosis, and in primary fibroblasts from plectin-deficient mice, apoptosis-induced reorganization of the cytoskeleton was severely impaired. Stegh et al., *Mol. Cell Biol.*, 20(15): 5665–79 (2000). These results suggest an active role for plectin in controlling the cellular changes associated with apoptosis.

Immunocytological analysis of transfected HeLa cells demonstrates the localization of Vif protein to perinuclear aggregates, and the relocalization of cytoskeletal components including vimentin and plectin (but not tubulin) to these sites. In COS-7 cells, Vif does not form perinuclear aggregates, but rather is found throughout the cytoplasm; nonetheless, Vif expression in COS-7 cells is still able to induce perinuclear aggregation of vimentin and plectin. Although the redistribution of plectin upon Vif expression is certainly not proof of physical interaction, it is suggestive of at least a functional connection between these proteins. Two prey clones from plectin were isolated by ProNet; these encode similar but distinct fragments corresponding to the central coiled-coil region of the protein.

The interaction of Tsg101 with plectin, and the altered intracellular behavior of plectin upon expression of HIV-1 Vif protein, suggest that plectin may be involved in HIV-1 infection. Plectin has been previously shown by ProNet to interact with calgranulin B (CAGB), a protein expressed by macrophages in acutely and chronically inflamed tissues, and constitutively in epithelial cells. Calgranulin binds calcium and interacts with other intermediate filament components, providing yet another link between HIV-1 and the cytoskeleton.

2.1.15. Tsg101 Interacts with the Actin Binding Protein ACTN4

A search of a spleen library with the tumor suppressor protein Tsgll identified ACTN4 as an interactor. ACTN4 was identified as an actin-bundling protein associated with cell motility and cancer invasiveness. Honda et al., *J. Cell Biol.*, 140(6): 1383–93 (1998). ACTN4 localizes to the cytoplasm where it links actin to membranes in non-muscle cell types and anchors myofibrillar actin filaments in skeletal, cardiac, and smooth muscle cells. ACTN4 is conspicuously absent from focal adhesion plaques and adherens junctions, where the classic isoform (ACTN4 1) is localized. Subsequent analysis (El-Husseini et al., *Biochem. Biophys. Res. Commun.*, 267(3):906–11 (2000)) demonstrated that ACTN4 binds to and colocalizes with BERP, a member of the RING-B-box-coiled-coil (RBCC) subgroup of RING finger proteins. BERP is a specific partner for the tail domain of myosin V, a class of myosins which are involved in the targeted transport of organelles, suggesting that BERP, and by inference ACTN4, may be involved in intracellular cargo transport. El-Husseini et al., *J. Biol. Chem.*, 274(28): 19771–7 (1999). Mutations in ACTN4 are associated with focal and segmental glomerulosclerosis (FSGS), a common, non-specific renal lesion characterized by urinary protein secretion and decreasing kidney function. Kaplan et al., *Nat. Genet.*, 24(3):251–6 (2000). Mutant forms of ACTN4 bind actin more strongly than does the wild type protein, resulting in misregulation of the actin cytoskeleton in glomerular cells of affected FSGS patients. ACTN4 is an 884 amino acid protein with a domain structure very similar to that of PLEC1: ACTN4 contains two N-terminal CH (actin-binding) motifs and a C-terminal repetitive region (spectrin repeats). In addition, ACTN4 contains two C-terminal EF-hand calcium binding motifs.

2.1.16. Tsg101 interacts with PIBF1

A search of a spleen library with the tumor suppressor protein Tsg101 (amino acids 12–326) identified PIBF1 as an interactor. PIBF1 is a 758 amino acid protein that contains numerous coiled-coil motifs and a weak match to the Syntaxin N-terminal domain motif, which is involved in interaction of SNAREs during vesicular docking and fusion. In addition, PIBF1 displays weak homology to myosin heavy chain. The presence of these domains suggests that PIBF1 may be involved in regulating the cytoskeleton or in vesicular transport. Analysis of homologous ESTs suggests expression of PIBF1 in a variety of tissues. Two prey clones from PIBF1 have been isolated; these encode a region of PIBF1 (amino acids 392–758) that contains two of the coiled-coil motifs.

2.1.17. Tsg101 Interacts with BAP31

A search of a spleen library using amino acids 12–326 of the tumor suppressor protein Tsg101 revealed an interaction with the transmembrane ER protein BAP31. BAP31 was initially identified as a protein that binds membrane immunoglobulins (IgM, IgD). Kim et al., *EMBO J.*, 13(16): 3793–800 (1994). BAP31 is a small protein (246 amino acids) with three predicted TM domains at the N-terminus and a C-terminal coiled-coil region. The C-terminus ends in -KKXX, a motif implicated in vesicular transport. BAP31 localizes to the ER membrane with the C-terminus extending into the cytoplasm; truncation of this tail abolishes the export of certain proteins, such as cellubrevin, from the ER. Annaert et al., *J. Cell Biol.*, 139(6):1397–410 (1997).

Together, these observations suggest a role for BAP31 as a cargo transporter, mediating the transfer of specific proteins out of the ER. Interestingly, BAP31 has been shown to form a complex with Bcl-2/Bcl-XL and procaspase-8 in the ER (Ng et al., *J. Cell Biol.*, 139(2):327–38 (1997); Ng and Shore, *J. Biol. Chem.*, 273(6):3140–3 (1998)), and is proposed to act as a bridge between Bcl proteins and caspases, thereby regulating caspase activity with respect to Bcl protein status.

Furthermore, BAP31 is cleaved by caspase-1 and -8 activity, removing eight C-terminal amino acids including the —KKXX motif. Maatta et al., *FEBS Lett.*, 484(3):202–6 (2000). Expression of the BAP31 cleavage product in BHK-21 and NRK (kidney) cells induces subsequent apoptotic events such as the formation of membrane blebs. Expression of the BAP31 cleavage product also prevents ER to Golgi transport of Semliki Forest virus glycoproteins and the Golgi-resident protein mannosidase II, further demonstrating a role for BAP31 in protein export from the ER. The prey construct isolated herein encodes the C-terminus of BAP31, corresponding to most of the C-terminal coiled-coil motif.

2.1.18. Tsg101 Interacts with Zinc Finger Protein 231

A search of a brain library with the tumor suppressor protein Tsg101 (amino acids 231–390) identified the zinc finger protein 231 as an interactor. Zinc finger protein 231 is a very large protein (3926 amino acids) that was first discovered by its elevated expression in brains from patients with multiple system atrophy (MSA), a neurodegenerative disease. Hashida et al., *Genomics*, 54(1):50–8 (1998). Though first found in brain, analysis of homologous EST expression suggests that zinc finger protein 231 is ubiquitously expressed. Analysis of the zinc finger protein 231 protein sequence reveals two nuclear localization signals, numerous proline-, glutamic acid-, and glutamine-rich regions, several small coiled-coil motifs, and several weak matches to the PHD-type zinc finger motif; the PHD finger is a C4HC3 zinc-finger-like motif found in nuclear proteins involved in chromatin-mediated transcriptional regulation. Much of the domain structure of zinc finger protein 231 suggests a possible role as a transcription factor. However, zinc finger protein 231 also contains several weak matches to the FYVE-type zinc finger domain, which is found in proteins such as EEA1 and is a Zn— and PI3P-binding domain likely involved in endosomal targeting, suggesting roles for zinc finger protein 231 in vesicular trafficking. Strong support for such a role comes from analysis of the homologous murine protein, Bassoon, which displays an extraordinary degree of sequence similarity to zinc finger protein 231 (89% amino acid identity over the entire protein). Bassoon is a cytoskeletal-associated protein found in the presynaptic compartment of mouse brain cells, and is thought to be involved in controlling cytomatrix organization at the site of neurotransmitter release. Dieck et al., *J. Cell Biol.*, 142(2):499–509 (1998). Electron microscopy of a synapse active zone fraction showed Bassoon associated with vesicular structures, suggesting a role for Bassoon in regulating neurotransmitter release. Sanmarti-Vila et al., *J. Cell Biol.*, 142(2):499–509 (2000). Given the degree of sequence identity between Bassoon and zinc finger protein 231, it is reasonable to hypothesize a role for zinc finger protein 231 in neurotransmitter-containing vesicle docking, fusion, and/or recycling, and to propose that the interaction of zinc finger protein 231 with Tsg101 facilitates viral budding.

2.1.19. Tsg101 Interacts with HCAP

Searches of a macrophage and spleen libraries with amino acids 231–390 and 119–353 of the tumor suppressor protein Tsg101 identified interactions with HCAP, a human chromosome-associated polypeptide. HCAP is a 1,217 amino acid protein thought to regulate the assembly and structural maintenance of mitotic chromosomes. Shimizu et al., *J Biol Chem* 273(12):6591–4 (1998). Analysis of homologous EST expression suggests ubiquitous tissue expression. HCAP has four domains of interest: N-terminal and C-terminal structural maintenance of chromosome (SMC) domains, a myosin tail domain, and a weak match to the ABC transporter domain. The SMC domain contains a P-loop and a DA box motif that act cooperatively to bind ATP. Ghiselli et al., *J. Biol. Chem.*, 274(24): 17384–93 (1999). HCAP is 99% identical over ~1200 amino acids to murine and rat bamacan, a basement membrane-chondroitin sulfate proteoglycan. Overexpression of bamacan in NIH and Balb/c 3T3 cells causes transformation, and the levels of expression detected in those transformed cells were the same as levels in spontaneously transformed human colon carcinoma cells. Ghiselli and Iozzo, *J. Biol. Chem.*, 275(27):20235–8 (2000). Concentrations of HCAP have been found in the nucleus, giving credibility to an interaction found between HCAP and the small G protein GDP dissociation stimulator-associated protein SMAP, which is also present in the nucleus. SMAP is phosphorylated by Src tyrosine kinase and interacts with 5 mg GDS, a protein which regulates Rho and Ras activity. Shimizu et al., *J. Biol. Chem.*, 271(43):27013–7 (1996); Sasaki et al., *Biochem. Biophys. Res. Commun.*, 194(3): 1188–93 (1993). HCAP, SMAP, and KIF3B, a kinesin family member that functions as a microtubule-based motor for organelle transport, can be extracted from the nuclear fraction as a ternary complex. Shimizu et al., *J. Biol. Chem.*, 273(12):6591–4 (1998). The discovery of this complex has led to the hypothesis that SMAP serves as a link between chromosomes, bound by HCAP, and ATP-based motor proteins like KIF3B.

2.2. Tsg101 is Involved in HIV Viral Budding

Tumor susceptibility gene 101 (Tsg101) was originally identified as a 381 amino acid polypeptide involved in tumorigenesis. Tsg101 can be localized in the nucleus and in the cytoplasm depending on the stage of cell cycle. Tsg101 interacts with stathmin, a cytosolic phosphoprotein implicated in tumorigenesis, and overexpression of a Tsg101antisense transcript in NIH-3T3 cells results in transformation of the cells. See Li and Cohen, Cell, 85(3):319–29 (1996). Furthermore, it has been suggested that defects in Tsg101 may occur during breast cancer tumorigenesis and/or progression. Li et al., Cell, 88(1): 143–54 (1997). Tsg101 contains a ubiquitin-conjugating enzyme E2 catalytic domain. Recently, interest has focused on Tsg101 as a possible component of the ubiquitin/proteasome degradation pathway. By database search and comparison, it has been found that that N-terminal Tsg101 contains a domain related to E2 ubiquitin-conjugating (Ubc) enzymes although lacking the active site cysteine. See Koonin and Abagyan, Nat. Genet., 16(4):330–1 (1997). Thus, Tsg101 may belong to a group of apparently inactive homologs of Ubc enzymes. See id. The domain related to E2 ubiquitin-conjugating (Ubc) enzymes is referred to ubiquitin E2 variant (UEV) domain.

In accordance with the present invention, a search of a human spleen library with GAG polyprotein (aa 449–500, p6 domain, or "GAGp6") of HIV-1 isolated the tumor susceptibility TSG 101 protein (Tsg101; aa 7–390) as an interactor. The GAGp6 bait used here contains a late domain motif (-PTAP-). The GAG polyprotein of retroviruses gives rise to a set of mature proteins (matrix, capsid, and nucleocapsid) that produce the inner virion core. In addition, GAG also contains a C-terminal portion called p6. In the case of HIV1, GAGp6 contains a sequence called the late domain, so-called because it is required for a late stage of HIV viral budding from the host cell surface. The late domain has a functional relationship with ubiquitin, in that the late domain is required in viral budding, and depletion of the intracellular pool of free ubiquitin produces a similar late phenotype. Patnaik et al., Proc. Natl. Acad. Sci. USA, 97(24):13069–74 (2000); Schubert et al., Proc. Natl. Acad. Sci. USA, 97(24): 13057–62 (2000); Strack et al., Proc. Natl. Acad. Sci. USA, 97(24): 13063–8 (2000). The late domain is thought to represent a docking site for the ubiquitination machinery.

As is known in the art, the P(T/S)AP motif is conserved among the GAGp6 domains of all known primate lentiviruses. In nonprimate lentiviruses, which lack a GAGp6 domain, the P(T/S)AP motif is at the immediate C terminus of the GAG polyprotein. It has been shown that the P(T/S) AP motif is required for a late stage of viral budding from the host cell surface. It is critical for lentivirus' and particularly HIV's particle production. See Huang et al., J. Virol., 69:6810–6818 (1995). Specifically, deletion of the PTAP motif results in drastic reduction of viral particle production. In addition, the PTAP-deficient viruses proceeded through the typical stages of morphogenesis but failed to complete the process. Rather, they remain tethered to the plasma membrane and are thus rendered non-infectious. That is, the viral budding process is stalled. See Huang et al., J. Virol., 69:6810–6818 (1995).

In accordance with the present invention, different GAGp6 point mutants (E6G, P7L, A9R, or P10L) were generated and tested for their ability to bind Tsg101 protein. See Example 2 below. While the wild-type GAGp6 peptide and the E6G GAGp6 mutant were capable of binding Tsg101 protein, each of the P7L, A9R, and PLOL point mutations abolishes the GAGp6 binding affinity to Tsg101. The P7L, A9R, and P10L point mutations alter the PTAP motif in GAGp6 peptide. The same mutations in the PTAP motif of the HIV GAGp6 gag protein prevent HIV particles from budding from the host cells. See Huang et al., J. Virol., 69:6810–6818 (1995). Further, as shown in Example 3 below, the inventors of the present invention discovered that the first 14 amino acid residues of HIV GAGp6 (which includes the PTAP late domain motif) are sufficient in binding to the N-terminal portion of Tsg101 (amino acid residues 1–207, which includes the Tsg101 UEV domain).

As discussed above, the large number of protein-protein interactions discovered according to the present invention suggest that Tsg101 is intimately involved in endocytosis, intracellular vesicle trafficking, and vacuolar protein sorting (VPS). The VPS pathway sorts membrane-bound proteins for eventual degradation in the lysosome (vacuole in yeast). See Lemmon and Traub, Curr. Opin. Cell. Biol., 12:457–66 (2000). Two alternative entrees into the VPS pathway are via vesicular trafficking from the Golgi (e.g., in degrading misfolded membrane proteins) or via endocytosis from the plasma membrane (e.g., in downregulating surface proteins like epidermal growth factor receptor (EGFR)). Vesicles carrying proteins from either source can enter the VPS pathway by fusing with endosomes. As these endosomes mature, their cargos are sorted for lysosomal degradation via the formation of structures called multivesicular bodies (MVB). MVB are created when surface patches on late endosomes bud into the compartment, forming small (~50–100 nm) vesicles. A maturing MVB can contain tens or even hundreds of these vesicles. The MVB then fuses with the lysosome, releasing the vesicles for degradation in this hydrolytic organelle.

The Tsg101 prey fragment isolated in yeast two-hybrid assay contains the ubiquitin E2 variant (UEV) domain indicating that the UEV domain is involved in the binding to the P(T/S)AP domain. The involvement of the Tsg101 UEV domain is consistent with the fact that ubiquitin is required for retrovirus budding and that proteasome inhibition reduces the level of free ubiquitin in HIV-1-infected cells and interferes with the release and maturation of HIV-1 and HIV-2. See Patnaik et al., Proc. Natl. Acad. Sci. USA, 97(24): 13069–74 (2000); Schubert et al., Proc. Natl. Acad. Sci. USA, 97(24): 13057–62 (2000); Strack et al., Proc. Natl. Acad. Sci. USA, 97(24): 13063–8 (2000).

It is known that short chains of Ub (1–3 molecules) can "mark" surface receptors for endocytosis and degradation in the lysosome. Hicke, Trends Cell Biol., 9:107–112 (1999); Rotin et al., J. Membr. Biol., 176:1–17 (2000). Several classes of proteins that carry the P(T/S)AP motif are surface receptors known to be degraded via the VPS pathway or function in the VPS pathway. See Farr et al., Biochem. J., 345(3):503–509 (2000); Staub and Rotin., Structure, 4:495–499 (1996). Although it is not known whether Tsg101 lacks ubiquitin ligase activity, it is believed, based on the large number of Tsg101interactors discovered in accordance with the present invention, that a plausible role for Tsg101 in the VPS pathway is to recognize ubiquitinated proteins that carry P(T/S)AP motifs and help coordinate their incorporation into vesicles that bud into the MVB.

This is especially intriguing because the formation of MVB is the only known cellular process in which cell buds a vesicle out of the cytoplasm into another compartment.

This budding is topologically equivalent to viral budding in which viruses bud out of the cytoplasm at the plasma membrane into excellular space. Accordingly, while not wishing to be bound by any theory, it is believed that the binding of the P(T/S)AP motif in lentivirus GAG polyproteins to the cellular protein Tsg101 enables lentiviruses having the P(T/S)AP motif to usurp cellular machinery normally used for MVB formation to allow viral budding from the plasma membrane. It is also believed that depletion of Tsg101 or interfering with the interaction between Tsg101 and the P(T/S)AP motif in lentivirus-infected cells will prevent lentiviral budding from the cells.

In addition, the recruitment of cellular machinery to facilitate virus budding appears to be a general phenomenon, and distinct late domains have been identified in the structural proteins of several other enveloped viruses. See Vogt, Proc. Natl. Acad. Sci. USA, 97:12945–12947 (2000). Two well characterized late domains are the "PY" motif (consensus sequence: PPXY; X=any amino acid) found in membrane-associated proteins from certain enveloped viruses. See Craven et al., J. Virol., 73:3359–3365 (1999); Harty et al., Proc. Natl. Acad. Sci. USA, 97:13871–13876 (2000); Harty et al., J. Virol., 73:2921–2929 (1999); and Jayakar et al., J. Virol., 74:9818–9827 (2000). The cellular target for the PY motif is Nedd4 which also contains a Hect ubiquitin E3 ligase domain. The "YL" motif (YXXL) was found in the GAG protein of equine infectious anemia virus (EIAV). Puffer et al., J. Virol., 71:6541–6546 (1997); Puffer et al., J. Virol., 72:10218–10221 (1998). The cellular receptor for the "YL" motif appears to be the AP-50 subunit of AP-2. Puffer et al., J. Virol., 72:10218–10221 (1998). Interestingly, the late domains such as the P(T/S)AP motif, PY motif and the YL motif can still function when moved to different positions within retroviral GAG proteins, which suggests that they are docking sites for cellular factors rather than structural elements. Parent et al., J. Virol., 69:5455–5460 (1995); Yuan et al., EMBO J., 18:4700–4710 (2000). Moreover, the late domains such as the P(T/S)AP motif, PY motif and the YL motif can function interchangeably. That is one late domain motif can be used in place of another late domain motif without affecting viral budding. Parent et al., J. Virol., 69:5455–5460 (1995); Yuan et al., EMBO J., 18:4700–4710 (2000); Strack et al., Proc. Natl. Acad. Sci. USA, 97:13063–13068 (2000).

Accordingly, while not wishing to be bound by any theory, it is believed that as shown in FIG. 1, although the three late domain motifs bind to different cellular targets, they utilize common cellular pathways to effect viral budding. In particular, it is believed that the different cellular receptors for viral late domain motifs feed into common downstream steps of the vacuolar protein sorting (VPS) and MVB pathway. As discussed above, Tsg101 functions in the VPS pathway. Another protein, Vps4 functions in Tsg101 cycling and endosomal trafficking. Particularly, Vps4 mutants prevent normal Tsg101 trafficking and induce formation of aberrant, highly vacuolated endosomes that are defective in the sorting and recycling of endocytosed substrates. See Babst et al, Traffic, 1:248–258 (2000).

Interestingly, a search of a spleen library with the tumor susceptibility protein Tsg101 also identified an interaction with the growth arrest-specific protein GAS7b. In addition, as disclosed in the commonly assigned U.S. Provisional Application Serial No. 60/311,528, GAS7b is an interactor of the capsid region of the HIV GAG polyprotein. GAS7b is expressed preferentially in cells that are entering the quiescent state. Inhibition of GAS7b expression in terminally differentiating cultures of embryonic murine cerebellum impedes neurite outgrowth, while overexpression in undifferentiated neuroblastoma cell cultures dramatically promotes neurite-like outgrowth. Ju et al., Proc Natl Acad Sci 95(19):11423–8 (1998); Lazakovitch et al., Genomics 61(3): 298–306 (1999). These findings suggest a role for GAS7b in controlling terminal cellular differentiation, and the domain structure of GAS7b suggests it may do this by regulating the cytoskeleton. In addition, GAS7b also interacts with two different regulators of small GTPases that control the actin cytoskeleton. The interactions of GAS7b with the HV capsid and with Tsg101 (which in turn interacts with the HIV GAGp6 protein) strongly suggests these proteins form a multimolecular complex involved in the late stages of viral assembly and budding.

2.3. Protein Complexes

As discussed above, the UEV domain of the Tsg101 protein and the PTAP motif of the HIV GAGp6 are responsible for the interactions. In addition, an examination of HIV-1 amino acid sequence variants in GenBank by the inventors using BLAST (Basic Local Alignment Search Tool) identified a number of HIV strains with the standard PTAP motif being replaced with variations of the motif, indicating that such variations can also enable viral budding and that peptides with such variations may also bind Tsg101. Such identified variations include the PSAP motif, the PIAP motif (see Zhang et al., J. Virol., 71:6662–6670 (1997); Farrar et al., J. Med. Virol., 34:104–113 (1991)), and the PTTP motif (see Zhang et al., J. Virol., 71:6662–6670 (1997).

Accordingly, the present invention provides protein complexes formed by interactions between Tsg101 and HIV GAGp6. The present invention also provides a protein complex having a homologue, derivative or fragment of Tsg101 interacting with HIV GAGp6. In addition, the present invention further encompasses a protein complex having Tsg101 interacting with a homologue, derivative or fragment of HIV GAGp6. In yet another embodiment, a protein complex is provided having a homologue, derivative or fragment of Tsg101 and a homologue, derivative or fragment of HIV GAGp6. In another embodiment, the present invention encompasses a protein complex, or fusion protein, having a first polypeptide covalently linked to a second polypeptide, wherein said first polypeptide is Tsg101 or fragment or homologue or derivative thereof, and wherein said second polypeptide is HIV GAG or fragment or homologue or derivative thereof. In other words, one or more of the interacting protein members of a protein complex of the present invention may be a native protein or a homologue, derivative or fragment of a native protein.

Thus, for example, one interacting partner in the protein complexes can be a complete native Tsg101, a Tsg101 homologue capable of interacting with the HIV GAGp6, a Tsg101 derivative, a derivative of the Tsg101 homologue, a Tsg101 fragment capable of interacting with HIV GAGp6 (e.g., a fragment containing the UEV domain of the Tsg101 protein, specifically the amino acid residues 1–207, the amino acid residues 1–147, etc.), a derivative of the Tsg101 fragment, or a fusion protein containing (1) complete native Tsg101, (2) a Tsg101 homologue capable of interacting with the HIV GAGp6 or (3) a Tsg101 fragment capable of interacting with HIV GAGp6.

The protein complexes of the present invention contains a HIV GAG polypeptide as an interacting partner. In addition, GAG polypeptides and fragments thereof from other retroviruses containing the P(T/S/I)(A/T)P (SEQ ID NOs:

1–6) late domain motif are believed to also interact with Tsg101 in the same manner as the HIV GAG polypeptide. Thus, they can be used in forming protein complexes with Tsg101 or a homologue or derivative or fragment thereof. Preferably, GAG polypeptides or fragments thereof of lentiviruses containing the P(T/S)AP late domain are used to form protein complexes. Such GAG polypeptides or fragments thereof may be from a non-primate lentiviruses including bovine lentiviruses (e.g. bovine immunodeficiency virus (BIV), Jembrana disease virus), feline lentiviruses (e.g. feline immunodeficiency virus (FIV) which causes immunodeficiency, wasting, and encephalitis in cats), and ovine/caprine lentivirus (e.g. caprine arthritis-encephalitis virus (CAEV) which causes anemia and wasting in goats, ovine lentivirus, Visna virus which causes pneumonia, wasting, encephalitis and arthritis). Preferably, the GAG polypeptides or fragments thereof are from primate lentiviruses including, but not limited to, human immunodeficiency virus type 1 (HIV-1), human immunodeficiency virus type 2 (HIV-2), human immunodeficiency virus type 3 (HIV-3) (all of which cause AIDS), and various simian immunodeficiency viruses that infect hosts such as chimpanzee, mangabey, African Green monkey, mandrill, L'Hoest, Sykes' monkey, or Guereza Colobus monkey.

In one embodiment, the present invention encompasses an isolated protein complex comprising (a) a first protein that is (i) Tsg101 protein, (ii) a Tsg101 protein homologue having an amino acid sequence at least 90% identical to that of Tsg101 and capable of interacting with HIV GAGp6, (iii) a Tsg101 protein fragment containing the Tsg101 UEV domain, or (iv) a fusion protein containing said Tsg101 protein, said Tsg101 protein homologue or said Tsg101 protein fragment; and (b) a second protein that is (1) HIV GAG polypeptide, (2) a HIV GAG polypeptide fragment, (3) a HIV GAG polypeptide homologue having an amino acid sequence at least 90% identical to that of HIV GAG polypeptide and capable of interacting with Tsg101, (4) HIV GAGp6 protein, (5) a HIV GAGp6 homologue having an amino acid sequence at least 90% identical to that of HIV GAGp6 polypeptide and capable of interacting with Tsg101, (6) a HIV GAGp6 fragment capable of interacting with Tsg101, or (7) a fusion protein containing said HTV GAG polypeptide. said HIV GAG polypeptide fragment, said HIV GAG polypeptide homologue, said HIV GAGp6 protein, said HIV GAGp6 homologue or said HIV GAGp6 fragment.

Besides native GAG polypeptides, useful interacting partners for Tsg101 or a homologue or derivative or fragment thereof also include homologues of GAG polypeptides capable of interacting with Tsg101, derivatives of the native or homologue GAG polypeptides capable of interacting with Tsg101, fragments of the GAG polypeptides capable of interacting with Tsg101 (e.g., a fragment containing the P(T/S)AP motif), derivatives of the GAG polypeptide fragments, or fusion proteins containing (1) a complete GAG polypeptide, (2) a GAG polypeptide homologue capable of interacting with Tsg101 or (3) a GAG polypeptide fragment capable of interacting with Tsg101.

In specific embodiments, the protein complex of the present invention contains a polypeptide that contains a contiguous span of at least 7, 8, 9, 10, 11, 12, 13, 14, 15 or more amino acid residues of a naturally occurring HIV GAG sequence. Preferably, the polypeptide contains a contiguous span of at least 10, 11, 12, 13, 14, 15 or more amino acid residues of a naturally occurring HIV GAG sequence. The contiguous span should span the HIV late domain motif which can be the P(T/S)AP motif or a variation thereof (e.g., the PIAP motif and the PTTP motif). Preferably, the late domain motif in the contiguous span is the P(T/S)AP motif. In other specific embodiments, the protein complex contains a polypeptide that contains a contiguous span of at least 8, 9, 10, 11, 12, 13, 14, 15 or more amino acid residues of a naturally occurring GAG polypeptide sequence from other retroviruses containing a P(T/S)AP late domain motif. The contiguous span should span the retrovirus late domain motif. In preferred embodiments, such other retroviruses are primate lentiviruses or non-primate lentiviruses (except for EIAV). In specific embodiments, the protein complex of the present invention includes a polypeptide comprising an amino acid sequence selected from the group of EPTAP (SEQ ID NO:7), EPSAP (SEQ ID NO:8), PTAPP (SEQ ID NO:9), PSAPP (SEQ ID NO:10), EPTAPP (SEQ ID NO:11), EPSAPP (SEQ ID NO:12), PEPTAP(SEQ ID NO:13), PEPSAP (SEQ ID NO:14), RPEPTAP (SEQ ID NO:15), RPEPSAP (SEQ ID NO:16), PEPTAPP (SEQ ID NO:17), PEPSAPP (SEQ ID NO:18), EPTAPPEE (SEQ ID NO:19), EPSAPPEE (SEQ ID NO:20), EPTAPPAE (SEQ ID NO:21), PEPTAPPEE (SEQ ID NO:22), PEPTAPPAE (SEQ ID NO:23), PEPSAPPEE (SEQ ID NO:24), RPEPTAPPEE (SEQ ID NO:25), RPEPSAPPEE (SEQ ID NO:26), RPEPTAPPAE (SEQ ID NO:27), RPEPSAPPAE (SEQ ID NO:28), LQSRPEPTAPPEE (SEQ ID NO:29), LQSRPEPSAPPEE (SEQ ID NO:30), LQSRPEPTAPPEES (SEQ ID NO:31), and LQSRPEPSAPPEES (SEQ ID NO:32).

Furthermore, it is believed that the P(T/S)AP or PIAP or PTTP motif itself may be sufficient for Tsg101 binding. Accordingly, a protein complex is also provided containing Tsg101 protein or a homologue or derivative or fragment thereof interacting with a polypeptide consisting essentially the P(T/S)AP or PIAP or PTTP motif, i.e., a polypeptide having the P(T/S)AP or PIAP or PTTP motif and a few flanking amino acids.

In a specific embodiment of the protein complex of the present invention, two or more interacting partners (Tsg101 and HIV GAGp6, or homologues, derivatives or fragments thereof) are directly fused together, or covalently linked together through a peptide linker, forming a hybrid protein having a single unbranched polypeptide chain. Thus, the protein complex may be formed by "intramolecular" interactions between two portions of the hybrid protein. Again, one or both of the fused or linked interacting partners in this protein complex may be a native protein or a homologue, derivative or fragment of a native protein.

The protein complexes of the present invention can also be in a modified form. For example, an antibody selectively immunoreactive with the protein complex can be bound to the protein complex. In another example, a non-antibody modulator capable of enhancing the interaction between the interacting partners in the protein complex may be included. Alternatively, the protein members in the protein complex may be cross-linked for purposes of stabilization. Various crosslinking methods may be used. For example, a bifunctional reagent in the form of R—S—S—R' may be used in which the R and R' groups can react with certain amino acid side chains in the protein complex forming covalent linkages. See e.g., Traut et al., in Creighton ed., *Protein Function: A Practical Approach,* IRL Press, Oxford, 1989; Baird et al., *J. Biol. Chem.,* 251:6953–6962 (1976). Other useful crosslinking agents include, e.g., Denny-Jaffee reagent, a heterbiofunctional photoactivable moiety cleavable through an azo linkage (See Denny et al., *Proc. Natl. Acad. Sci. USA,* 81:5286–5290 (1984)), and $^{125}$I-{S-[N-(3-iodo-4-azidosalicyl)cysteaminyl]-2-thiopyridine}, a cysteine-specific photo-crosslinking reagent (see Chen et al., *Science,* 265:90–92 (1994)).

The above-described protein complexes may further include any additional components e.g., other proteins, nucleic acids, lipid molecules, monosaccharides or polysaccharides, ions or other molecules.

2.4. Methods of Preparing Protein Complexes

The protein complex of the present invention can be prepared by a variety of methods. Specifically, a protein complex can be isolated directly from an animal tissue sample, preferably a human tissue sample containing the protein complex. Alternatively, a protein complex can be purified from host cells that recombinantly express the members of the protein complex. As will be apparent to a skilled artisan, a protein complex can be prepared from a tissue sample or recombinant host cell by coimmunoprecipitation using an antibody immunoreactive with an interacting protein partner, or preferably an antibody selectively immunoreactive with the protein complex as will be discussed in detail below. The antibodies can be monoclonal or polyclonal. Coimmunoprecipitation is a commonly used method in the art for isolating or detecting bound proteins. In this procedure, generally a serum sample or tissue or cell lysate is admixed with a suitable antibody. The protein complex bound to the antibody is precipitated and washed. The bound protein complexes are then eluted.

Alternatively, immunoaffinity chromatography and immunobloting techniques may also be used in isolating the protein complexes from native tissue samples or recombinant host cells using an antibody immunoreactive with an interacting protein partner, or preferably an antibody selectively immunoreactive with the protein complex. For example, in protein immunoaffinity chromatography, the antibody may be covalently or non-covalently coupled to a matrix such as Sepharose in, e.g., a column. The tissue sample or cell lysate from the recombinant cells can then be contacted with the antibody on the matrix. The column is then washed with a low-salt solution to wash off the unbound components. The protein complexes that are retained in the column can be then eluted from the column using a high-salt solution, a competitive antigen of the antibody, a chaotropic solvent, or sodium dodecyl sulfate (SDS), or the like. In immunoblotting, crude proteins samples from a tissue sample or recombinant host cell lysate can be fractionated on a polyacrylamide gel electrophoresis (PAGE) and then transferred to, e.g., a nitrocellulose membrane. The location of the protein complex on the membrane may be identified using a specific antibody, and the protein complex is subsequently isolated.

In another embodiment, individual interacting protein partners may be isolated or purified independently from tissue samples or recombinant host cells using similar methods as described above. The individual interacting protein partners are then contacted with each other under conditions conducive to the interaction therebetween thus forming a protein complex of the present invention. It is noted that different protein-protein interactions may require different conditions. As a starting point, for example, a buffer having 20 mM Tris-HCl, pH 7.0 and 500 mM NaCl may be used. Several different parameters may be varied, including temperature, pH, salt concentration, reducing agent, and the like. Some minor degree of experimentation may be required to determine the optimum incubation condition, this being well within the capability of one skilled in the art once apprised of the present disclosure.

In yet another embodiment, the protein complex of the present invention may be prepared from tissue samples or recombinant host cells or other suitable sources by protein affinity chromatography or affinity blotting. That is, one of the interacting protein partners is used to isolate the other interacting protein partner(s) by binding affinity thus forming protein complexes. Thus, an interacting protein partner prepared by purification from tissue samples or by recombinant expression or chemical synthesis may be bound covalently or non-covalently to a matrix such as Sepharose in, e.g., a chromatography column. The tissue sample or cell lysate from the recombinant cells can then be contacted with the bound protein on the matrix. A low-salt solution is used to wash off the unbound components, and a high-salt solution is then employed to elute the bound protein complexes in the column. In affinity blotting, crude protein samples from a tissue sample or recombinant host cell lysate can be fractionated on a polyacrylamide gel electrophoresis (PAGE) and then transferred to, e.g., a nitrocellulose membrane. The purified interacting protein member is then bound to its interacting protein partner(s) on the membrane forming protein complexes, which are then isolated from the membrane.

It will be apparent to skilled artisans that any recombinant expression methods may be used in the present invention for purposes of recombinantly expressing the protein complexes or individual interacting proteins. Generally, a nucleic acid encoding an interacting protein member can be introduced into a suitable host cell. For purposes of recombinantly forming a protein complex within a host cell, nucleic acids encoding two or more interacting protein members should be introduced into the host cell.

Typically, the nucleic acids, preferably in the form of DNA, are incorporated into a vector to form expression vectors capable of expressing the interacting protein member(s) once introduced into a host cell. Many types of vectors can be used for the present invention. Methods for the construction of an expression vector for purposes of this invention should be apparent to skilled artisans apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516–544 (1987); *The Molecular Biology of the Yeast Saccharomyces*, Eds. Strathern et al., Cold Spring Harbor Press, Vols. I and II, 1982; and Sambrook et al., *Molecular Cloning: A Laboratory Manual*, Cold Spring Harbor Press, 1989.

Generally, the expression vectors may include a promoter operably linked to a DNA encoding an interacting protein member, an origin of DNA replication for the replication of the vectors in host cells. Preferably, the expression vectors also include a replication origin for the amplification of the vectors in, e.g., *E. coli*, and selection marker(s) for selecting and maintaining only those host cells harboring the expression vectors. Additionally, the expression vectors preferably also contain inducible elements, which function to control the transcription from the DNA encoding an interacting protein member. Other regulatory sequences such as transcriptional enhancer sequences and translation regulation sequences (e.g., Shine-Dalgarno sequence) can also be operably included. Termination sequences such as the polyadenylation signals from bovine growth hormone, SV40, lacZ and AcMNPV polyhedral protein genes may also be operably linked to the DNA encoding an interacting protein member. An epitope tag coding sequence for detection and/or purification of the expressed protein can also be operably incorporated into the expression vectors. Examples of useful epitope tags include, but are not limited to, influenza virus hemagglutinin (HA), Simian Virus 5 (V5), polyhistidine (6xHis), c-myc, lacZ, GST, and the like. Proteins with polyhistidine tags can be easily detected and/or purified with Ni affinity columns, while specific antibodies immunoreactive with many epitope tags are generally commercially available. The expression vectors may also contain components that direct the expressed protein extracellularly or to a particular intracellular compartment. Signal peptides, nuclear localization sequences, endoplasmic reticulum retention signals, mitochondrial localization sequences, myristoylation signals, palmitoylation signals, and transmembrane sequences are example of optional vector components that can determine the destination of expressed proteins. When it is desirable to express two or more interacting protein members in a single host cell, the DNA fragments encoding the interacting protein members may be incorporated into a single vector or different vectors.

The thus constructed expression vectors can be introduced into the host cells by any techniques known in the art, e.g., by direct DNA transformation, microinjection, electroporation, viral infection, lipofection, gene gun, and the like. The expression of the interacting protein members may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. The vector construct can be designed to be suitable for expression in various host cells, including but not limited to bacteria, yeast cells, plant cells, insect cells, and mammalian and human cells. Methods for preparing expression vectors for expression in different host cells should be apparent to a skilled artisan.

Homologues and fragments of the native interacting protein members can also be easily expressed using the recombinant methods described above. For example, to express a protein fragment, the DNA fragment incorporated into the expression vector can be selected such that it only encodes the protein fragment. Likewise, a specific hybrid protein can be expressed using a recombinant DNA encoding the hybrid protein. Similarly, a homologue protein may be expressed from a DNA sequence encoding the homologue protein or protein fragment. A homologue-encoding DNA sequence may be obtained by manipulating the native protein-encoding sequence using recombinant DNA techniques. For this purpose, random or site-directed mutagenesis can be conducted using techniques generally known in the art. To make protein derivatives, for example, the amino acid sequence of a native interacting protein member may be changed in predetermined manners by site-directed DNA mutagenesis to create or remove consensus sequences for, e g., phosphorylation by protein kinases, glycosylation, ribosylation, myristolation, palmytoylation, and the like. Alternatively, non-natural amino acids can be incorporated into an interacting protein member during the synthesis of the protein in recombinant host cells. For example, photoreactive lysine derivatives can be incorporated into an interacting protein member during translation by using a modified lysyl-tRNA. See, e.g., Wiedmann et al., *Nature,* 328:830–833 (1989); Musch et al., *Cell,* 69:343–352 (1992). Other photoreactive amino acid derivatives can also be incorporated in a similar manner. See, e.g., High et al., *J. Biol. Chem.,* 368:28745–28751 (1993). Indeed, the photoreactive amino acid derivatives thus incorporated into an interacting protein member can function to cross-link the protein to its interacting protein partner in a protein complex under predetermined conditions.

In addition, derivatives of the native interacting protein members of the present invention can also be prepared by chemically linking certain moieties to amino acid side chains of the native proteins.

If desired, the homologues and derivatives thus generated can be tested to determine whether they are capable of interacting with their intended interacting partners to form protein complexes. Testing can be conducted by e.g., the yeast two-hybrid system or other methods known in the art for detecting protein-protein interaction.

A hybrid protein as described above having Tsg101 or a homologue, derivative, or fragment thereof covalently linked by a peptide bond or a peptide linker to HIV GAGp6 or a homologue, derivative, or fragment thereof, can be expressed recombinantly from a chimeric nucleic acid, e.g., a DNA or MRNA fragment encoding the fusion protein. Accordingly, the present invention also provides a nucleic acid encoding the hybrid protein of the present invention. In addition, an expression vector having incorporated therein a nucleic acid encoding the hybrid protein of the present invention is also provided. The methods for making such chimeric nucleic acids and expression vectors containing them should be apparent to skilled artisans apprised of the present disclosure.

2.5. Protein Microchip

In accordance with another embodiment of the present invention, a protein microchip or microarray is provided having one or more of the protein complexes and/or antibodies selectively immunoreactive with the protein complexes of the present invention. Protein microarrays are becoming increasingly important in both proteomics research and protein-based detection and diagnosis of diseases. The protein microarrays in accordance with this embodiment of the present invention will be useful in a variety of applications including, e.g., large-scale or high-throughput screening for compounds capable of binding to the protein complexes or modulating the interactions between the interacting protein members in the protein complexes.

The protein microarray of the present invention can be prepared in a number of methods known in the art. An example of a suitable method is that disclosed in MacBeath and Schreiber, *Science,* 289:1760–1763 (2000). Essentially, glass microscope slides are treated with an aldehyde-containing silane reagent (SuperAldehyde Substrates purchased from TeleChem International, Cupertino, Calif.). Nanoliter volumes of protein samples in a phophate-buffered saline with 40% glycerol are then spotted onto the treated slides using a high-precision contact-printing robot. After incubation, the slides are immersed in a bovine serum albumin (BSA)-containing buffer to quench the unreacted aldehydes and to form a BSA layer which functions to prevent non-specific protein binding in subsequent applications of the microchip. Alternatively, as disclosed in MacBeath and Schreiber, proteins or protein complexes of the present invention can be attached to a BSA-NHS slide by covalent linkages. BSA-NHS slides are fabricated by first attaching a molecular layer of BSA to the surface of glass slides and then activating the BSA with N,N'-disuccinimidyl carbonate. As a result, the amino groups of the lysine, asparate, and glutamate residues on the BSA are activated and can form covalent urea or amide linkages with protein samples spotted on the slides. See MacBeath and Schreiber, *Science*, 289:1760–1763 (2000).

Another example of useful method for preparing the protein microchip of the present invention is that disclosed in PCT Publication Nos. WO 00/4389A2 and WO 00/04382, both of which are assigned to Zyomyx and are incorporated herein by reference. First, a substrate or chip base is covered with one or more layers of thin organic film to eliminate any surface defects, insulate proteins from the base materials, and to ensure uniform protein array. Next, a plurality of protein-capturing agents (e.g., antibodies, peptides, etc.) are arrayed and attached to the base that is covered with the thin film. Proteins or protein complexes can then be bound to the capturing agents forming a protein microarray. The protein microchips are kept in flow chambers with an aqueous solution.

The protein microarray of the present invention can also be made by the method disclosed in PCT Publication No. WO 99/36576 assigned to Packard Bioscience Company, which is incorporated herein by reference. For example, a three-dimensional hydrophilic polymer matrix, i.e., a gel, is first disposed on a solid substrate such as a glass slide. The polymer matrix gel is capable of expanding or contracting and contains a coupling reagent that reacts with amine groups. Thus, proteins and protein complexes can be contacted with the matrix gel in an expanded aqueous and porous state to allow reactions between the amine groups on the protein or protein complexes with the coupling reagents thus immobilizing the proteins and protein complexes on the substrate. Thereafter, the gel is contracted to embed the attached proteins and protein complexes in the matrix gel.

Alternatively, the proteins and protein complexes of the present invention can be incorporated into a commercially available protein microchip, e.g., the ProteinChip System from Ciphergen Biosystems Inc., Palo Alto, Calif. The ProteinChip System comprises metal chips having a treated surface, which interact with proteins. Basically, a metal chip surface is coated with a silicon dioxide film. The molecules of interest such as proteins and protein complexes can then be attached covalently to the chip surface via a silane coupling agent.

The protein microchips of the present invention can also be prepared with other methods known in the art, e.g., those disclosed in U.S. Pat. Nos. 6,087,102, 6,139,831, 6,087,103; PCT Publication Nos. WO 99/60156, WO 99/39210, WO 00/54046, WO 00/53625, WO 99/51773, WO 99/35289, WO 97/42507, WO 01/01142, WO 00/63694, WO 00/61806, WO 99/61148, WO 99/40434, all of which are incorporated herein by reference.

3. Antibodies

In accordance with another aspect of the present invention, an antibody immunoreactive against a protein complex of the present invention is provided. In one embodiment, the antibody is selectively immunoreactive with a protein complex of the present invention. Specifically, the phrase "selectively immunoreactive with a protein complex" as used herein means that the immunoreactivity of the antibody of the present invention with the protein complex is substantially higher than that with the individual interacting members of the protein complex so that the binding of the antibody to the protein complex is readily distinguishable from the binding of the antibody to the individual interacting member proteins based on the strength of the binding affinities. Preferably, the binding constant differs by a magnitude of at least 2 fold, more preferably at least 5 fold, even more preferably at least 10 fold, and most preferably at least 100 fold. In a specific embodiment, the antibody is not substantially immunoreactive with the interacting protein members of the protein complex.

The antibody of the present invention can be readily prepared using procedures generally known in the art. See, e.g., Harlow and Lane, Antibodies: A Laboratory Manual, Cold Spring Harbor Press, 1988. Typically, the protein complex against which the antibody to be generated will be immunoreactive is used as the antigen for the purpose of producing immune response in a host animal. In one embodiment, the protein complex used consists the native proteins. Preferably, the protein complex includes only the binding domains of Tsg101 and HIV GAGp6, respectively. As a result, a greater portion of the total antibodies may be selectively immunoreactive with the protein complexes. The binding domains can be selected from, e.g., those summarized in Table 1. In addition, various techniques known in the art for predicting epitopes may also be employed to design antigenic peptides based on the interacting protein members in a protein complex of the present invention to increase the possibility of producing an antibody selectively immunoreactive with the protein complex. Suitable epitope-prediction computer programs include, e.g., MacVector from International Biotechnologies, Inc. and Protean from DNAStar.

In a specific embodiment, a hybrid protein as described above in Section 2.3 is used as an antigen which has Tsg101 or a homologues, derivative, or fragment thereof covalently linked by a peptide bond or a peptide linker to HIV GAGp6 or a homologue, derivative, or fragment thereof. In a preferred embodiment, the hybrid protein consists of two interacting binding domains selected from Table 1, or homologues or derivatives thereof, covalently linked together by a peptide bond or a linker molecule.

The antibody of the present invention can be a polyclonal antibody to a protein complex of the present invention. To produce the polyclonal antibody, various animal hosts can be employed, including, e.g., mice, rats, rabbits, goats, guinea pigs, hamsters, etc. A suitable antigen which is a protein complex of the present invention or a derivative thereof as described above can be administered directly to a host animal to illicit immune reactions. Alternatively, it can be administered together with a carrier such as keyhole limpet hemocyanin (KLH), bovine serum albumin (BSA), ovalbumin, and Tetanus toxoid. Optionally, the antigen is conjugated to a carrier by a coupling agent such as carbodiimide, glutaraldehyde, and MBS. Any conventional adjuvants may be used to boost the immune response of the host animal to the protein complex antigen. Suitable adjuvants known in the art include but are not limited to Complete Freund's Adjuvant (which contains killed mycobacterial cells and mineral oil), incomplete Freund's Adjuvant (which lacks the cellular components), aluminum salts, MF59 from Biocine, monophospholipid, synthetic trehalose dicorynomycolate (TDM) and cell wall skeleton (CWS) both from RIBI ImmunoChem Research Inc., Hamilton, Mont., non-ionic surfactant vesicles (NISV) from Proteus International PLC, Cheshire, U.K., and saponins. The antigen preparation can be administered to a host animal by subcutaneous, intramuscular, intravenous, intradermal, or intraperitoneal injection, or by injection into a lymphoid organ.

The antibodies of the present invention may also be monoclonal. Such monoclonal antibodies may be developed using any conventional techniques known in the art. For example, the popular hybridoma method disclosed in Kohler and Milstein, *Nature*, 256:495–497 (1975) is now a well-developed technique that can be used in the present invention. See U.S. Pat. No. 4,376,110, which is incorporated herein by reference. Essentially, B-lymphocytes producing a polyclonal antibody against a protein complex of the present invention can be fused with myeloma cells to generate a library of hybridoma clones. The hybridoma population is then screened for antigen binding specificity and also for immunoglobulin class (isotype). In this manner, pure hybridoma clones producing specific homogenous antibodies can be selected. See generally, Harlow and Lane, *Antibodies: A Laboratory Manual*, Cold Spring Harbor Press, 1988. Alternatively, other techniques known in the art may also be used to prepare monoclonal antibodies, which include but are not limited to the EBV hybridoma technique, the human N-cell hybridoma technique, and the trioma technique.

In addition, antibodies selectively immunoreactive with a protein complex of the present invention may also be recombinantly produced. For example, cDNAs prepared by PCR amplification from activated B-lymphocytes or hybridomas may be cloned into an expression vector to form a cDNA library, which is then introduced into a host cell for recombinant expression. The cDNA encoding a specific desired protein may then be isolated from the library. The isolated cDNA can be introduced into a suitable host cell for the expression of the protein. Thus, recombinant techniques can be used to recombinantly produce specific native antibodies, hybrid antibodies capable of simultaneous reaction with more than one antigen, chimeric antibodies (e.g., the constant and variable regions are derived from different sources), univalent antibodies which comprise one heavy and light chain pair coupled with the Fc region of a third (heavy) chain, Fab proteins, and the like. See U.S. Pat. No. 4,816,567; European Patent Publication No. 0088994; Munro, *Nature*, 312:597 (1984); Morrison, *Science*, 229: 1202 (1985); Oi et al., *BioTechniques*, 4:214 (1986); and Wood et al., *Nature*, 314:446–449 (1985), all of which are incorporated herein by reference. Antibody fragments such as Fv fragments, single-chain Fv fragments (scFv), Fab' fragments, and F(ab')$_2$ fragments can also be recombinantly produced by methods disclosed in, e.g., U.S. Pat. No. 4,946,778; Skerra & Plückthun, *Science*, 240:1038–1041 (1988); Better et al., *Science*, 240:1041-1043 (1988); and Bird, et al., *Science*, 242:423–426 (1988), all of which are incorporated herein by reference.

In a preferred embodiment, the antibodies provided in accordance with the present invention are partially or fully humanized antibodies. For this purpose, any methods known in the art may be used. For example, partially humanized chimeric antibodies having V regions derived from the tumor-specific mouse monoclonal antibody, but human C regions are disclosed in Morrison and Oi, *Adv. Immunol.*, 44:65–92 (1989). In addition, fully humanized antibodies can be made using transgenic non-human animals. For example, transgenic non-human animals such as transgenic mice can be produced in which endogenous immunoglobulin genes are suppressed or deleted, while heterologous antibodies are encoded entirely by exogenous immunoglobulin genes, preferably human immunoglobulin genes, recombinantly introduced into the genome. See e.g., U.S. Pat. Nos. 5,530,101; 5,545,806; 6,075,181; PCT Publication No. WO 94/02602; Green et. al., *Nat. Genetics*, 7: 13–21 (1994); and Lonberg et al., *Nature* 368: 856–859 (1994), all of which are incorporated herein by reference. The transgenic non-human host animal may be immunized with suitable antigens such as a protein complex of the present invention or one or more of the interacting protein members thereof to illicit specific immune response thus producing humanized antibodies. In addition, cell lines producing specific humanized antibodies can also be derived from the immunized transgenic non-human animals. For example, mature B-lymphocytes obtained from a transgenic animal producing humanized antibodies can be fused to myeloma cells and the resulting hybridoma clones may be selected for specific humanized antibodies with desired binding specificities. Alternatively, cDNAs may be extracted from mature B-lymphocytes and used in establishing a library which is subsequently screened for clones encoding humanized antibodies with desired binding specificities.

In yet another embodiment, a bifunctional antibody is provided which has two different antigen binding sites, each being specific to a different interacting protein member in a protein complex of the present invention. The bifunctional antibody may be produced using a variety of methods known in the art. For example, two different monoclonal antibody-producing hybridomas can be fused together. One of the two hybridomas may produce a monoclonal antibody specific against an interacting protein member of a protein complex of the present invention, while the other hybridoma generates a monoclonal antibody immunoreactive with another interacting protein member of the protein complex. The thus formed new hybridoma produces different antibodies including a desired bifunctional antibody, i.e., an antibody immunoreactive with both of the interacting protein members. The bifunctional antibody can be readily purified. See Milstein and Cuello, *Nature*, 305:537–540 (1983).

Alternatively, a bifunctional antibody may also be produced using heterobifunctional crosslinkers to chemically link two different monoclonal antibodies, each being immunoreactive with a different interacting protein member of a protein complex. Therefore, the aggregate will bind to two interacting protein members of the protein complex. See Staerz et al, *Nature*, 314:628–631(1985); Perez et al, *Nature*, 316:354–356 (1985).

In addition, bifunctional antibodies can also be produced by recombinantly expressing light and heavy chain genes in a hybridoma that itself produces a monoclonal antibody. As a result, a mixture of antibodies including a bifunctional antibody is produced. See DeMonte et al, *Proc. Natl. Acad. Sci., USA*, 87:2941–2945 (1990); Lenz and Weidle, *Gene*, 87:213–218 (1990).

Preferably, a bifunctional antibody in accordance with the present invention is produced by the method disclosed in U.S. Pat. No. 5,582,996, which is incorporated herein by reference. For example, two different Fabs can be provided and mixed together. The first Fab can bind to an interacting protein member of a protein complex, and has a heavy chain constant region having a first complementary domain not naturally present in the Fab but capable of binding a second complementary domain. The second Fab is capable of binding another interacting protein member of the protein complex, and has a heavy chain constant region comprising a second complementary domain not naturally present in the Fab but capable of binding to the first complementary domain. Each of the two complementary domains is capable of stably binding to the other but not to itself. For example, the leucine zipper regions of c-fos and c-jun oncogenes may be used as the first and second complementary domains. As a result, the first and second complementary domains interact with each other to form a leucine zipper thus associating the two different Fabs into a single antibody construct capable of binding to two antigenic sites.

Other suitable methods known in the art for producing bifunctional antibodies may also be used, which include those disclosed in Holliger et al., *Proc. Nat'l Acad. Sci. USA*, 90:6444–6448 (1993); de Kruif et al., *J. Biol. Chem.*, 271:7630–7634 (1996); Coloma and Morrison, *Nat. Biotechnol.*, 15:159–163 (1997); Muller et al., *FEBS Lett.*, 422:259–264 (1998); and Muller et al., *FEBS Lett.*, 432: 45–49 (1998), all of which are incorporated herein by reference.

4. Screening Assays

The present invention encompasses a method for selecting modulators of an interaction between a first protein and a second protein, wherein the first protein is (i) Tsg101, (ii) a Tsg101 protein homologue having an amino acid sequence at least 90% identical to that of Tsg101 and capable of interacting with HIV GAGp6, (iii) a Tsg101 protein fragment containing the Tsg101 UEV domain, or (iv) a fusion protein containing said Tsg101 protein, said Tsg101 protein homologue or said Tsg101 protein fragment; and wherein the second protein is (1) a retrovirus GAG polypeptide having the P(T/S)AP late domain motif, (2) a homologue of said retrovirus GAG polypeptide, said homologue having an amino acid sequence at least 90% identical to that of said retrovirus GAG polypeptide and capable of interacting with Tsg101, (3) a fragment of said retrovirus GAG polypeptide, said fragment being capable of interacting with Tsg101, or (4) a fusion protein containing said retrovirus Gag polypeptide, said retrovirus GAG polypeptide homologue or said retrovirus GAG polypeptide fragment. In a specific embodiment, the second protein is (1) HIV GAG polypeptide, (2) a HIV GAG polypeptide homologue having an amino acid sequence at least 90% identical to that of HIV GAG polypeptide and capable of interacting with Tsg101, (3) HIV GAGp6 protein, (4) a HIV GAGp6 homologue having an amino acid sequence at least 90% identical to that of HIV GAGp6 polypeptide and capable of interacting with Tsg101, (5) a HIV GAGp6 fragment capable of interacting with Tsg101, and (6) a fusion protein containing said HIV GAG polypeptide, said HIV GAG polypeptide homologue, said HIV GAGp6 protein, said HIV GAGp6 homologue or said HIV GAgp6 fragment.

The protein complexes of the present invention, Tsg101 and HIV GAGp6 can be used in screening assays to select modulators of Tsg101, HIV GAGp6, and protein complexes of the present invention. In addition, homologues, derivatives and fragments of Tsg101, HIV GAGp6, and protein complexes containing such homologues, derivatives and fragments may also be used in the screening assays. As used herein, the term "modulator" encompasses any compounds that can cause any forms of alteration of the properties, biological activities or functions of the proteins or protein complexes, including, e.g., enhancing or reducing their biological activities, increasing or decreasing their stability, altering their affinity or specificity to certain other biological molecules, etc. In addition, the term "modulator" as used herein also includes any compounds that simply bind Tsg101, HIV GAGp6, and/or the proteins complexes of the present invention. For example, a modulator can be a an interaction antagonist capable of interfering with, or disrupting or dissociating protein-protein interaction between Tsg101 or a homologue or derivative thereof and HIV GAGp6 or a homologue or derivative thereof.

The term "interaction antagonist" as used herein means a compound that interferes with, blocks, disrupts or destabilizes a protein-protein interaction; blocks or interferes with the formation of a protein complex; or destabilizes, disrupts or dissociates an existing protein complex.

The term "interaction agonist" as used herein means a compound that triggers, initiates, propagates, nucleates, or otherwise enhances the formation of a protein-protein interaction; triggers, initiates, propagates, nucleates, or otherwise enhances the formation of a protein complex; or stabilizes an existing protein complex.

Accordingly, the present invention provides screening methods for selecting modulators of Tsg101 or HIV GAGp6 or a mutant form thereof, or a protein complex formed between Tsg101 or or a homologue or derivative or fragment thereof and HIV GAGp6 or a homologue or derivative or fragment thereof. The targets suitable in the screening methods of the present invention may include any embodiments of the protein complexes of the present invention as described in Section 2. Preferably, protein fragments are used in forming the protein complexes. For example, a preferred target protein complex can include a Tsg101 protein fragment including the UEV domain. Also for example, the HIV GAGp6 or a fragment thereof may be used in forming a target protein complex. In a specific embodiment, a polypeptide including the first 14 amino acids of the HIV GAGp6 is used in forming a target protein complex. In another embodiment, fusion proteins are used in which a detectable epitope tag is fused to a Tsg101 protein or a homologue or derivative or fragment thereof and/or to a HIV GAGp6 polypeptide or a homologue or derivative or fragment thereof. Suitable examples of such epitope tags include sequences derived from, e.g., influenza virus hemagglutinin (HA), Simian Virus 5 (V5), polyhistidine (6xHis), c-myc, lacZ, GST, and the like.

When Tsg101 protein or a homologue or derivative or fragment thereof is used as a target protein in the screening methods of the present invention, preferably the Tsg101UEV domain is included in the Tsg101 protein or a homologue or derivative or fragment thereof. And preferably the Tsg101 protein or a homologue or derivative or fragment thereof is fused to a detectable tag such as sequences derived from, e.g., influenza virus hemagglutinin (HA), Simian Virus 5 (V5), polyhistidine (6× His), c-myc, lacZ, GST, and the like. In this respect, compounds selected by the methods capable of binding to Tsg101 protein, preferably the UEV domain of Tsg101 protein can be tested for their ability to inhibit or interfere with the interactions between Tsg101 and HIV GAGp6. They can also be tested for their ability to inhibit HIV viral budding or HIV propagation. Suitable methods for such testing should be apparent to skilled artisan apprised of the present disclosure.

The modulators selected in accordance with the screening methods of the present invention can be effective in modulating the functions or activities of Tsg101, HIV GAGp6, or the protein complexes of the present invention. For example, compounds capable of binding the protein complexes may be capable of modulating the functions of the protein complexes. Additionally, compounds that interfere with, weaken, dissociate or disrupt, or alternatively, initiate, facilitate or stabilize the protein-protein interaction between the interacting protein members of the protein complexes can also be effective in modulating the functions or activities of the protein complexes. Thus, the compounds identified in the screening methods of the present invention can be made into therapeutically or prophylactically effective drugs for preventing or ameliorating diseases, disorders or symptoms caused by or associated with the protein complexes or Tsg101 or HIV GAGp6 of the present invention. Alternatively, they may be used as leads to aid the design and identification of therapeutically or prophylactically effective compounds for diseases, disorders or symptoms caused by or associated with the protein complexes or Tsg101 or HIV GAGp6 of the present invention. The protein complexes and/or interacting protein members thereof in accordance with the present invention can be used in any of a variety of drug screening techniques. Drug screening can be performed as described herein or using well-known techniques, such as those described in U.S. Pat. Nos. 5,800,998 and 5,891,628, both of which are incorporated herein by reference.

4.1. Test Compounds

Any test compounds may be screened in the screening assays of the present invention to select modulators of Tsg101, a Tsg101-containing protein complex and/or HIV GAGp6 of the present invention. By the term "selecting" or "select" modulators it is intended to encompass both (a) choosing compounds from a group previously unknown to be modulators of Tsg101, a Tsg101-containing protein complex and/or HIV GAGp6 of the present invention, and (b) testing compounds that are known to be capable of binding, or modulating the functions and activities of, Tsg101, a Tsg101-containing protein complex and/or HIV GAGp6 of the present invention. Both types of compounds are generally referred to herein as "test compounds." The test compounds may include, by way of example, proteins (e.g., antibodies, small peptides, artificial or natural proteins), nucleic acids, and derivatives, mimetics and analogs thereof, and small organic molecules having a molecular weight of no greater than 10,000 daltons, more preferably less than 5,000 daltons. Preferably, the test compounds are provided in library formats known in the art, e.g., in chemically synthesized libraries, recombinant expression libraries (e.g., phage display libraries), and in vitro translation-based libraries (e.g., ribosome display libraries).

For example, the screening assays of the present invention can be used in the antibody production processes described in Section 3 to select antibodies with desirable specificities. Various forms antibodies or derivatives thereof may be screened, including but not limited to, polyclonal antibodies, monoclonal antibodies, bifunctional antibodies, chimeric antibodies, single chain antibodies, antibody fragments such as Fv fragments, single-chain Fv fragments (scFv), Fab' fragments, and F(ab')$_2$ fragments, and various modified forms of antibodies such as catalytic antibodies, and antibodies conjugated to toxins or drugs, and the like. The antibodies can be of any types such as IgG, IgE, IgA, or IgM. Humanized antibodies are particularly preferred. Preferably, the various antibodies and antibody fragments may be provided in libraries to allow large-scale high throughput screening. For example, expression libraries expressing antibodies or antibody fragments may be constructed by a method disclosed, e.g., in Huse et al., *Science,* 246:1275–1281 (1989), which is incorporated herein by reference. Single-chain Fv (scFv) antibodies are of particular interest in diagnostic and therapeutic applications. Methods for providing antibody libraries are also provided in U.S. Pat. Nos. 6,096,551; 5,844,093; 5,837,460; 5,789,208; and 5,667,988, all of which are incorporated herein by reference.

Peptidic test compounds may be peptides having L-amino acids and/or D-amino acids, phosphopeptides, and other types of peptides. The screened peptides can be of any size, but preferably have less than about 50 amino acids. Smaller peptides are easier to deliver into a patient's body. Various forms of modified peptides may also be screened. Like antibodies, peptides can also be provided in, e.g., combinatorial libraries. See generally, Gallop et al., *J. Med. Chem.,* 37:1233–1251 (1994). Methods for making random peptide libraries are disclosed in, e.g., Devlin et al., *Science,* 249:404–406 (1990). Other suitable methods for constructing peptide libraries and screening peptides therefrom are disclosed in, e.g., Scott and Smith, *Science,* 249:386–390 (1990); Moran et al., *J. Am. Chem. Soc.,* 117:10787–10788 (1995) (a library of electronically tagged synthetic peptides); Stachelhaus et al., *Science,* 269:69–72 (1995); U.S. Pat. Nos. 6,156,511; 6,107,059; 6,015,561; 5,750,344; 5,834,318; 5,750,344, all of which are incorporated herein by reference. For example, random-sequence peptide phage display libraries may be generated by cloning synthetic oligonucleotides into the gene III or gene VIII of an *E. coli,* filamentous phage. The thus generated phage can propagate in *E. coli.* and express peptides encoded by the oligonucleotides as fusion proteins on the surface of the phage. Scott and Smith, *Science,* 249:368–390 (1990). Alternatively, the "peptides on plasmids" method may also be used to form peptide libraries. In this method, random peptides may be fused to the C-terminus of the *E. coli.* Lac repressor by recombinant technologies and expressed from a plasmid that also contains Lac repressor-binding sites. As a result, the peptide fusions bind to the same plasmid that encodes them.

Small organic or inorganic non-peptide non-nucleotide compounds are preferred test compounds for the screening assays of the present invention. They too can be provided in a library format. See generally, Gordan et al. *J. Med. Chem.,* 37:1385–1401 (1994). For example, benzodiazepine libraries are provided in Bunin and Ellman, *J. Am. Chem. Soc.,* 114:10997–10998 (1992), which is incorporated herein by reference. A method for constructing and screening peptoid libraries are disclosed in Simon et al., *Proc. Natl. Acad. Sci. USA,* 89:9367–9371 (1992). Methods for the biosynthesis of novel polyketides in a library format are described in McDaniel et al, Science, 262:1546–1550 (1993) and Kao et al., *Science,* 265:509–512 (1994). Various libraries of small organic molecules and methods of construction thereof are disclosed in U.S. Pat. Nos. 6,162,926 (multiply-substituted fullerene derivatives); U.S. Pat. No. 6,093,798 (hydroxamic acid derivatives); U.S. Pat. No. 5,962,337 (combinatorial 1,4-benzodiazepin-2,5-dione library); U.S. Pat. No. 5,877,278 (Synthesis of N-substituted oligomers); U.S. Pat. No. 5,866,341 (compositions and methods for screening drug libraries); U.S. Pat. No. 5,792,821 (polymerizable cyclodextrin derivatives); U.S. Pat. No. 5,766,963 (hydroxypropylamine library); and U.S. Pat. No. 5,698,685 (morpholinosubunit combinatorial library), all of which are incorporated herein by reference.

Other compounds such as oligonucleotides and peptide nucleic acids (PNA), and analogs and derivatives thereof may also be screened to select clinically useful compounds. Combinatorial libraries of oligos are also known in the art. See Gold et al., *J. Biol. Chem.,* 270:13581–13584 (1995).

4.2. In vitro Screening Assays

The test compounds may be screened in an in vitro assay to select compounds capable of binding the protein complexes or interacting protein members thereof in accordance with the present invention. For this purpose, a test compound is contacted with a protein complex or an interacting protein member thereof under conditions and for a time sufficient to allow specific interaction between the test compound and the target components to occur and thus binding of the compound to the target forming a complex.

Subsequently, the binding event is detected.

Various screening techniques known in the art may be used in the present invention. The protein complexes and the interacting protein members thereof may be prepared by any suitable methods, e.g., by recombinant expression and purification. The protein complexes and/or interacting protein members thereof (both are referred to as "target" hereinafter in this section) may be free in solution or in cell extracts. A test compound may be mixed with a target forming a liquid mixture. The compound may be labeled with a detectable marker. Upon mixing under suitable conditions, the binding complex having the compound and the target may be co-immunoprecipitated and washed. The compound in the precipitated complex may be detected based on the marker on the compound.

In a preferred embodiment, the target is immobilized on a solid support or on a cell surface. Preferably, the target can be arrayed into a protein microchip in a method described in Section 2.4. For example, a target may be immobilized directly onto a microchip substrate such as glass slides or onto a multi-well plates using non-neutralizing antibodies, i.e., antibodies capable of binding to the target but do not substantially affect its biological activities. To effect the screening, test compounds can be contacted with the immobilized target to allow binding to occur to form complexes under standard binding assay conditions. Either the targets or test compounds are labeled with a detectable marker using well-known labeling techniques. For example, U.S. Pat. No. 5,741,713 discloses combinatorial libraries of biochemical compounds labeled with NMR active isotopes. To select binding compounds, one may measure the formation of the target-test compound complexes or kinetics for the formation thereof. When combinatorial libraries of organic non-peptide non-nucleic acid compound are screened, it is preferred that labeled or encoded (or "tagged") combinatorial libraries are used to allow rapid decoding of lead structures. This is especially important because, unlike biological libraries, individual compounds found in chemical libraries cannot be amplified by self-amplification. Tagged combinatorial libraries are provided in, e.g., Borchardt and Still, *J. Am. Chem. Soc.*, 116:373–374 (1994) and Moran et al., *J. Am. Chem. Soc.*, 117:10787–10788 (1995), both of which are incorporated herein by reference.

Alternatively, the test compounds can be immobilized on a solid support, e.g., forming a microarray of test compounds. The target protein or protein complex is then contacted with the test compounds. The target may be labeled with any suitable detection marker. For example, the target may be labeled with radioactive isotopes or fluorescence marker before binding reaction occurs. Alternatively, after the binding reactions, antibodies that are immunoreactive with the target and are labeled with radioactive materials, fluorescence markers, enzymes, or labeled secondary anti-Ig antibodies may be used to detect any bound target thus selecting the binding compound. One example of this embodiment is the protein probing method. That is, the target provided in accordance with the present invention is used as a probe to screen expression libraries of proteins or random peptides. The expression libraries can be phage display libraries, in vitro translation-based libraries, or ordinary expression cDNA libraries. The libraries may be immobilized on a solid support such as nitrocellulose filters. See e.g., Sikela and Hahn, *Proc. Natl. Acad. Sci. USA*, 84:3038–3042 (1987). The probe may be labeled by a radioactive isotope or a fluorescence marker. Alternatively, the probe can be biotinylated and detected with a streptavidin-alkaline phosphatase conjugate. More conveniently, the bound probe may be detected with an antibody.

In yet another embodiment, a known ligand capable of binding to the target can be used in competitive binding assays. Complexes between the known ligand and the target can be formed and then contacted with test compounds. The ability of a test compound to interfere with the interaction between the target and the known ligand is measured. One exemplary ligand is an antibody capable of specifically binding the target. Particularly, such an antibody is especially useful for identifying peptides that share one or more antigenic determinants of the target protein complex or interacting protein members thereof.

In a specific embodiment, a protein complex used in the screening assay includes a hybrid protein as described in Section 2.3, which is formed by fusion of two interacting protein members or fragments or domains thereof. The hybrid protein may also be designed such that it contains a detectable epitope tag fused thereto. Suitable examples of such epitope tags include sequences derived from, e.g., influenza virus hemagglutinin (HA), Simian Virus 5 (VS), polyhistidine (6× His), c-myc, lacZ, GST, and the like.

Test compounds may also be screened in an in vitro assay to select interaction antagonists of the protein complexes identified in accordance with the present invention. Thus, for example, a Tsg101-HIV GAGp6 protein complex can be contacted with a test compound and disruption or destabilization of the protein complex can be detected.

The assay can be conducted in similar manners as the binding assays described above. For example, the presence or absence of a particular protein complex can be detected by an antibody selectively immunoreactive with the protein complex. Thus, after incubation of the protein complex with a test compound, immunoprecipitation assay can be conducted with the antibody. If the test compound disrupts the protein complex, then the amount of immunoprecipitated protein complex in this assay will be significantly less than that in a control assay in which the same protein complex is not contacted with the test compound. Various other detection methods may be suitable in the dissociation assay, as will be apparent to skilled artisan apprised of the present disclosure. In one embodiment, one of the interacting partner with a detectable marker fused thereto is fixed to a solid support. For example, a GST-GAGp6 fusion protein is attached to a solid support. Then the other interacting partner with a detectable marker fused thereto (e.g., a myc-tagged Tsg101 fragment containing the UEV domain) is contacted with the immobilized first interacting partner in the presence of one or more test compounds. If binding between the two interacting partners occurs, the myc-tagged Tsg101 fragment is also immobilized, which can be detected using an anti-myc antibody after the binding reaction mixture is washed to remove unbound myc-tagged Tsg101 fragment.

4.3. In vivo Screening Assays

Test compounds can also be screened in any in vivo assays to select modulators of the protein complexes or interacting protein members thereof in accordance with the present invention. For example, any in vivo assays known in the art useful in selecting compounds capable of strengthening or interfering with the stability of the protein complexes of the present invention may be used.

4.3.1. Two-Hybrid Assays

In a preferred embodiment, one of the yeast two-hybrid systems or their analogous or derivative forms is used. Examples of suitable two-hybrid systems known in the art include, but are not limited to, those disclosed in U.S. Pat. Nos. 5,283,173; 5,525,490; 5,585,245; 5,637,463; 5,695,941; 5,733,726; 5,776,689; 5,885,779; 5,905,025; 6,037,136; 6,057,101; 6,114,111; and Bartel and Fields, eds., *The Yeast Two-Hybrid System*, Oxford University Press, New York, N.Y., 1997, all of which are incorporated herein by reference.

Typically, in a classic transcription-based two-hybrid assay, two chimeric genes are prepared encoding two fusion proteins: one contains a transcription activation domain fused to an interacting protein member of a protein complex of the present invention or an interacting domain of the interacting protein member, while the other fusion protein includes a DNA binding domain fused to another interacting protein member of the protein complex or an interacting domain thereof. For the purpose of convenience, the two interacting protein members or interacting domains thereof are referred to as "bait fusion protein" and "prey fusion protein," respectively. The chimeric genes encoding the fusion proteins are termed "bait chimeric gene" and "prey chimeric gene," respectively. Typically, a "bait vector" and a "prey vector" are provided for the expression of a bait chimeric gene and a prey chimeric gene, respectively.

4.3.1.1. Vectors

Many types of vectors can be used in a transcription-based two-hybrid assay. Methods for the construction of bait vectors and prey vectors should be apparent to skilled artisans in the art apprised of the present disclosure. See generally, *Current Protocols in Molecular Biology*, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in *Methods in Enzymology* 153:516–544 (1987); *The Molecular Biology of the Yeast Saccharomyces*, Eds. Strathern et al., Cold Spring Harbor Press, Vols. I and II, 1982; and Rothstein in *DNA Cloning: A Practical Approach*, Vol. 11, Ed. DM Glover, IRL Press, Wash., D.C., 1986.

Generally, the bait and prey vectors may include a promoter operably linked to a chimeric gene for the transcription of the chimeric gene, an origin of DNA replication for the replication of the vectors in host cells and a replication origin for the amplification of the vectors in, e.g., *E. coli*, and selection marker(s) for selecting and maintaining only those host cells harboring the vectors. Additionally, the vectors preferably also contain inducible elements, which function to control the expression of a chimeric gene. Making the expression of the chimeric genes inducible and controllable is especially important in the event that the fusion proteins or components thereof are toxic to the host cells. Other regulatory sequences such as transcriptional enhancer sequences and translation regulation sequences (e.g., Shine-Dalgarno sequence) can also be included. Termination sequences such as the bovine growth hormone, SV40, lacZ and AcMNPV polyhedral polyadenylation signals may also be operably linked to a chimeric gene. An epitope tag coding sequence for detection and/or purification of the fusion proteins can also be incorporated into the expression vectors. Examples of useful epitope tags include, but are not limited to, influenza virus hemagglutinin (HA), Simian Virus 5 (V5), polyhistidine (6× His), c-myc, lacZ, GST, and the like. Proteins with polyhistidine tags can be easily detected and/or purified with Ni affinity columns, while specific antibodies to many epitope tags are generally commercially available. The vectors can be introduced into the host cells by any techniques known in the art, e.g., by direct DNA transformation, microinjection, electroporation, viral infection, lipofection, gene gun, and the like. The bait and prey vectors can be maintained in host cells in an extrachromosomal state, i.e., as self-replicating plasmids or viruses. Alternatively, one or both vectors can be integrated into chromosomes of the host cells by conventional techniques such as selection of stable cell lines or site-specific recombination.

The in vivo assays of the present invention can be conducted in many different host cells, including but not limited to bacteria, yeast cells, plant cells, insect cells, and mammalian cells. A skilled artisan will recognize that the designs of the vectors can vary with the host cells used. In one embodiment, the assay is conducted in prokaryotic cells such as *Escherichia coli, Salmonella, Klebsiella, Pseudomonas, Caulobacter*, and *Rhizobium*. Suitable origins of replication for the expression vectors useful in this embodiment of the present invention include, e.g., the ColE1, pSC101, and M13 origins of replication. Examples of suitable promoters include, for example, the T7 promoter, the lacZ promoter, and the like. In addition, inducible promoters are also useful in modulating the expression of the chimeric genes. For example, the lac operon from bacteriophage lambda plac5 is well known in the art and is inducible by the addition of IPTG to the growth medium. Other known inducible promoters useful in a bacteria expression system include pL of bacteriophage λ, the tip promoter, and hybrid promoters such as the tac promoter, and the like.

In addition, selection marker sequences for selecting and maintaining only those prokaryotic cells expressing the desirable fusion proteins should also be incorporated into the expression vectors. Numerous selection markers including auxotrophic markers and antibiotic resistance markers are known in the art and can all be useful for purposes of this invention. For example, the bla gene which confers ampicillin resistance is the most commonly used selection marker in prokaryotic expression vectors. Other suitable markers include genes that confer neomycin, kanamycin, or hygromycin resistance to the host cells. In fact, many vectors are commercially available from vendors such as Invitrogen Corp. of San Diego, Calif., Clontech Corp. of Palo Alto, Calif., BRL of Bethesda, Md., and Promega Corp. of Madison, Wisc. These commercially available vectors, e.g., pBR322, pSPORT, pBluescriptIISK, pcDNAI, and pcDNAII all have a multiple cloning site into which the chimeric genes of the present invention can be conveniently inserted using conventional recombinant techniques. The constructed expression vectors can be introduced into host cells by various transformation or transfection techniques generally known in the art.

In another embodiment, mammalian cells are used as host cells for the expression of the fusion proteins and detection of protein-protein interactions. For this purpose, virtually any mammalian cells can be used including normal tissue cells, stable cell lines, and transformed tumor cells. Conveniently, mammalian cell lines such as CHO cells, Jurkat T cells, NIH 3T3 cells, HEK-293 cells, CV-1 cells, COS-1 cells, HeLa cells, VERO cells, MDCK cells, WI38 cells, and the like are used. Mammalian expression vectors are well known in the art and many are commercially available. Examples of suitable promoters for the transcription of the chimeric genes in mammalian cells include viral transcription promoters derived from adenovirus, simian virus 40 (SV40) (e.g., the early and late promoters of SV40), Rous sarcoma virus (RSV), and cytomegalovirus (CMV) (e.g., CMV immediate-early promoter), human immunodeficiency virus (HIV) (e.g., long terminal repeat (LTR)), vaccinia virus (e.g., 7.5K promoter), and herpes simplex virus (HSV) (e.g., thymidine kinase promoter). Inducible promoters can also be used. Suitable inducible promoters include, for example, the tetracycline responsive element (TRE) (See Gossen et al., *Proc. Natl. Acad. Sci. USA,* 89:5547–5551 (1992)), metallothionein IIA promoter, ecdysone-responsive promoter, and heat shock promoters. Suitable origins of replication for the replication and maintenance of the expression vectors in mammalian cells include, e.g., the Epstein Barr origin of replication in the presence of the Epstein Barr nuclear antigen (see Sugden et al., *Mole. Cell. Biol.,* 5:410–413 (1985)) and the SV40 origin of replication in the presence of the SV40 T antigen (which is present in COS-1 and COS-7 cells) (see Margolskee et al., *Mole. Cell. Biol.,* 8:2837 (1988)). Suitable selection markers include, but are not limited to, genes conferring resistance to neomycin, hygromycin, zeocin, and the like. Many commercially available mammalian expression vectors may be useful for the present invention, including, e.g., pCEP4, pcDNAI, pIND, pSecTag2, pVAX1, pcDNA3.1, and pBI-EGFP, and pDisplay. The vectors can be introduced into mammalian cells using any known techniques such as calcium phosphate precipitation, lipofection, electroporation, and the like. The bait vector and prey vector can be co-transformed into the same cell or, alternatively, introduced into two different cells which are subsequently fused together by cell fusion or other suitable techniques.

Viral expression vectors, which permit introduction of recombinant genes into cells by viral infection, can also be used for the expression of the fusion proteins. Viral expression vectors generally known in the art include viral vectors based on adenovirus, bovine papilloma virus, murine stem cell virus (MSCV), MFG virus, and retrovirus. See Sarver, et al., *Mol. Cell. Biol.,* 1: 486 (1981); Logan & Shenk, *Proc. Natl. Acad. Sci. USA,* 81:3655–3659 (1984); Mackett, et al., *Proc. Natl. Acad. Sci. USA,* 79:7415–7419 (1982); Mackett, et al., *J. Virol.,* 49:857–864 (1984); Panicali, et al., *Proc. Natl. Acad. Sci. USA,* 79:4927–4931 (1982); Cone & Mulligan, *Proc. Natl. Acad. Sci. USA,* 81:6349-6353 (1984); Mann et al., *Cell,* 33:153–159 (1993); Pear et al., *Proc. Natl. Acad. Sci. USA,* 90:8392–8396 (1993); Kitamura et al., *Proc. Natl. Acad. Sci. USA,* 92:9146–9150 (1995); Kinsella et al., *Human Gene Therapy,* 7:1405–1413 (1996); Hofmann et al., *Proc. Natl. Acad. Sci. USA,* 93:5185–5190 (1996); Choate et al., *Human Gene Therapy,* 7:2247 (1996); WO 94/19478; Hawley et al., *Gene Therapy,* 1:136 (1994) and Rivere et al., *Genetics,* 92:6733 (1995), all of which are incorporated by reference.

Generally, to construct a viral vector, a chimeric gene according to the present invention can be operably linked to a suitable promoter. The promoter-chimeric gene construct is then inserted into a non-essential region of the viral vector, typically a modified viral genome. This results in a viable recombinant virus capable of expressing the fusion protein encoded by the chimeric gene in infected host cells. Once in the host cell, the recombinant virus typically is integrated into the genome of the host cell. However, recombinant bovine papilloma viruses typically replicate and remain as extrachromosomal elements.

In another embodiment, the detection assays of the present invention are conducted in plant cell systems. Methods for expressing exogenous proteins in plant cells are well known in the art. See generally, Weissbach & Weissbach, *Methods for Plant Molecular Biology,* Academic Press, NY, 1988; Grierson & Corey, *Plant Molecular Biology,* 2d Ed., Blackie, London, 1988. Recombinant virus expression vectors based on, e.g., cauliflower mosaic virus (CaMV) or tobacco mosaic virus (TMV) can all be used. Alternatively, recombinant plasmid expression vectors such as Ti plasmid vectors and Ri plasmid vectors are also useful. The chimeric genes encoding the fusion proteins of the present invention can be conveniently cloned into the expression vectors and placed under control of a viral promoter such as the 35S RNA and 19S RNA promoters of CaMV or the coat protein promoter of TMV, or of a plant promoter, e.g., the promoter of the small subunit of RUBISCO and heat shock promoters (e.g., soybean hsp17.5-E or hsp17.3-B promoters).

In addition, the in vivo assay of the present invention can also be conducted in insect cells, e.g., *Spodoptera frugiperda* cells, using a baculovirus expression system. Expression vectors and host cells useful in this system are well known in the art and are generally available from various commercial vendors. For example, the chimeric genes of the present invention can be conveniently cloned into a non-essential region (e.g., the polyhedrin gene) of an *Autographa californica* nuclear polyhedrosis virus (AcNPV) vector and placed under control of an AcNPV promoter (e.g., the polyhedrin promoter). The non-occluded recombinant viruses thus generated can be used to infect host cells such as *Spodoptera frugiperda* cells in which the chimeric genes are expressed. See U.S. Pat. No. 4,215,051.

In a preferred embodiment of the present invention, the fusion proteins are expressed in a yeast expression system using yeasts such as *Saccharomyces cerevisiae, Hansenula polymorpha, Pichia pastoris,* and *Schizosaccharomyces pombe* as host cells. The expression of recombinant proteins in yeasts is a well-developed field, and the techniques useful in this respect are disclosed in detail in *The Molecular Biology of the Yeast Saccharomyces,* Eds. Strathern et al., Vols. I and II, Cold Spring Harbor Press, 1982; Ausubel et al., *Current Protocols in Molecular Biology,* New York, Wiley, 1994; and Guthrie and Fink, *Guide to Yeast Genetics and Molecular Biology,* in *Methods in Enzymology, Vol.* 194, 1991, all of which are incorporated herein by reference. Sudbery, *Curr. Opin. Biotech.,* 7:517–524 (1996) reviews the success in the art in expressing recombinant proteins in various yeast species; the entire content and references cited therein are incorporated herein by reference. In addition, Bartel and Fields, eds., *The Yeast Two-Hybrid System,* Oxford University Press, New York, N.Y., 1997 contains extensive discussions of recombinant expression of fusion proteins in yeasts in the context of various yeast two-hybrid systems, and cites numerous relevant references. These and other methods known in the art can all be used for purposes of the present invention. The application of such methods to the present invention should be apparent to a skilled artisan apprised of the present disclosure.

Generally, each of the two chimeric genes is included in a separate expression vector (bait vector and prey vector). Both vectors can be co-transformed into a single yeast host cell. As will be apparent to a skilled artisan, it is also possible to express both chimeric genes from a single vector. In a preferred embodiment, the bait vector and prey vector are introduced into two haploid yeast cells of opposite mating types, e.g., a-type and α-type, respectively. The two haploid cells can be mated at a desired time to form a diploid cell expressing both chimeric genes.

Generally, the bait and prey vectors for recombinant expression in yeast include a yeast replication origin such as the 2μ origin or the ARSH4 sequence for the replication and maintenance of the vectors in yeast cells. Preferably, the vectors also have a bacteria origin of replication (e.g., ColE1) and a bacteria selection marker (e.g., ampR marker, i.e., bla gene). Optionally, the CEN6 centromeric sequence is included to control the replication of the vectors in yeast cells. Any constitutive or inducible promoters capable of driving gene transcription in yeast cells may be employed to control the expression of the chimeric genes. Such promoters are operably linked to the chimeric genes. Examples of suitable constitutive promoters include but are not limited to the yeast ADHI , PGK1, TEF2, GPD1, HIS3, and CYC1 promoters. Example of suitable inducible promoters include but are not limited to the yeast GAL1 (inducible by galactose), CUP1 (inducible by $Cu^{++}$), and FUS I (inducible by pheromone) promoters; the AOX/MOX promoter from *H. polymorpha* and *P. Pastoris* (repressed by glucose or ethanol and induced by methanol); chimeric promoters such as those that contain LexA operators (inducible by LexA-containing transcription factors); and the like. Inducible promoters are preferred when the fusion proteins encoded by the chimeric genes are toxic to the host cells. If it is desirable, certain transcription repressing sequences such as the upstream repressing sequence (URS) from SPO13 promoter can be operably linked to the promoter sequence, e.g., to the 5' end of the promoter region. Such upstream repressing sequences function to fine-tune the expression level of the chimeric genes.

Preferably, a transcriptional termination signal is operably linked to the chimeric genes in the vectors. Generally, transcriptional termination signal sequences derived from, e.g., the CYC1 and ADH1 genes can be used.

Additionally, it is preferred that the bait vector and prey vector contain one or more selectable markers for the selection and maintenance of only those yeast cells that harbor a chimeric gene. Any selectable markers known in the art can be used for purposes of this invention so long as yeast cells expressing the chimeric gene(s) can be positively identified or negatively selected. Examples of markers that can be positively identified are those based on color assays, including the lacZ gene which encodes β-galactosidase, the firefly luciferase gene, secreted alkaline phosphatase, horseradish peroxidase, the blue fluorescent protein (BFP), and the green fluorescent protein (GFP) gene (see Cubitt et al., *Trends Biochem. Sci.*, 20:448–455 (1995)). Other markers emitting fluorescence, chemiluminescence, UV absorption, infrared radiation, and the like can also be used. Among the markers that can be selected are auxotrophic markers including, but not limited to, URA3, HIS3, TRP1, LEU2, LYS2, ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotic. Examples of such markers include but are not limited to chloramphenicol acetyl transferase (CAT) gene, which confers resistance to chloramphenicol; CAN1 gene, which encodes an arginine permease and thereby renders cells sensitive to canavanine (see Sikorski et al., *Meth. Enzymol.*, 194:302–318 (1991)); the bacterial kanamycin resistance gene ($kan^R$), which renders eucaryotic cells resistant to the aminoglycoside G418 (see Wach et al., *Yeast*, 10:1793–1808 (1994)); and CYH2 gene, which confers sensitivity to cycloheximide (see Sikorski et al., *Meth. Enzymol.*, 194:302–318 (1991)). In addition, the CUPI gene, which encodes metallothionein and thereby confers resistance to copper, is also a suitable selection marker. Each of the above selection markers may be used alone or in combination. One or more selection markers can be included in a particular bait or prey vector. The bait vector and prey vector may have the same or different selection markers. In addition, the selection pressure can be placed on the transformed host cells either before or after mating the haploid yeast cells.

As will be apparent, the selection markers used should complement the host strains in which the bait and/or prey vectors are expressed. In other words, when a gene is used as a selection marker gene, a yeast strain lacking the selection marker gene (or having mutation in the corresponding gene) should be used as host cells. Numerous yeast strains or derivative strains corresponding to various selection markers are known in the art. Many of them have been developed specifically for certain yeast two-hybrid systems. The application and optional modification of such strains with respect to the present invention should be apparent to a skilled artisan apprised of the present disclosure. Methods for genetically manipulating yeast strains using genetic crossing or recombinant mutagenesis are well known in the art. See e.g., Rothstein, *Meth. Enzymol.*, 101:202–211 (1983). By way of example, the following yeast strains are well known in the art, and can be used in the present invention upon necessary modifications and adjustment:

L40 strain which has the genotype MATa his3Δ200 trp1-901 leu2-3,112 ade2 LYS2::(lexAop)4-HIS3 URA3::(lexAop)8-lacZ;

EGY48 strain which has the genotype MATα trp1 his3 ura3 6ops-LEU2; and

MaV103 strain which has the genotype MATα ura3-52 leu2-3,112 trp1-901 his3Δ200 ade2-101 gal4Δ gal80Δ SPAL10:: URA3 GAL1::HIS3:::lys2 (see Kumar et al., *J. Biol. Chem.* 272:13548–13554 (1997); Vidal et al., *Proc. Natl. Acad. Sci. USA*, 93:10315–10320 (1996)). Such strains are generally available in the research community, and can also be obtained by simple yeast genetic manipulation. See, e.g., *The Yeast TwoHybrid System*, Bartel and Fields, eds., pages 173–182, Oxford University Press, New York, N.Y., 1997.

In addition, the following yeast strains are commercially available:

Y190 strain which is available from Clontech, Palo Alto, Calif. and has the genotype MATα gal4 gal80 his3Δ200 trp1-901 ade2-101 ura3-52 leu2-3, 112 URA3::GAL1-lacZLYS2:::GAL1-HIS3 cyhr; and YRG-2 Strain which is available from Stratagene, La Jolla, Calif. and has the genotype MATa ura3-52 his3-200 ade2-101 lys2–801 trp1-901 leu2-3,112 gal4-542 gal80-538 LYS2:::GAL1-HIS3 URA3::GAL1/CYC1-lacZ.

In fact, different versions of vectors and host strains specially designed for yeast two-hybrid system analysis are available in kits from commercial vendors such as Clontech, Palo Alto, Calif. and Stratagene, La Jolla, Calif., all of which can be modified for use in the present invention.

4.3.1.2. Reporters

Generally, in a transcription-based two-hybrid assay, the interaction between a bait fusion protein and a prey fusion protein brings the DNA-binding domain and the transcription-activation domain into proximity forming a functional transcriptional factor, which acts on a specific promoter to drive the expression of a reporter protein. The transcription activation domain and the DNA-binding domain may be selected from various known transcriptional activators, e.g., GAL4, GCN4, ARD1, the human estrogen receptor, *E. coli*

LexA protein, herpes simplex virus VP16 (Triezenberg et al., *Genes Dev.* 2:718–729 (1988)), the *E. coli* B42 protein (acid blob, see Gyuris et al., *Cell,* 75:791–803 (1993)), NF-KB p65, and the like. The reporter gene and the promoter driving its transcription typically are incorporated into a separate reporter vector. Alternatively, the host cells are engineered to contain such a promoter-reporter gene sequence in their chromosomes. Thus, the interaction or lack of interaction between two interacting protein members of a protein complex can be determined by detecting or measuring changes in the reporter in the assay system. Although the reporters and selection markers can be of similar types and used in a similar manner in the present invention, the reporters and selection markers should be carefully selected in a particular detection assay such that they are distinguishable from each other and do not interfere with each other's function.

Many different types reporters are useful in the screening assays. For example, a reporter protein may be a fusion protein having an epitope tag fused to a protein. Commonly used and commercially available epitope tags include sequences derived from, e.g., influenza virus hemagglutinin (HA), Simian Virus 5 (V5), polyhistidine (6× His), c-myc, lacZ, GST, and the like. Antibodies specific to these epitope tags are generally commercially available. Thus, the expressed reporter can be detected using an epitope-specific antibody in an immunoassay.

In another embodiment, the reporter is selected such that it can be detected by a color-based assay. Examples of such reporters include, e.g., the lacZ protein (β-galactosidase), the green fluorescent protein (GFP), which can be detected by fluorescence assay and sorted by flow-activated cell sorting (FACS) (See Cubitt et al., *Trends Biochem. Sci.,* 20:448–455 (1995)), secreted alkaline phosphatase, horseradish peroxidase, the blue fluorescent protein (BFP), and luciferase photoproteins such as aequorin, obelin, mnemiopsin, and berovin (See U.S. Pat. No. 6,087,476, which is incorporated herein by reference).

Alternatively, an auxotrophic factor is used as a reporter in a host strain deficient in the auxotrophic factor. Thus, suitable auxotrophic reporter genes include, but are not limited to, URA3, HIS3, TRP1, LEU2, LYS2, ADE2, and the like. For example, yeast cells containing a mutant URA3 gene can be used as host cells (Ura$^-$ phenotype). Such cells lack URA3-encoded functional orotidine-5'-phosphate decarboxylase, an enzyme required by yeast cells for the biosynthesis of uracil. As a result, the cells are unable to grow on a medium lacking uracil. However, wild-type orotidine-5'-phsphate decarboxylase catalyzes the conversion of a non-toxic compound 5-fluoroorotic acid (5-FOA) to a toxic product, 5-fluorouracil. Thus, yeast cells containing a wild-type URA3 gene are sensitive to 5-FOA and cannot grow on a medium containing 5-FOA. Therefore, when the interaction between the interacting protein members in the fusion proteins results in the expression of active orotidine-5'-phosphate decarboxylase, the Ura$^-$ (Foa$^R$) yeast cells will be able to grow on a uracil deficient medium (SC-Ura plates). However, such cells will not survive on a medium containing 5-FOA. Thus, protein-protein interactions can be detected based on cell growth.

Additionally, antibiotic resistance reporters can also be employed in a similar manner. In this respect, host cells sensitive to a particular antibiotics is used. Antibiotics resistance reporters include, for example, chloramphenicol acetyl transferase (CAT) gene and the kan$^R$ gene, which confers resistance to G418 in eukaryotes and to kanamycin in prokaryotes. In one embodiment, the present invention encompasses a method for selecting modulators of an interaction between a first polypeptide and a second polypeptide, wherein the first polypeptide is (1) Tsg101 protein, (2) a Tsg101 protein homologue having an amino acid sequence at least 90% identical to that of Tsg101 and capable of interacting with HIV GAGp6, or (iii) a Tsg101 protein fragment containing the Tsg101 UEV domain; and the second protein is (1) HIV GAG polypeptide, (2) a HIV GAG polypeptide homologue having an amino acid sequence at least 90% identical to that of HIV Gag polypeptide and capable of interacting with Tsg101, (3) HIV GAGp6 protein, (4) a HIV GAGp6 homologue having an amino acid sequence at least 90% identical to that of HIV GAGp6 polypeptide and capable of interacting with Tsg101, and (5) a HIV GAGp6 fragment capable of interacting with Tsg101; wherein a host cell is provided having a first fusion protein having said first polypeptide, and a second fusion protein having said second polypeptide, wherein a DNA binding domain is fused to one of said first and second polypeptides while a transcription-activating domain is fused to the other of said first and second polypeptides; and providing in said host cell a reporter gene, wherein the transcription of the reporter gene is determined by the interaction between the first polypeptide and the second polypeptide.

4.3.1.3. Screening Assays for Interaction Antagonists

The screening assay of the present invention is useful in selecting compounds capable of interfering with or disrupting or dissociating protein-protein interaction between Tsg101 or a homologue or derivative thereof and HIV GAGp6 or a homologue or derivative thereof. For example, Tsg101 and its interacting partners are believed to play a role in lentivirus propagation, particularly HIV propagation, and thus are involved in lentivirus infection and diseases caused by lentivirus infection, particularly HIV infection and AIDS. It may be possible to ameliorate or alleviate the diseases or disorders in a patient by interfering with or dissociating normal interactions between Tsg101 and HIV GAGp6. Alternatively, if the disease or disorder is associated with increased expression of Tsg101 and/or HIV GAGp6 in accordance with the present invention, then the disease may be treated or prevented by weakening or dissociating the interaction between Tsg101 and HIV GAGp6 in a patient. In addition, if a disease or disorder is associated with mutant forms of Tsg101 and/or HIV GAGp6 that lead to strengthened protein-protein interaction therebetween, then the disease or disorder may be treated with a compound that weakens or interferes with the interaction between the mutant forms of Tsg101 and HIGAGp6.

In a screening assay for a dissociator, Tsg101, a mutant form or a binding domain thereof, and HIV GAGp6, or a mutant form or a binding domain thereof, are used as test proteins expressed in the form of fusion proteins as described above for purposes of a two-hybrid assay. The fusion proteins are expressed in a host cell and allowed to interact with each other in the presence of one or more test compounds.

In a preferred embodiment, a counterselectable marker is used as a reporter such that a detectable signal (e.g., appearance of color or fluorescence, or cell survival) is present only when the test compound is capable of interfering with the interaction between the two test proteins. In this respect, the reporters used in various "reverse two-hybrid systems" known in the art may be employed. Reverse two-hybrid systems are disclosed in, e.g., U.S. Pat. Nos. 5,525,490; 5,733,726; 5,885,779; Vidal et al., *Proc. Natl. Acad. Sci.*

USA, 93:10315–10320 (1996); and Vidal et al., *Proc. Natl. Acad. Sci. USA,* 93:10321–10326 (1996), all of which are incorporated herein by reference.

Examples of suitable counterselectable reporters useful in a yeast system include the URA3 gene (encoding orotidine-5'-decarboxylase, which converts 5-fluroorotic acid (5-FOA) to the toxic metabolite 5-fluorouracil), the CAN1 gene (encoding arginine permease, which transports toxic arginine analog canavanine into yeast cells), the GAL1 gene (encoding galactokinase, which catalyzes the conversion of 2-deoxygalactose to toxic 2-deoxygalactose-1-phosphate), the LYS2 gene (encoding α-aminoadipate reductase, which renders yeast cells unable to grow on a medium containing α-aminoadipate as the sole nitrogen source), the MET15 gene (encoding O-acetylhomoserine sulfhydrylase, which confers on yeast cells sensitivity to methyl mercury), and the CYH2 gene (encoding L29 ribosomal protein, which confers sensitivity to cycloheximide). In addition, any known cytotoxic agents including cytotoxic proteins such as the diphtheria toxin (DTA) catalytic domain can also be used as counterselectable reporters. See U.S. Pat. No. 5,733,726. DTA causes the ADP-ribosylation of elongation factor-2 and thus inhibits protein synthesis and causes cell death. Other examples of cytotoxic agents include recin, Shiga toxin, and exotoxin A of *Pseudomonas aeruginosa.*

For example, when the URA3 gene is used as a counterselectable reporter gene, yeast cells containing a mutant URA3 gene can be used as host cells (Ura$^-$Foa$^R$ phenotype) for the in vivo assay. Such cells lack URA3-encoded functional orotidine-5'-phsphate decarboxylase, an enzyme required for the biosynthesis of uracil. As a result, the cells are unable to grow on media lacking uracil. However, because of the absence of a wild-type orotidine-5'-phsphate decarboxylase, the yeast cells cannot convert non-toxic 5-fluoroorotic acid (5-FOA) to a toxic product, 5-fluorouracil. Thus, such yeast cells are resistant to 5-FOA and can grow on a medium containing 5-FOA. Therefore, for example, to screen for a compound capable of disrupting interaction between Tsg101 and HIV GAGp6, Tsg101 can be expressed as a fusion protein with a DNA-binding domain of a suitable transcription activator while HIV GAGp6 is expressed as a fusion protein with a transcription activation domain of a suitable transcription activator. In the host strain, the reporter URA3 gene may be operably linked to a promoter specifically responsive to the association of the transcription activation domain and the DNA-binding domain. After the fusion proteins are expressed in the Ura$^-$Foa$^R$ yeast cells, an in vivo screening assay can be conducted in the presence of a test compound with the yeast cells being cultured on a medium containing uracil and 5-FOA. If the test compound does not disrupt the interaction between Tsg101 and HIV GAGp6, active URA3 gene product, i.e., orotidine-5'-decarboxylase, which converts 5-FOA to toxic 5-fluorouracil, is expressed. As a result, the yeast cells cannot grow. On the other hand, when the test compound disrupts the interaction between Tsg101 and HIV GAGp6, no active orotidine-5'-decarboxylase is produced in the host yeast cells. Consequently, the yeast cells will survive and grow on the 5-FOA-containing medium. Therefore, compounds capable of interfering with or dissociating the interaction between Tsg101 and HIV GAGp6 can thus be identified based on colony formation.

As will be apparent, the screening assay of the present invention can be applied in a format appropriate for large-scale screening. For example, combinatorial technologies can be employed to construct combinatorial libraries of small organic molecules or small peptides. See generally, e.g., Kenan et al., *Trends Biochem. Sc.,* 19:57–64 (1994); Gallop et al., *J. Med. Chem.,* 37:1233–1251 (1994); Gordon et al., *J. Med. Chem.,* 37:1385–1401 (1994); Ecker et al., *Biotechnology,* 13:351–360 (1995). Such combinatorial libraries of compounds can be applied to the screening assay of the present invention to isolate specific modulators of particular protein-protein interactions. In the case of random peptide libraries, the random peptides can be co-expressed with the fusion proteins of the present invention in host cells and assayed in vivo. See e.g., Yang et al., *Nucl. Acids Res.,* 23:1152–1156 (1995). Alternatively, they can be added to the culture medium for uptake by the host cells.

Conveniently, yeast mating is used in an in vivo screening assay. For example, haploid cells of a-mating type expressing one fusion protein as described above is mated with haploid cells of α-mating type expressing the other fusion protein. Upon mating, the diploid cells are spread on a suitable medium to form a lawn. Drops of test compounds can be deposited onto different areas of the lawn. After culturing the lawn for an appropriate period of time, drops containing a compound capable of modulating the interaction between the particular test proteins in the fusion proteins can be identified by stimulation or inhibition of growth in the vicinity of the drops.

The screening assays of the present invention for selecting compounds capable of modulating protein-protein interactions can also be fine-tuned by various techniques to adjust the thresholds or sensitivity of the positive and negative selections. Mutations can be introduced into the reporter proteins to adjust their activities. The uptake of test compounds by the host cells can also be adjusted. For example, yeast high uptake mutants such as the erg6 mutant strains can facilitate yeast uptake of the test compounds. See Gaber et al., *Mol. Cell. Biol.,* 9:3447–3456 (1989). Likewise, the uptake of the selection compounds such as 5-FOA, 2-deoxygalactose, cycloheximide, α-aminoadipate, and the like can also be fine-tuned.

4.4. Virtual Screen and Compound Optimization

Compounds can also be selected based on structural models of the target protein or protein complex and/or test compounds, e.g., by virtual screen. In addition, once an effective compound is identified, structural analogs or mimetics thereof can be produced based on rational drug design with the aim of improving drug efficacy and stability, and reducing side effects. Methods known in the art for virtual screen and rational drug design can be used in the present invention. See, e.g., Hodgson et al., *Bio/Technology,* 9:19–21 (1991); U.S. Pat. Nos. 5,800,998 and 5,891,628, all of which are incorporated herein by reference. An example of rational drug design is the development of HIV protease inhibitors. See Erickson et al., *Science,* 249:527–533 (1990).

In this respect, structural information on the target protein or protein complex is obtained. Preferably, atomic coordinates defining a three-dimensional structure of the target protein or protein complex are obtained. For example, each of the interacting pair can be expressed and purified. The purified interacting protein pairs are then allowed to interact with each other in vitro under appropriate conditions. Optionally, the interacting protein complex can be stabilized by crosslinking or other techniques. The interacting complex can be studied using various biophysical techniques including, e.g., X-ray crystallography, NMR, computer modeling, mass spectrometry, and the like. Methods for obtaining such atomic coordinates by X-ray crystallography, NMR, and the like are known in the art and the application thereof to the target protein or protein complex of the present invention should be apparent to skilled persons in the art of structural biology. See Smyth and Martin, *Mol. Pathol.*, 53:8–14 (2000); Oakley and Wilce, *Clin. Exp. Pharmacol. Physiol.*, 27(3):145–151 (2000); Ferentz and Wagner, *Q. Rev. Biophys.*, 33:29–65 (2000); and Roberts, *Curr. Opin. Biotechnol.*, 10:42–47 (1999).

In addition, understanding of the interaction between the proteins of interest in the presence or absence of a modulator compound can also be derived from mutagenesis analysis using yeast two-hybrid system or other methods for detection protein-protein interaction. In this respect, various mutations can be introduced into the interacting proteins and the effect of the mutations on protein-protein interaction is examined by a suitable method such as the yeast two-hybrid system.

Various mutations including amino acid substitutions, deletions and insertions can be introduced into a protein sequence using conventional recombinant DNA technologies. Generally, it is particularly desirable to decipher the binding sites. Thus, it is important that the mutations introduced only affect protein-protein interaction or protein-compound interaction and cause minimal structural disturbances. Mutations are preferably designed based on knowledge of the three-dimensional structure of the interacting proteins. Preferably, mutations are introduced to alter charged amino acids or hydrophobic amino acids exposed on the surface of the proteins, since ionic interactions and hydrophobic interactions are often involved in protein-protein interactions. Alternatively, the "alanine scanning mutagenesis" technique is used. See Wells, et al., *Methods Enzymol.*, 202:301–306 (1991); Bass et al., *Proc. Natl. Acad. Sci. USA*, 88:4498–4502 (1991); Bennet et al., *J. Biol. Chem.*, 266:5191–5201 (1991); Diamond et al., *J. Virol.*, 68:863–876 (1994). Using this technique, charged or hydrophobic amino acid residues of the interacting proteins are replaced by alanine, and the effect on the interaction between the proteins is analyzed using e.g., the yeast two-hybrid system. For example, the entire protein sequence can be scanned in a window of five amino acids. When two or more charged or hydrophobic amino acids appear in a window, the charged or hydrophobic amino acids are changed to alanine using standard recombinant DNA techniques. The thus mutated proteins are used as "test proteins" in the above-described two-hybrid assay to examine the effect of the mutations on protein-protein interaction. Preferably, the mutagenesis analysis is conducted both in the presence and in the absence of an identified modulator compound. In this manner, the domains or residues of the proteins important to protein-protein interaction and/or the interaction between the modulator compound and the proteins can be identified. Likewise, interactions between a selected compound and a target protein (e.g., Tsg101) can also be studied by mutagenesis of the target protein.

Based on the structural information obtained, structural relationships between the interacting proteins, between a selected compound and the interacting proteins, or between a selected compound and a target protein are elucidated. The moieties and the three-dimensional structure of the selected compound critical to its modulating effect on the interaction of the proteins of interest or on a target protein are revealed. Medicinal chemists can then design analog compounds having similar moieties and structures.

In addition, an identified peptide compound capable of modulating a particular protein-protein interaction or a particular target protein can also be analyzed by the alanine scanning technique and/or a screening assay to determine the domains or residues of the peptide important to its modulating effect on a particular protein-protein interaction or a particular target protein. The peptide compound can be used as a lead molecule for rational design of small organic molecules or peptide mimetics. See Huber et al., *Curr. Med. Chem.*, 1:13–34 (1994).

The residues or domains critical to the modulating effect of the identified compound constitute the active region of the compound known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis, similarity mapping and the like can all be used in this modeling process. See e.g., Perry et al., in *OSAR: Quantitative Structure-Activity Relationships in Drug Design*, pp.189–193, Alan R. Liss, Inc., 1989; Rotivinen et al., *Acta Pharmaceutical Fennica*, 97:159–166 (1988); Lewis et al., *Proc. R. Soc. Lond.*, 236:125–140 (1989); McKinaly et al., *Annu. Rev. Pharmacol. Toxiciol.*, 29:111–122 (1989). Commercial molecular modeling systems available from Polygen Corporation, Waltham, Mass., include the CHARMm program, which performs the energy minimization and molecular dynamics functions, and QUANTA program which performs the construction, graphic modeling and analysis of molecular structure. Such programs allow interactive construction, visualization and modification of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved efficacy and reduced side effect can be developed. The compounds identified in accordance with the present invention can be incorporated into a pharmaceutical formulation suitable for administration to an individual.

In addition, the structural models or atomic coordinates defining a three-dimensional structure of the target protein or protein complex can also be used in virtual screen to select compounds capable of modulating the target protein or protein complex. Various methods of computer-based virtual screen using atomic coordinates are generally known in the art. For example, U.S. Pat. No. 5,798,247 (which is incorporated herein by reference) discloses a method of identifying a compound (specifically, an interleukin converting enzyme inhibitor) by determining binding interactions between an organic compound and binding sites of a binding cavity within the target protein. The binding sites are defined by atomic coordinates.

EXAMPLES

1. Yeast Two-Hybrid System

The principles and methods of the yeast two-hybrid system have been described in detail in *The Yeast Two-Hybrid System*, Bartel and Fields, eds., pages 183–196, Oxford University Press, New York, N.Y., 1997. The following is thus a description of the particular procedure that we used.

The cDNA encoding the bait protein HIV GAGp6 was derived from HIV-1 NY5/BRU isolate. The cDNA product was then introduced by recombination into the yeast expression vector pGBT.Q, which is a close derivative of pGBT.C (See Bartel et al., Nat Genet., 12:72–77 (1996)) in which the polylinker site has been modified to include M13 sequencing sites. The new construct was selected directly in the yeast strain PNY200 for its ability to drive tryptophane synthesis (genotype of this strain: MATα trp1-901 leu2-3,112 ura3-52 his3-200 ade2 gal4Δ gal80). In these yeast c was produced as a C-terminal fusion protein with the DNA binding domain of the transcription factor Gal4 (amino acids 1 to 147).

Prey libraries (e.g., a human spleen cDNA library) were transformed into the yeast strain BK100 (genotype of this strain: MATα trp1-901 leu2-3,112 ura3-52 his3-200 gal4Δ gal80LYS2::GAL-HIS3 GAL2-ADE2 met2::GAL7-lacZ), and selected for the ability to drive leucine synthesis. In these yeast cells, each cDNA was expressed as a fusion protein with the transcription activation domain of the transcription factor Gal4 (amino acids 768 to 881) and a 9 amino acid hemagglutinin epitope tag. PNY200 cells (MATα mating type), expressing the bait, were then mated with BK100 cells (MATa mating type), expressing prey proteins from the prey library. The resulting diploid yeast cells expressing proteins interacting with the bait protein were selected for the ability to synthesize tryptophan, leucine, histidine, and adenine. DNA was prepared from each clone, transformed by electroporation into E. coli strain KC8 (Clontech KC8 electrocompetent cells, Catalog No. C2023-1), and the cells were selected on ampicillin-containing plates in the absence of either tryptophane (selection for the bait plasmid) or leucine (selection for the library plasmid). DNA for both plasmids was prepared and sequenced by the dideoxynucleotide chain termination method. The identity of the bait cDNA insert was confirmed and the cDNA insert from the prey library plasmid was identified using the BLAST program to search against public nucleotide and protein databases. Plasmids from the prey library were then individually transformed into yeast cells together with a plasmid driving the synthesis of lamin and 5 other test proteins, respectively, fused to the Gal4 DNA binding domain. Clones that gave a positive signal in the β-galactosidase assay were considered false-positives and discarded. Plasmids for the remaining clones were transformed into yeast cells together with the original bait plasmid. Clones that gave a positive signal in the β-galactosidase assay were considered true positives.

HIV GAGp6 sequence indicated in Table 1 was used in the yeast two-hybrid system described above. The isolated Tsg101 prey sequences are summarized in Table 1. The GenBank Accession Nos. for the bait and prey proteins are also provided in Table 1, upon which the bait and prey sequences are aligned.

2. Production of Antibodies Selectively Immunoreactive with Protein Complex

HIV GAGp6 and the UEV domain of Tsg101 are recombinantly expressed in human host cells and isolated and purified. A protein complex is formed by mixing the two purified interacting proteins (fragments). A protein complex is also formed by mixing recombinantly expressed intact complete Tsg101 and HIV GAGp6. The two protein complexes are used as antigens in immunizing a mouse. mRNA is isolated from the immunized mouse spleen cells, and first-strand cDNA is synthesized based on the mRNA. The $V_H$ and $V_K$ genes are amplified from the thus synthesized cDNAs by PCR using appropriate primers.

The amplified $V_H$ and $V_K$ genes are ligated together and subcloned into a phagemid vector for the construction of a phage display library. E. coli. cells are transformed with the ligation mixtures, and thus a phage display library is established. Alternatively, the ligated $V_H$ and $V_k$ genes are subcloned into a vector suitable for ribosome display in which the $V_H$-$V_k$ sequence is under the control of a T7 promoter. See Schaffitzel et al., J. Immun. Meth., 231:119–135 (1999).

The libraries are screened with the Tsg101-HIV GAGp6 complex and individual Tsg101 and HIV GAGp6. Several rounds of screening are preferably performed. Clones corresponding to scFv fragments that bind the Tsg101-HIV GAGp6 complex, but not the individual Tsg101 and HIV GAGp6 are selected and purified. A single purified clone is used to prepare an antibody selectively immunoreactive with the Tsg101-HIV GAGp6 complex. The antibody is then verified by an immunochemistry method such as RIA and ELISA.

In addition, the clones corresponding to scFv fragments that bind the Tsg101-HIV GAGp6 complex and also binds Tsg101 and/or HIV GAGp6 may be selected. The scFv genes in the clones are diversified by mutagenesis methods such as oligonucleotide-directed mutagenesis, error-prone PCR (See Lin-Goerke et al., Biotechniques, 23:409 (1997)), dNTP analogues (See Zaccolo et al., J. Mol. Biol., 255:589 (1996)), and other methods. The diversified clones are further screened in phage display or ribosome display libraries. In this manner, scFv fragments selectively immunoreactive with the Tsg101-HIV GAGp6 complex may be obtained.

3. Correlations Between Tsg101-HIV GAGp6 Interaction and HIV Budding

Yeast two-hybrid assays were utilized to determine the effect of amino acid substitution mutations in the PTAP motif of HIV GAGp6 on the interaction between Tsg101 and GAGp6. To prepare a yeast two-hybrid activation domain-Tsg101 construct, a DNA fragment encompassing the full-length coding sequence for Tsg101 according to GenBank Accession No. U82130 was obtained by PCR from a human fetal brain cDNA library and cloned into the EcoRI/PstI sites of the activation domain parent plasmid GADpN2 (LEU2, CEN4, ARS1, ADH1p-SV40NLS-GAL4 (768–881)-MCS (multiple cloning site)-PGK1t, AmpR, ColE1_ori).

To prepare the yeast two-hybrid DNA binding domain-HIV1 GAGp6 construct, a DNA fragment corresponding to the HIV1 GAGp6 peptide derived from the HIV1.NL43 strain GAG protein was obtained by PCR from the NL43 containing plasmid R9≠apa and was cloned into the EcoRI/SalI sites of the binding domain parent plasmid pGBT.Q.

The following amino acid substitution mutations were introduced by PCR into the HIV1 GAGp6 sequence in the yeast two-hybrid binding domain-HIV1 GAGp6 construct described above. The mutations were verified by DNA sequence analysis. Such mutations are summarized in Table 3 below.

TABLE 3

Tested Mutations in GAGp6 Protein

| Mutant Construct | GAGp6 Peptide Sequence Surrounding the PTAP Motif | | | | | | | | | | | | | | |
|---|---|---|---|---|---|---|---|---|---|---|---|---|---|---|---|
| P6/wt | S | R | P | E | P | T | A | P | P | E | E | S | F | R | F |
| P6/E6G |   |   |   | G |   |   |   |   |   |   |   |   |   |   |   |
| P6/P7L |   |   |   |   | L |   |   |   |   |   |   |   |   |   |   |
| P6/A9R |   |   |   |   |   |   | R |   |   |   |   |   |   |   |   |
| P6/P10L |   |   |   |   |   |   |   | L |   |   |   |   |   |   |   |

To test the effect of the mutations, yeast cells of the strain Y189 purchased from Clontech (ura3-52 his3*200 ade2-101 trp1-901 leu2-3,112 met gal4 gal80 URA3::GAL1p-lacZ) were co-transformed with the activation domain-Tsg101 construct and one of the binding domain-mutant GAGp6 constructs or the binding domain-wild type GAGp6 construct. Filter lift assays for β-Gal activity were conducted by lifting the transformed yeast colonies with filters, lysing the yeast cells by freezing and thawing, and contacting the lysed cells with X-Gal. Positive β-Gal activity indicates that the GAGp6 wild type or mutant protein interacts with Tsg101. All binding domain constructs were also tested for self-activation of β-Gal activity. The results are shown in Table 4.

TABLE 4

Interactions Between Tsg101 and GAGp6

|         | P6/wt | P6/E6G | P6/P7L | P6/A9R | P6/P10L |
|---------|-------|--------|--------|--------|---------|
| Tsg101  | +     | +      | −      | −      | −       |
| P6/wt   | −     |        |        |        |         |
| P6/E6G  |       | −      |        |        |         |
| P6/P7L  |       |        | −      |        |         |
| P6/A9R  |       |        |        | −      |         |
| P6/P10L |       |        |        |        | −       |

Thus, as is clear from Table 3, the mutations in the PTAP motif of HIV GAGp6 abolished the interaction between Tsg101 and HIV GAGp6, while the p6/E6G mutation outside the PTAP motif did not result in the elimination of the Tsg101-GAGp6 interaction.

The interactions between Tsg101 and wild-type GAGp6 (WT) or the GAGp6 PTAP mutants were further quantitated by performing liquid culture β-galactosidase assays. Cultures were grown overnight in synthetic media (−Leu, −Trp, +glucose) in 96 well plates, normalized for optical density, and lysed by addition of 6× lysis/substrate solution in 6× Z-buffer (60 mM KCl, 6 mM $MgSO_4$, 360 mM $Na_2HPO_4$, 240 mM $NaH_2PO_4$, 6 mg/ml CPRG, 0.12U/ml lyticase, 0.075% NP-40). Cultures were incubated for 2 hr at 37° C., clarified by centrifugation, and the optical absorbance of each supernatant was measured (575 nm). Full length Tsg101 bound wild-type p6 in the two-hybrid liquid culture assay, resulting in high levels of β-galactosidase activity (>300-fold over background). Three different p6 point mutants were used to test whether the Tsg101 binding interaction required the PTAP late domain motif within HIV-1 p6, and all three (P6L, A9R and P10L) reduced β-galactosidase activity to background levels. Each of these point mutations also arrests HIV-1 budding at a late stage (Huang et al. 1995). These results are consistent with the hypothesis that the interaction between HIV GAGp6 and the human cellular protein Tsg101 is essential for viral budding to occur.

4. In Vitro Binding Assays

A fusion protein with a GST tag fused to the HIV-1 GAGp6 domain was recombinantly expressed and purified by chromatography. In addition, a GAGp6 peptide containing the first 14 amino acid residues ("p6(1–14)") was synthesized chemically by standard peptide synthesis methods. The peptide was purified by conventional protein purification techniques, e.g., by chromatography.

Nunc/Nalgene Maxisorp plates were incubated overnight at 4° C. or for 1–2 hrs at room temperature in 100 μl of a protein coupling solution containing purified GST-p6 and 50 mM Carbonate, pH=9.6. This allowed the attachment of the GST-p6 fusion protein to the plates. Liquids in the plates were then emptied and wells filled with 400 μl/well of a blocking buffer (SuperBlock; Pierce-Endogen, Rockford, Ill.). After incubating for 1 hour at room temperature, 100 μl of a mixture containing Drosophila S2 cell lysate myc-tagged Tsg101 (residues 1–207) and a specific amount of the p6(1–14) peptide were applied to the wells of the plate. This mixture was allowed to react for 2 hours at room temperature to form p6:Tsg101 protein-protein complexes.

Plates were then washed 4×100 μl with 1× PBST solution (Invitrogen; Carlsbad, Calif.). After washing, 100 μl of 1 μg/ml solution of anti-myc monoclonal antibody (Clone 9E10; Roche Molecular Biochemicals; Indianapolis, Ind.) in 1× PBST was added to the wells of the plate to detect the myc-epitope tag on the Tsg101 protein. Plates were then washed again with 4×100 μl with 1× PBST solution and 100 μl of 1 μg/ml solution of horseradish peroxidase (HRP) conjugated Goat anti-mouse IgG (Jackson Immunoresearch Labs; West Grove, Pa.) in 1× PBST was added to the wells of the plate to detect bound mouse anti-myc antibodies. Plates were then washed again with 4×100 μl with 1× PBST solution and 100 μl of fluorescent substrate (QuantaBlu; Pierce-Endogen, Rockford, Ill.) was added to all wells. After 30 minutes, 100 μl of stop solution was added to each well to inhibit the function of HRP. Plates were then read on a Packard Fusion instrument at an excitation wavelength of 325 nm and an emission wavelength of 420 nm. The presence of fluorescent signals indicates binding of Tsg101 to the fixed GST-p6. In contrast, the absence of fluorescent signals indicates that the $PX_1X_2P$-containing short peptide is capable of disrupting the interaction between Tsg101 and HIV p6.

Figure 2:
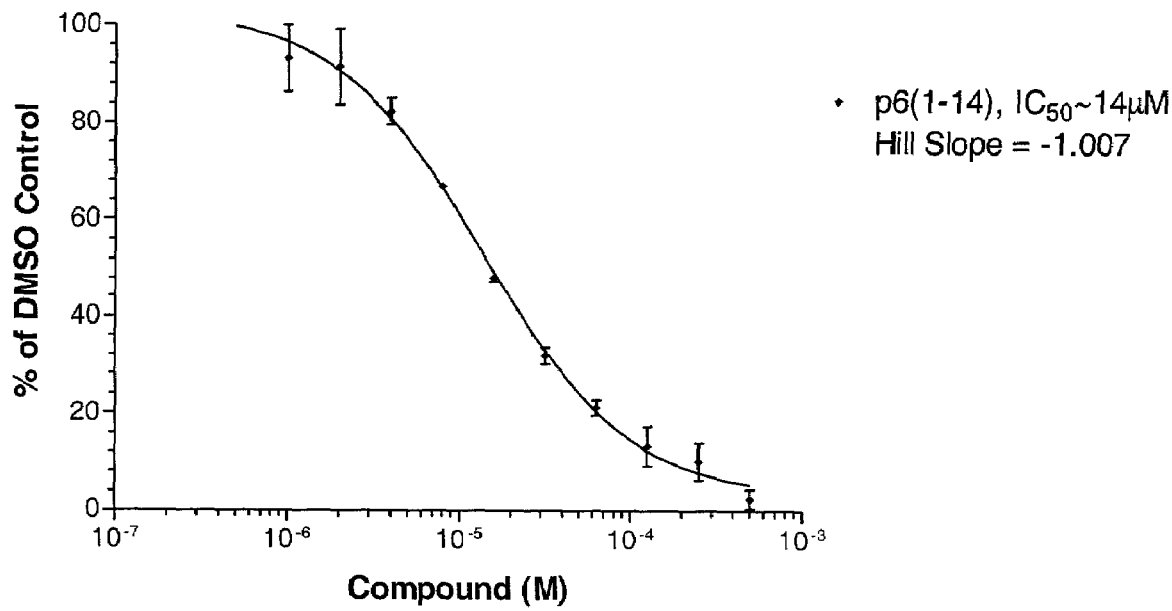
FIG. 2 is a competitive inhibition curve showing that the p(1-14) peptide having the first 14 amino acid residues is capable of inhibiting protein-protein interaction between GST-p6 and myc-Tsg101(1-207)
Figure 3:
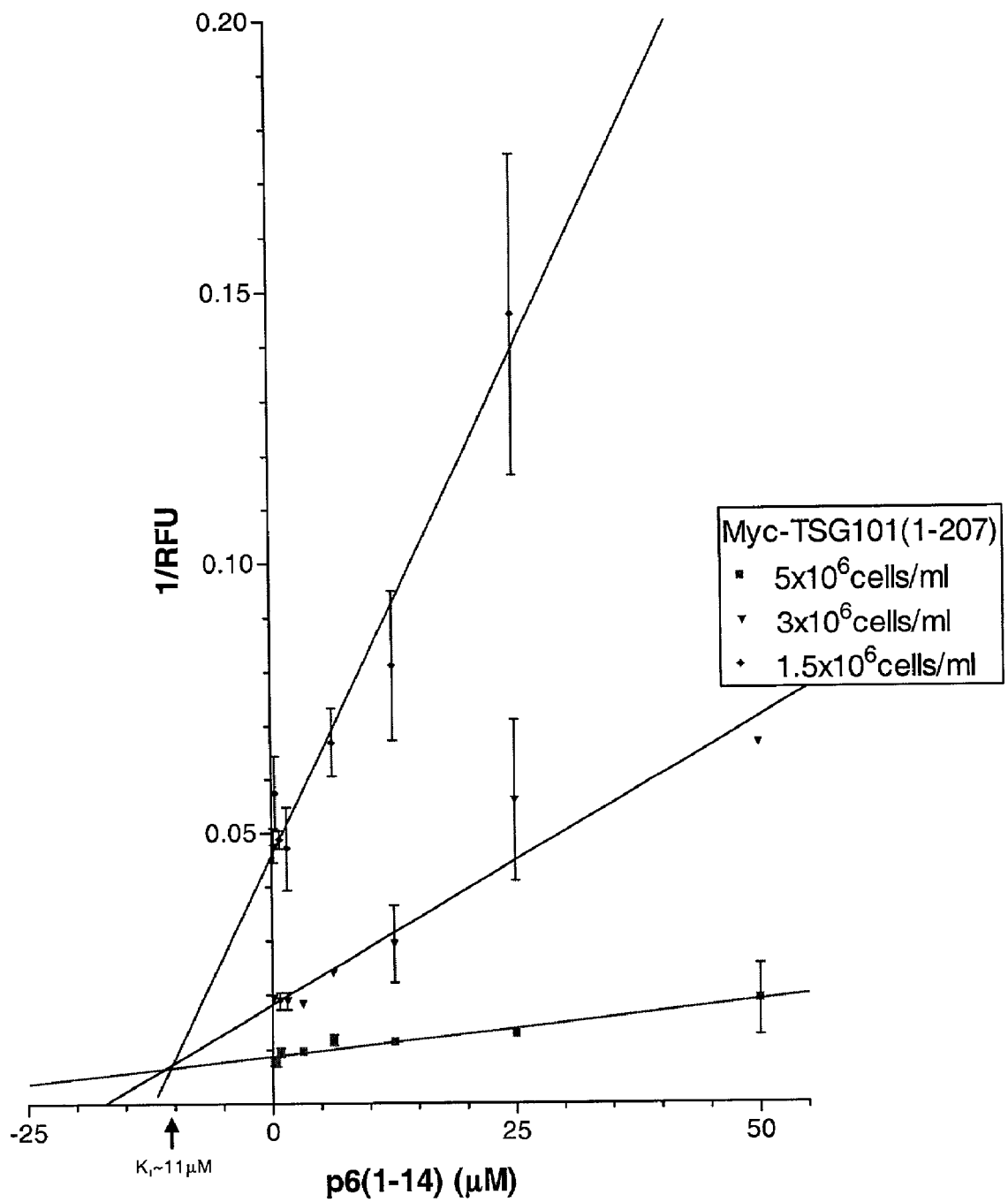
FIG. 3 is a Dixon plot showing p6(1-14) inhibition of the interaction between GST-p6 and myc-Tsg101(1-207)
Figure 4:
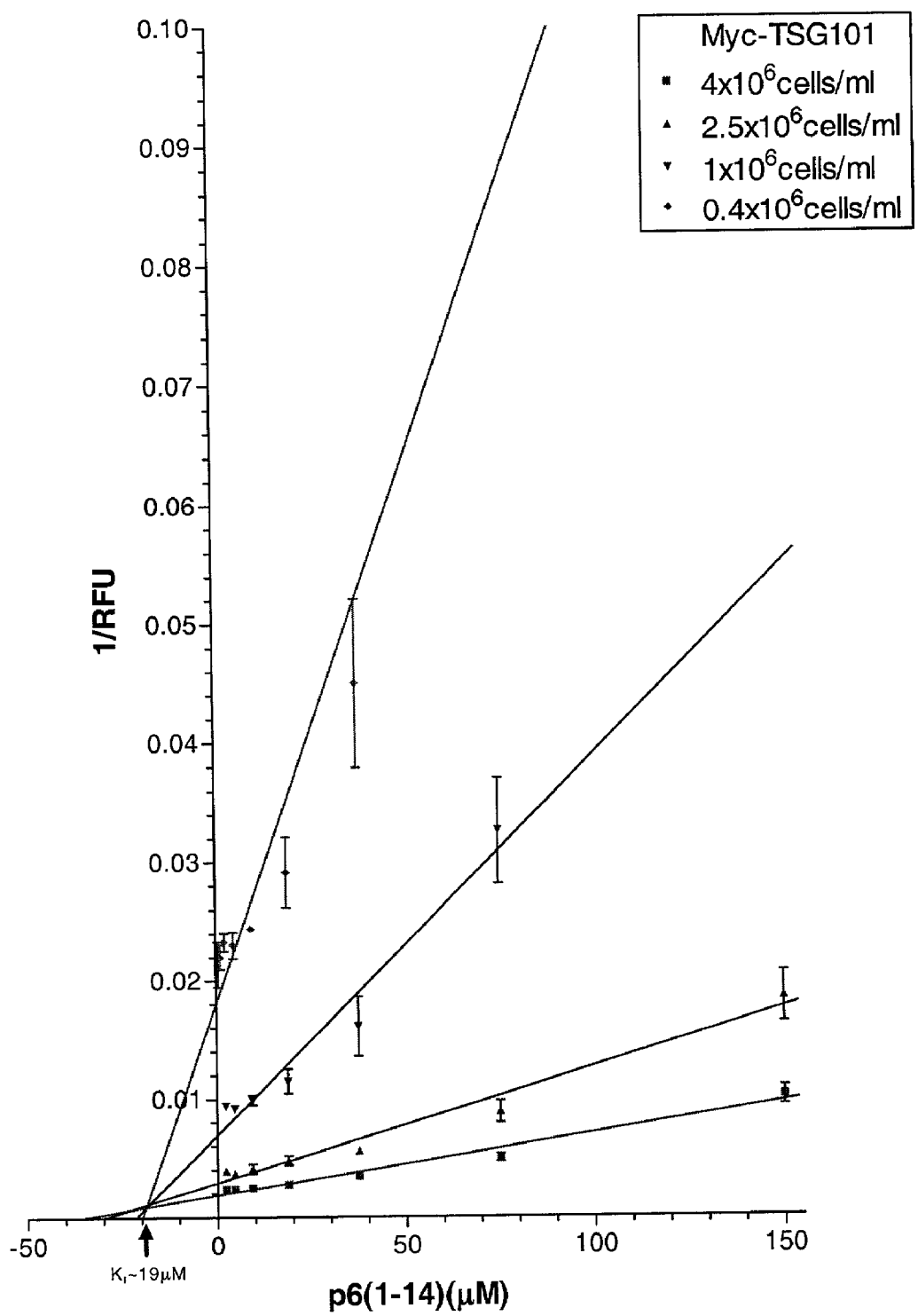
FIG. 4 is another Dixon plot showing p6(1-14) inhibition of the interaction between GST-p6 and myc-Tsg101(1-207).

Different concentrations of the p6(1–14) peptide were tested, and the relative intensities of the fluorescence signals obtained at different concentrations were plotted against the peptide concentrations. The competitive inhibition curve is shown in FIG. 2. Two Dixon plots are shown in FIG. 3 and FIG. 4, respectively.

5. Yeast Screen to Identify Small Molecule Inhibitors of the Interaction Between HIV GAGp6 And Tsg101

Beta-galactosidase is used as a reporter enzyme to signal the interaction between yeast two-hybrid protein pairs expressed from plasmids in *Saccharomyces cerevisiae*. Yeast strain MY209 (ade2 his3 leu2 trp1 cyh2 ura3::GAL1p-lacZ gal4 gal80 lys2::GAL1p-HIS3) bearing the plasmids Mp364 (LEU2 CEN4 ARS1 ADH1p-SV40NLS-GAL4 (768–881)-Tsg101 (1–390)-PGK1t AmpR ColE1_ori) and Mp206 (TRP1 CEN4 ARS ADH1p-GAL4(1–147)-HIV1_gag (448–500)-ADH1t AmpR ColE1_ori) is cultured synthetic complete media lacking leucine and tryptophan (SC-Leu-Trp) overnight at 30° C. This culture is diluted to 0.01 $OD_{630}$ units/ml using SC-Leu-Trp media. The diluted MY209 culture is dispensed into 96-well microplates. Compounds from a library of small molecules are added to the microplates; the final concentration of test compounds is approximately 60 µM. The assay plates are incubated at 30° C. overnight.

The following day an aliquot of concentrated substrate/lysis buffer is added to each well and the plates incubated at 37° C. for 1–2 hours. At an appropriate time an aliquot of stop solution is added to each well to halt the beta-galactosidase reaction. For all microplates an absorbance reading is obtained to assay the generation of product from the enzyme substrate. The presence of putative inhibitors of the interaction between HIV p6 and Tsg101 results in inhibition of the beta-galactosidase signal generated by MY209. Additional testing eliminates compounds that decreased expression of beta-galactosidase by affecting yeast cell growth and non-specific inhibitors that affected the beta-galactosidase signal generated by the interaction of an unrelated protein pair.

Once a hit, i.e., a compound which inhibits the interaction between the viral and cellular proteins, is obtained, the compound is identified and subjected to further testing wherein the compounds are assayed at several concentrations to determine an $IC_{50}$ value, this being the concentration of the compound at which the signal seen in the two-hybrid assay described in this Example is 50% of the signal seen in the absence of the inhibitor.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated protein complex having a first protein interacting with a second protein, said first protein being selected from the group consisting of:
   (a) Tsg101,
   (b) a Tsg101 fragment that comprises a UEV domain and interacts with an HIV GAGp6 late domain,
       (c) a first polypeptide that interacts with an HIV GAGp6 late domain and has an amino acid sequence that is at least about 75% identical to (a) or (b), and
   (d) a first fusion protein comprising (a), (b), or (c); and said second protein being selected from the group consisting of:
   (i) HIV GAG,
   (ii) a fragment of HIV GAG that comprises an HIV GAGp6 late domain and interacts with Tsg101,
       (iii) a second polypeptide that interacts with Tsg101 and has an amino acid sequence that is at least about 75% identical to that of (i) or (ii), and
       (iv) a second fusion protein comprising (i), (ii), or (iii).

2. The isolated protein complex of claim 1, wherein said second protein is HIV GAGp6 or a fragment thereof that comprises an HIV GAGp6 late domain and interacts with Tsg101.

3. The isolated protein complex of claim 1, wherein said first protein is said first fusion protein.

4. The isolated protein complex of claim 1, wherein said second protein is said second fusion protein.

5. An isolated protein complex having:
   a first protein which is a Tsg101 fragment that comprises a UEV domain and interacts with an HIV GAGp6 late domain, or a first polypeptide that interacts with an HIV GAGp6 late domain and has an amino acid sequence that is at least about 75% identical to the Tsg101 UEV domain, interacting with
   a second protein which is HIV GAGp6 or an HIV GAGp6 fragment that comprises an HIV GAGp6 late domain and interacts with Tsg101, or a second polypeptide that comprises an HIV GAGp6 late domain, interacts with Tsg101, and has an amino acid sequence that is at least about 75% identical to that of HIV GAGp6 or said HIV GAGp6 fragment.

6. The isolated protein complex of claim 5, wherein said first protein is a fusion protein comprising said Tsg101 fragment or said first polypeptide.

7. The isolated protein complex of claim 5, wherein said second protein is a fusion protein comprising (a) HIV GAGp6 or (b) said HIV GAGp6 fragment or (c) said second polypeptide.

8. An isolated protein complex comprising:
   (a) a first protein which is selected from the group consisting of
       (i) a Tsg101 fragment that comprises a UEV domain and interacts with an HIV GAGp6 late domain,
       (ii) a first polypeptide that interacts with an HIV GAGp6 late domain and has an amino acid sequence at least 90% identical to the Tsg101 UEV domain, and
       (iii) a fusion protein comprising (i) or (ii); and
   (b) a second protein selected from the group consisting of
       (1) HIV GAG,
       (2) an HIV GAG fragment that comprises an HIV GAGp6 late domain and interacts with Tsg101,
       (3) an HIV GAG homologue that has an amino acid sequence at least about 90% identical to that of (1) or (2) and interacts with Tsg101,
       (4) HIV GAGp6,
       (5) an HIV GAGp6 homologue that has an amino acid sequence at least about 90% identical to that of HIV GAGp6 and interacts with Tsg101,
       (6) an HIV GAGp6 fragment that comprises an HIV GAGp6 late domain and interacts with Tsg101, and
       (7) a fusion protein comprising (1), (2), (3), (4), (5), or (6);
   wherein said first and second proteins interact to form said isolated protein complex.

9. The isolated protein complex of claim 8, wherein said HIV GAGp6 fragment comprises an amino acid sequence of SEQ ID NO:25 or SEQ ID NO:26.

10. The isolated protein complex of claim 8, wherein said HIV GAGp6 fragment comprises an amino acid sequence of SEQ ID NO:31 or SEQ ID NO:32.

11. The isolated protein complex of claim 8, wherein said HIV GAGp6 fragment has a contiguous span of at least 10 amino acid residues of a naturally occurring HIV GAGp6, said contiguous span comprising a P(T/S)AP late domain motif.

12. An isolated protein complex comprising:
   a first protein which is a Tsg101 fragment comprising a UEV domain, or a first polypeptide that has an amino acid sequence at least 75% identical the Tsg101 UEV domain, wherein said Tsg101 fragment or said first polypeptide interact with an HIV GAGp6 late domain; and
   a second protein which is a retrovirus GAG, a retrovirus GAG fragment comprising a P(T/S)AP late domain motif, or a homologue of said retrovirus GAG or said retrovirus GAG fragment that comprises a P(T/S)AP late domain motif and has an amino acid sequence that is at least about 75% identical to that of said retrovirus GAG or said retrovirus GAG fragment, wherein said retrovirus GAG, said retrovirus GAG fragment, said homologue of said retrovirus GAG, or said homologue of said retrovirus GAG fragment interacts with Tsg101, and wherein said first and second proteins interact to form said isolated protein complex.

13. The isolated protein complex of claim 12, wherein said retrovirus is a lentivirus.

14. The isolated protein complex of claim 13, wherein said lentivirus is a primate lentivirus.

15. The isolated protein complex of claim 14, wherein said primate lentivirus is selected from the group consisting of HIV-1, HIV-2, HIV-3, and simian immunodeficiency viruses.

16. The isolated protein complex of claim 13, wherein said lentivirus is a non-primate lentivirus selected from the group consisting of bovine lentiviruses, feline lentiviruses, and ovine/caprine lentiviruses.

17. An isolated protein complex comprising:
   (a) a first protein which is selected from the group consisting of
       (i) a Tsg101 fragment that comprises a UEV domain and interacts with an HIV GAGp6 late domain,
       (ii) a first polypeptide that has an amino acid sequence at least about 90% identical to the UEV domain of Tsg101 and that interacts with an HIV GAGp6 late domain, and
       (iii) a fusion protein comprising (i) or (ii); and
   (b) a second protein which is selected from the group consisting of
       (1) a retrovirus GAG comprising a P(T/S)AP late domain motif, (2) a second polypeptide that has an amino acid sequence at least about 90% identical to that of said retrovirus GAG and that interacts with Tsg101, (3) a fragment of (1) or (2) that comprises a P(T/S)AP late domain motif and interacts with Tsg101, and (4) a fusion protein comprising (1), (2) or (3);

wherein said first and second proteins interact to form said isolated protein complex.

18. The isolated protein complex of claim 17, wherein said retrovirus is a lentivirus.

19. The isolated protein complex of claim 18, wherein said lentivirus is a primate lentivirus.

20. The isolated protein complex of claim 19, wherein said primate lentivirus is selected from the group consisting of HIV-1, HIV-2, HIV-3, and simian immunodeficiency viruses.

21. The isolated protein complex of claim 18, wherein said lentivirus is a non-primate lentivirus selected from the group consisting of bovine lentiviruses, feline lentiviruses, and ovine/caprine lentiviruses.

22. An isolated protein complex comprising:

(a) a first protein which is selected from the group consisting of (i) a Tsg101 fragment that comprises a UEV domain and interacts with an HIV GAGp6 late domain, (ii) a first polypeptide that interacts with an HIV GAGp6 late domain and has an amino acid sequence at least about 90% identical to that of the Tsg101 UEV domain, or said Tsg101 fragment, and (iii) a fusion protein comprising (i) or (ii); and (b) a second protein which is selected from the group consisting of (1) a primate lentivirus GAG that interacts with Tsg101, (2) a primate lentivirus GAG homologue that has an amino acid sequence at least about 90% identical to that of said primate lentivirus GAG and that interacts with Tsg101, (3) a primate lentivirus GAGp6 that interacts with Tsg101, (4) a primate lentivirus GAGp6 homologue that has an amino acid sequence at least about 90% identical to that of HIV GAGp6 and that interacts with Tsg101, (5) a fragment of (1), (2), (3), or (4) that comprises a late domain motif and interacts with Tsg101, and (6) a fusion protein comprising (1), (2), (3), (4), or (5);

wherein said first and second proteins interact to form said isolated protein complex.

23. An isolated protein complex comprising:

a first fusion protein comprising a Tsg101 fragment that interacts with an HIV GAGp6 late domain interacting with a second fusion protein comprising a fragment of HIV GAG comprising an HIV GAGp6 late domain motif.

24. An isolated protein complex having a first polypeptide covalently linked to a second polypeptide, wherein said first polypeptide is a Tsg101 fragment that comprises a UEV domain and interacts with an HIV GAGp6 late domain or a homologue of said Tsg101 fragment that has an amino acid sequence at least about 75% identical to said Tsg101 fragment, wherein said Tsg101 fragment or said homologue of said Tsg101 fragment interacts with an HIV GAGp6 late domain, and wherein said second polypeptide is HIV GAG or a fragment of HIV GAG that comprises an HIV GAGp6 late domain, a homologue of HIV GAG or said fragment of HIV GAG, that has an amino acid sequence at least about 75% identical to that of said HIV GAG or said fragment of HIV GAG, and said homologue interacts with Tsg101; and wherein said first and second polypeptides interact to form said isolated protein complex.

25. A method for selecting modulators of a protein complex according to claim 1, comprising:

providing the protein complex;

contacting said protein complex with a test compound; and determining the presence or absence of binding of said test compound to said protein complex.

26. A method for selecting modulators of an interaction between a first protein and a second protein, (a) said first protein being selected from group consisting of (i) Tsg101 protein, (ii) a Tsg101 protein homologue having an amino acid sequence at least 90% identical to that of Tsg101 and capable of interacting with HIV GAGp6, (iii) a Tsg101 protein fragment containing the Tsg101 UEV domain, and (iv) a fusion protein containing said Tsg101 protein, said Tsg101 protein homologue or said Tsg101 protein fragment; and (b) said second protein being selected from the group consisting of (1) HIV GAG polypeptide, (2) a HIV GAG polypeptide homologue having an amino acid sequence at least 90% identical to that of HIV GAG polypeptide and capable of interacting with Tsg101, (3) HIV GAGp6 protein, (4) a HIV GAGp6 homologue having an amino acid sequence at least 90% identical to that of HIV GAGp6 polypeptide and capable of interacting with Tsg101, (5) a HIV GAGp6 fragment capable of interacting with Tsg101, and (6) a fusion protein containing said HIV GAG polypeptide, said HIV GAG polypeptide homologue, said HIV GAGp6 protein, said HIV GAGp6 homologue or said HIV GAGp6 fragment, said method comprising:

contacting said first protein with said second protein in the presence of one or more test compounds; and determining the interaction between said first protein and said second protein.

27. The method of claim 26, wherein at least one of said first and second proteins is a fusion protein having a detectable tag.

28. The method of claim 26, wherein said contacting step is conducted in a substantially cell free environment.

29. The method of claim 26, wherein said contacting step is conducted in a host cell.

30. The method of claim 29, wherein said host cell is a yeast cell.

31. A method for selecting modulators of an interaction between a first protein and a second protein, (a) said first protein being selected from group consisting of (i) Tsg101 protein, (ii) a Tsg101 protein homologue having an amino acid sequence at least 90% identical to that of Tsg101 and capable of interacting with HIV GAGp6, (iii) a Tsg101 protein fragment containing the Tsg101 UEV domain, and (iv) a fusion protein containing said Tsg101 protein, said Tsg101 protein homologue or said Tsg101 protein fragment; and (b) said second protein being selected from the group consisting of
(1) a retrovirus GAG polypeptide having the P(T/S)AP late domain motif,
(2) a homologue of said retrovirus GAG polypeptide, said homologue having an amino acid sequence at least 90% identical to that of said retrovirus GAG polypeptide and capable of interacting with Tsg101,
(3) a fragment of said retrovirus GAG polypeptide, said fragment being capable of interacting with Tsg101, and
(4) a fusion protein containing said retrovirus GAG polypeptide, said retrovirus GAG polypeptide homologue or said retrovirus GAG polypeptide fragment, said method comprising:

contacting said first protein with said second protein in the presence of one or more test compounds; and
determining the interaction between said first protein and said second protein.

32. The method of claim 31, wherein said contacting step is conducted in a substantially cell free environment.

33. The method of claim 32, wherein said contacting step is conducted in a host cell.

34. A method for selecting modulators of the protein complex of claim 8, comprising:
contacting said protein complex with a test compound; and determining the interaction between said first protein and said second protein.

35. A method for selecting modulators of the protein complex of claim 17, comprising:
contacting said protein complex with a test compound; and
determining the interaction between said first protein and said second protein.

36. A method for selecting modulators of the protein complex of claim 22, comprising:
contacting said protein complex with a test compound; and
determining the interaction between said first protein and said second protein.

37. A method for selecting modulators of an interaction between a first polypeptide and a second polypeptide,
(a) said first polypeptide being selected from group consisting of
(i) Tsg101 protein,
(ii) a Tsg101 protein homologue having an amino acid sequence at least 90% identical to that of Tsg101 and capable of interacting with HIV GAGp6 late domain, and
(iii) a Tsg101 protein fragment containing the Tsg101 UEV domain; and
(b) said second polypeptide being selected from the group consisting of
(1) HIV GAG polypeptide,
(2) a HIV GAG polypeptide homologue having an amino acid sequence at least 90% identical to that of HIV GAG polypeptide and capable of interacting with Tsg101,
(3) HIV GAGp6 protein,
(4) a HIV GAGp6 homologue having an amino acid sequence at least 90% identical to that of HIV GAGp6 polypeptide and capable of interacting with Tsg101, and (5) a HIV GAGp6 fragment capable of interacting with Tsg101, said method comprising:
providing in a host cell a first fusion protein having said first polypeptide, and a second fusion protein having said second polypeptide, wherein a DNA binding domain is fused to one of said first and second polypeptides while a transcription-activating domain is fused to the other of said first and second polypeptides;
providing in said host cell a reporter gene, wherein the transcription of the reporter gene is determined by the interaction between the first polypeptide and the second polypeptide;
allowing said first and second fusion proteins to interact with each other within said host cell in the presence of a test compound; and
determining the presence or absence of expression of said reporter gene.

38. The method of claim 37, wherein said host cell is a yeast cell.

39. A method for selecting modulators of the protein complex of claim 17, comprising:
providing in a host cell a first fusion protein containing said first protein, and a second fusion protein containing said second protein, wherein a DNA binding domain is fused to one of said first and second polypeptides while a transcription-activating domain is fused to the other of said first and second proteins;
providing in said host cell a reporter gene, wherein the transcription of the reporter gene is determined by the interaction between the first protein and the second protein;
allowing said first and second fusion proteins to interact with each other within said host cell in the presence of a test compound; and
determining the presence or absence of expression of said reporter gene.

40. A method for selecting modulators of the protein complex of claim 22, comprising:
providing in a host cell a first fusion protein containing said first protein, and a second fusion protein containing said second protein, wherein a DNA binding domain is fused to one of said first and second polypeptides while a transcription-activating domain is fused to the other of said first and second proteins;
providing in said host cell a reporter gene, wherein the transcription of the reporter gene is determined by the interaction between the first protein and the second protein;
allowing said first and second fusion proteins to interact with each other within said host cell in the presence of a test compound; and
determining the presence or absence of expression of said reporter gene.

41. A composition comprising:
(a) a first expression vector having a nucleic acid encoding a first protein which is selected from the group consisting of
(i) Tsg101,
(ii) a Tsg101 fragment that comprises a UEV domain and interacts with an HIV GAGp6 late domain,
(iii) a first polypeptide having an amino acid sequence at least about 75% identical to that of (i) or (ii), and that interacts with an HIV GAGp6 late domain, and
(iv) a first fusion protein comprising (i), (ii), or (iii); and
(b) a second expression vector having a nucleic acid encoding a second protein selected from the group consisting of (1) HIV GAG,
(2) HIV GAGp6,
(3) a fragment of (1) or (2) that interacts with Tsg101,
(4) an HIV GAGp6 fragment that comprises an HIV GAGp6 late domain motif and interacts with Tsg101,
(5) a second polypeptide that has an amino acid sequence at least about 75% identical to that of (1), (2), (3), or (4), and that interacts with Tsg101, and
(6) a second fusion protein comprising (1), (2), (3), (4), or (5);
wherein said first and second proteins interact to form a protein complex.

42. A host cell comprising:
(a) a first expression vector having a nucleic acid encoding a first protein which is selected from the group consisting of
  (i) Tsg101,
  (ii) a Tsg101 fragment that comprises a UEV domain and interacts with an HIV GAGp6 late domain,
  (iii) a first polypeptide that has an amino acid sequence at least about 75% identical to that of (i) or (ii), and interacts with an HIV GAGp6 late domain, and
  (iv) a first fusion protein comprising (i), (ii), or (iii); and
(b) a second expression vector having a nucleic acid encoding a second protein selected from the group consisting of
  (1) HIV GAG,
  (2) HIV GAGp6,
  (3) a fragment of (1) or (2) that comprises a late domain motif and interacts with Tsg101,
  (4) a second polypeptide that has an amino acid sequence at least about 75% identical to that of (1), (2), or (3), and interacts with Tsg101, and
  (5) a second fusion protein comprising (1), (2), (3), or (4);
wherein said first and second proteins interact to form a protein complex.

43. The host cell of claim 42, wherein said host cell is a yeast cell.

44. The host cell of claim 42, wherein said first and second proteins are fusion proteins.

45. The host cell of claim 42, wherein one of said first and second nucleic acids is operably linked to a nucleic acid encoding a DNA binding domain, and the other of said first and second nucleic acids is operably linked to a nucleic acid encoding a transcription-activation domain, whereby two fusion proteins can be produced in said host cell.

46. The host cell of claim 42, further comprising a reporter gene, wherein the expression of the reporter gene is determined by the interaction between the first protein and the second protein.

47. A host cell comprising:
(a) a first expression vector having a first nucleic acid encoding a first protein which is selected from the group consisting of
  (i) Tsg101,
  (ii) a Tsg101 fragment that comprises a UEV domain and interacts with an HIV GAGp6 late domain,
  (iii) a first polypeptide that has an amino acid sequence at least about 90% identical to (i) or (ii) and interacts with an HIV GAGp6 late domain, and
  (iv) a first fusion protein comprising (i), (ii), or (iii); and
(b) a second expression vector having a second nucleic acid encoding a second protein selected from the group consisting of
  (1) a retrovirus GAG that comprises a P(T/S)AP late domain motif and interacts with Tsg101,
  (2) a retrovirus GAG fragment comprising a P(T/S)AP late domain motif that interacts with Tsg101,
  (3) a second polypeptide that has an amino acid sequence at least about 90% identical to (1) or (2) and interacts with Tsg101, and
  (4) a second fusion protein comprising (1), (2), or (3);
wherein said first and second proteins interact to form a protein complex.

48. A method for providing a compound capable of interfering with an interaction between the first and second proteins in the protein complex of claim 8 comprising:
providing atomic coordinates defining a three-dimensional structure of said protein complex; and
designing or selecting compounds capable of interfering with the interaction between said first protein and said second protein based on said atomic coordinates.

49. A method for providing a compound capable of interfering with an interaction between the first and second proteins in the protein complex of claim 17 comprising:
providing atomic coordinates defining a three-dimensional structure of said protein complex; and
designing or selecting compounds capable of interfering with the interaction between said first protein and said second protein based on said atomic coordinates.

50. A method for providing a compound capable of interfering with an interaction between the first and second proteins in the protein complex of claim 22 comprising:
providing atomic coordinates defining a three-dimensional structure of said protein complex; and
designing or selecting compounds capable of interfering with the interaction between said first protein and said second protein based on said atomic coordinates.

51. A method for selecting a compound capable of inhibiting a protein-protein interaction between Tsg101 and HIV GAGp6, comprising:
contacting a test compound with a protein selected from group consisting of
  (i) Tsg101 protein,
  (ii) a Tsg101 protein homologue having an amino acid sequence at least 90% identical to that of Tsg101 and capable of interacting with HIV GAGp6,
  (iii) a Tsg101 protein fragment containing the Tsg101 UEV domain, and
  (iv) a fusion protein containing said Tsg101 protein, said Tsg101 protein homologue or said Tsg101 protein fragment; and
determining whether said test compound is capable of binding said protein.

52. The method of claim 51, further comprising testing a test compound capable of binding said protein for its ability to interfere with a protein-protein interaction between Tsg101 and HIV GAGp6.

53. The method of claim 52, further comprising testing a test compound capable of binding said protein for its ability to inhibit HIV viral budding from an HIV-infected host cell.

54. A method for selecting a compound capable of inhibiting a protein-protein interaction between Tsg101 and HIV GAGp6, comprising:
providing atomic coordinates defining a three-dimensional structure of a protein selected from group consisting of
  (i) Tsg101 protein,
  (ii) a Tsg101 protein homologue having an amino acid sequence at least 90% identical to that of Tsg101 and capable of interacting with HIV GAGp6,
  (iii) a Tsg101 protein fragment containing the Tsg101 UEV domain, and (iv) a fusion protein containing said Tsg101 protein, said Tsg101 protein homologue or said Tsg101 protein fragment; and designing or selecting compounds capable of interacting with said protein based on said atomic coordinates.

55. The method of claim 54, further comprising testing a compound capable of interacting with said protein for its ability to interfere with a protein-protein interaction between Tsg101 and HIV GAGp6.

56. The method of claim 54, further comprising testing a test compound capable of interacting with said protein for its ability to inhibit HIV viral budding from an HIV-infected host cell.

57. An expression vector comprising:
(a) a first nucleic acid encoding a first protein which is selected from the group consisting of
  (i) Tsg101,
  (ii) a Tsg101 fragment that comprises a UEV domain interacts with an HIV GAGp6 late domain,
  (iii) a first polypeptide that has an amino acid sequence at least about 75% identical to that of (i) or (ii) and interacts with an HIV GAGp6 late domain, and
  (iv) a first fusion protein comprising (i), (ii), or (iii); and
(b) a second nucleic acid encoding a second protein selected from the group consisting of
  (1) HIV GAG,
  (2) HIV GAGp6,
  (3) a fragment of (1) or (2) that comprises an HIV GAGp6 late domain motif and interacts with Tsg101,
  (4) a second polypeptide that comprises an amino acid sequence at least about 75% identical to that of (1), (2), or (3) and that interacts with Tsg101, and
  (5) a second fusion protein comprising (1), (2), (3), or (4);
wherein said first and second proteins interact to form a protein complex.

58. A host cell comprising the expression vector of claim 57.

59. A non-human host cell expressing:
(a) a first protein which is selected from the group consisting of
  (i) Tsg101,
  ii) a Tsg101 fragment that comprises a UEV domain and interacts with an HIV GAGp6 late domain,
  (iii) a first polypeptide that has an amino acid sequence at least about 75% identical to that of (i) or (ii) and interacts with an HIV GAGp6 late domain, and
  (iv) a first fusion protein comprising (i), (ii), or (iii); and
(b) a second protein selected from the group consisting of
  (1) HIV GAG,
  (2) HIV GAGp6,
  (3) a fragment of (1) or (2) that comprises an HIV GAGp6 late domain motif and interacts with Tsg101,
  (4) a second polypeptide that has an amino acid sequence at least about 75% identical to that of (1), (2), or (3) and interacts with Tsg101, and
  (5) a second fusion protein comprising (1), (2), (3), or (4);
wherein said first and second proteins interact to form a protein complex within said non-human host cell.

60. An isolated human host cell comprising:
(a) a first promoter operably linked to a first chimeric nucleic acid encoding a first protein selected from the group consisting of
  (i) Tsg101,
  (ii) a Tsg101 fragment that comprises a UEV domain and interacts with an HIV GAGp6 late domain,
  (iii) a first polypeptide that has an amino acid sequence at least about 75% identical to that of (i) or (ii) and interacts with an HIV GAGp6 late domain, and
  (iv) a first fusion protein comprising (i), (ii), or (iii); and
(b) a second promoter operably linked to a second chimeric nucleic acid encoding a second protein selected from the group consisting of
  (1) HIV GAG,
  (2) HIV GAGp6,
  (3) a fragment of (1) or (2) that comprises an HIV GAGp6 late domain motif and interacts with Tsg101,
  (4) a second polypeptide that has an amino acid sequence at least about 75% identical to that of(1), (2), or (3) and interacts with Tsg101, and
  (5) a second fusion protein comprising (1), (2), (3), or (4);
wherein said first and second proteins interact to form a protein complex within said isolated human host cell.

61. The isolated protein complex of claim 5, wherein said first protein is said Tsg101 fragment which consists essentially of a UEV domain.

62. The isolated protein complex of claim 5, wherein said first protein is said Tsg101 fragment which comprises a portion of Tsg101 having no more than 207 contiguous amino acid residues, further comprising a UEV domain.

63. The isolated protein complex of claim 8, wherein said first protein is said Tsg101 fragment which consists essentially of a UEV domain.

64. The isolated protein complex of claim 8, wherein said first protein is said Tsg101 fragment which comprises a portion of Tsg101 having no more than 207 contiguous amino acid residues, further comprising a UEV domain.

* * * * *

```
                        SEQUENCE LISTING

<160> NUMBER OF SEQ ID NOS: 32

<210> SEQ ID NO 1
<211> LENGTH: 4
<212> TYPE: PRT
<213> ORGANISM: Human immunodeficiency virus

<400> SEQUENCE: 1

Pro Thr Ala Pro
1

<210> SEQ ID NO 2
<211> LENGTH: 4
<212> TYPE: PRT
<213> ORGANISM: Mutant human immunodeficiency virus

<400> SEQUENCE: 2

Pro Thr Thr Pro
1

<210> SEQ ID NO 3
<211> LENGTH: 4
<212> TYPE: PRT
<213> ORGANISM: Human immunodeficiency virus

<400> SEQUENCE: 3

Pro Ser Ala Pro
1

<210> SEQ ID NO 4
<211> LENGTH: 4
<212> TYPE: PRT
<213> ORGANISM: Mutant human immunodeficiency virus

<400> SEQUENCE: 4
```

Pro Ser Thr Pro
1

<210> SEQ ID NO 5
<211> LENGTH: 4
<212> TYPE: PRT
<213> ORGANISM: Mutant human immunodeficiency virus

<400> SEQUENCE: 5

Pro Ile Ala Pro
1

<210> SEQ ID NO 6
<211> LENGTH: 4
<212> TYPE: PRT
<213> ORGANISM: Mutant human immunodeficiency virus

<400> SEQUENCE: 6

Pro Ile Thr Pro
1

<210> SEQ ID NO 7
<211> LENGTH: 5
<212> TYPE: PRT
<213> ORGANISM: Human immunodeficiency virus

<400> SEQUENCE: 7

Glu Pro Thr Ala Pro
1               5

<210> SEQ ID NO 8
<211> LENGTH: 5
<212> TYPE: PRT
<213> ORGANISM: Human immunodeficiency virus

<400> SEQUENCE: 8

Glu Pro Ser Ala Pro
1               5

<210> SEQ ID NO 9
<211> LENGTH: 5
<212> TYPE: PRT
<213> ORGANISM: Human immunodeficiency virus

<400> SEQUENCE: 9

Pro Thr Ala Pro Pro
1               5

<210> SEQ ID NO 10
<211> LENGTH: 5
<212> TYPE: PRT
<213> ORGANISM: Human immunodeficiency virus

<400> SEQUENCE: 10

Pro Ser Ala Pro Pro
1               5

<210> SEQ ID NO 11
<211> LENGTH: 6
<212> TYPE: PRT
<213> ORGANISM: Human immunodeficiency virus

<400> SEQUENCE: 11

Glu Pro Thr Ala Pro Pro

-continued

```
<210> SEQ ID NO 12
<211> LENGTH: 6
<212> TYPE: PRT
<213> ORGANISM: Human immunodeficiency virus

<400> SEQUENCE: 12

Glu Pro Ser Ala Pro Pro
1               5

<210> SEQ ID NO 13
<211> LENGTH: 6
<212> TYPE: PRT
<213> ORGANISM: Human immunodeficiency virus

<400> SEQUENCE: 13

Pro Glu Pro Thr Ala Pro
1               5

<210> SEQ ID NO 14
<211> LENGTH: 6
<212> TYPE: PRT
<213> ORGANISM: Human immunodeficiency virus

<400> SEQUENCE: 14

Pro Glu Pro Ser Ala Pro
1               5

<210> SEQ ID NO 15
<211> LENGTH: 7
<212> TYPE: PRT
<213> ORGANISM: Human immunodeficiency virus

<400> SEQUENCE: 15

Arg Pro Glu Pro Thr Ala Pro
1               5

<210> SEQ ID NO 16
<211> LENGTH: 7
<212> TYPE: PRT
<213> ORGANISM: Human immunodeficiency virus

<400> SEQUENCE: 16

Arg Pro Glu Pro Ser Ala Pro
1               5

<210> SEQ ID NO 17
<211> LENGTH: 7
<212> TYPE: PRT
<213> ORGANISM: Human immunodeficiency virus

<400> SEQUENCE: 17

Pro Glu Pro Thr Ala Pro Pro
1               5

<210> SEQ ID NO 18
<211> LENGTH: 7
<212> TYPE: PRT
<213> ORGANISM: Human immunodeficiency virus

<400> SEQUENCE: 18

Pro Glu Pro Ser Ala Pro Pro
1               5
```

```
<210> SEQ ID NO 19
<211> LENGTH: 8
<212> TYPE: PRT
<213> ORGANISM: Human immunodeficiency virus

<400> SEQUENCE: 19

Glu Pro Thr Ala Pro Pro Glu Glu
1               5

<210> SEQ ID NO 20
<211> LENGTH: 8
<212> TYPE: PRT
<213> ORGANISM: Human immunodeficiency virus

<400> SEQUENCE: 20

Glu Pro Ser Ala Pro Pro Glu Glu
1               5

<210> SEQ ID NO 21
<211> LENGTH: 8
<212> TYPE: PRT
<213> ORGANISM: Human immunodeficiency virus

<400> SEQUENCE: 21

Glu Pro Thr Ala Pro Pro Ala Glu
1               5

<210> SEQ ID NO 22
<211> LENGTH: 9
<212> TYPE: PRT
<213> ORGANISM: Human immunodeficiency virus

<400> SEQUENCE: 22

Pro Glu Pro Thr Ala Pro Pro Glu Glu
1               5

<210> SEQ ID NO 23
<211> LENGTH: 9
<212> TYPE: PRT
<213> ORGANISM: Human immunodeficiency virus

<400> SEQUENCE: 23

Pro Glu Pro Thr Ala Pro Pro Ala Glu
1               5

<210> SEQ ID NO 24
<211> LENGTH: 9
<212> TYPE: PRT
<213> ORGANISM: Human immunodeficiency virus

<400> SEQUENCE: 24

Pro Glu Pro Ser Ala Pro Pro Glu Glu
1               5

<210> SEQ ID NO 25
<211> LENGTH: 10
<212> TYPE: PRT
<213> ORGANISM: Human immunodeficiency virus

<400> SEQUENCE: 25

Arg Pro Glu Pro Thr Ala Pro Pro Glu Glu
1               5                   10

<210> SEQ ID NO 26
```

```
<211> LENGTH: 10
<212> TYPE: PRT
<213> ORGANISM: Human immunodeficiency virus

<400> SEQUENCE: 26

Arg Pro Glu Pro Ser Ala Pro Pro Glu Glu
1               5                   10

<210> SEQ ID NO 27
<211> LENGTH: 10
<212> TYPE: PRT
<213> ORGANISM: Human immunodeficiency virus

<400> SEQUENCE: 27

Arg Pro Glu Pro Thr Ala Pro Pro Ala Glu
1               5                   10

<210> SEQ ID NO 28
<211> LENGTH: 10
<212> TYPE: PRT
<213> ORGANISM: Human immunodeficiency virus

<400> SEQUENCE: 28

Arg Pro Glu Pro Ser Ala Pro Pro Ala Glu
1               5                   10

<210> SEQ ID NO 29
<211> LENGTH: 13
<212> TYPE: PRT
<213> ORGANISM: Human immunodeficiency virus

<400> SEQUENCE: 29

Leu Gln Ser Arg Pro Glu Pro Thr Ala Pro Pro Glu Glu
1               5                   10

<210> SEQ ID NO 30
<211> LENGTH: 13
<212> TYPE: PRT
<213> ORGANISM: Human immunodeficiency virus

<400> SEQUENCE: 30

Leu Gln Ser Arg Pro Glu Pro Ser Ala Pro Pro Glu Glu
1               5                   10

<210> SEQ ID NO 31
<211> LENGTH: 14
<212> TYPE: PRT
<213> ORGANISM: Human immunodeficiency virus

<400> SEQUENCE: 31

Leu Gln Ser Arg Pro Glu Pro Thr Ala Pro Pro Glu Glu Ser
1               5                   10

<210> SEQ ID NO 32
<211> LENGTH: 14
<212> TYPE: PRT
<213> ORGANISM: Human immunodeficiency virus

<400> SEQUENCE: 32

Leu Gln Ser Arg Pro Glu Pro Ser Ala Pro Pro Glu Glu Ser
1               5                   10
```